United States Patent [19]

Ingenito et al.

[11] Patent Number: 4,828,501
[45] Date of Patent: May 9, 1989

[54] COMPACT INTERACTIVE TRAINING MANIKIN SYSTEM

[75] Inventors: Michael Ingenito; Eve J. Ingenito; Michael P. Ingenito, all of White Plains, N.Y.

[73] Assignee: Michael Ingenito, White Plains, N.Y.

[21] Appl. No.: 28,593

[22] Filed: Mar. 20, 1987

[51] Int. Cl.[4] ............................................. G09B 23/28
[52] U.S. Cl. ..................................... 434/265; 434/262
[58] Field of Search ........................ 434/262, 265, 267

[56] References Cited

U.S. PATENT DOCUMENTS

| | | | |
|---|---|---|---|
| 4,360,345 | 11/1982 | Hon | 434/265 |
| 4,583,524 | 4/1986 | Hutchins | 434/262 |
| 4,611,998 | 9/1986 | Ramamurthy | 434/265 |

Primary Examiner—Leo P. Picard
Attorney, Agent, or Firm—Laff, Whitesel, Conte & Saret

[57] ABSTRACT

A manikin and control system is provided for use by a student practicing a procedure normally applied to the human body, such as cardiopulmonary resuscitation. The system includes a manikin that has an artificial lung into which the student can blow to expand the lung, and a resilient chest which the student can compress. Sensors are provided in the manikin to accurately detect the instantaneous amount of lung expansion and chest compression. An A/D converter converts the sensor signals to digital signals and inputs them to a compact controller based on an inexpensive microcomputer chip which also stores the control program in ROM. Pushbuttons on the controller's front panel enable the student to select any one of a variety of teaching routines prestored in the microcomputer's ROM. The microcomputer then uses lamps on the panel and a speech synthesizer having prerecorded human speech stored in external ROM chips to issue instructions and advice to the student. These are contingent on his performance of the selected routine as detected by the sensors. However, a prestored interrupt routine always enables the student to switch from the current routine to any other, or to get an immediate repeat of the last message from the system. Transducers are provided for simulating a carotid pulse and shallow breathing in the manikin, and these can be activated by an instructor via remote control using a wireless transmitter and receiver pair.

56 Claims, 26 Drawing Sheets

FIG. 6A
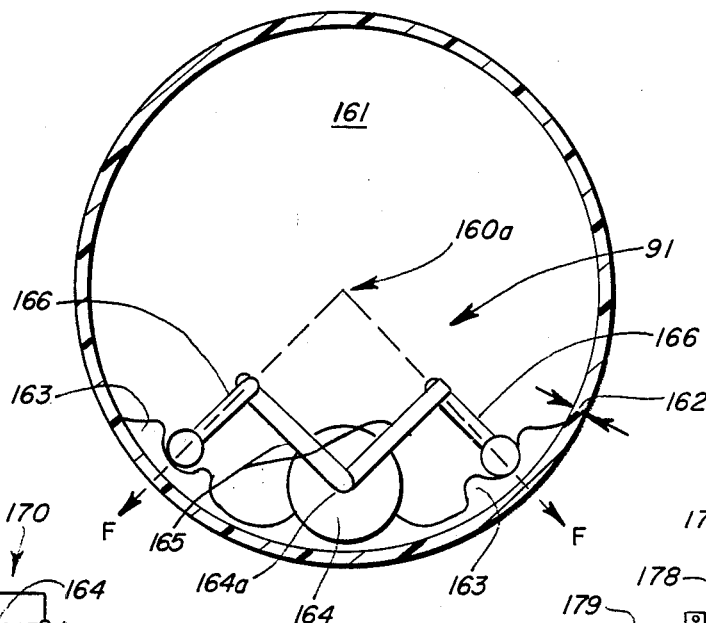
FIG. 6B
FIG. 6D
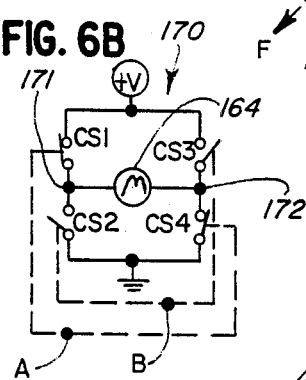
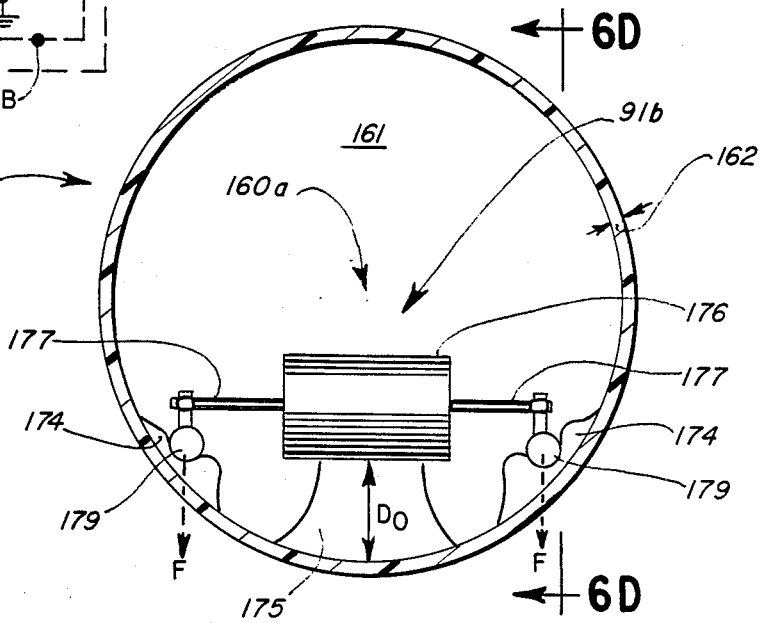
FIG. 6C

VENTILATION ROUTINE

SINGLE CHEST COMPRESSION SEQUENCE

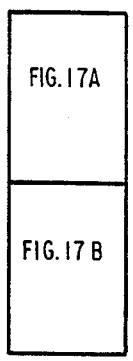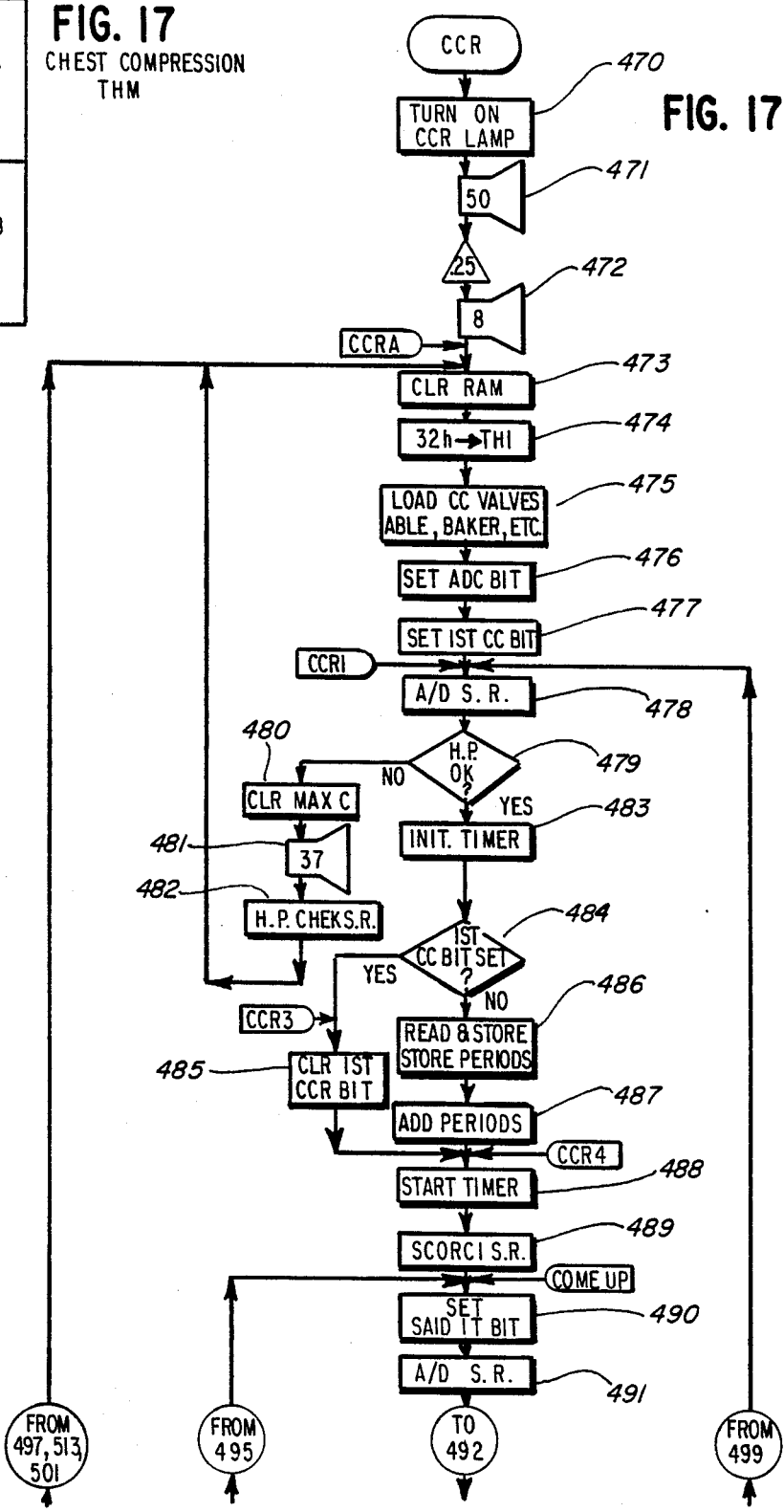
FIG. 17 CHEST COMPRESSION THM
FIG. 17A

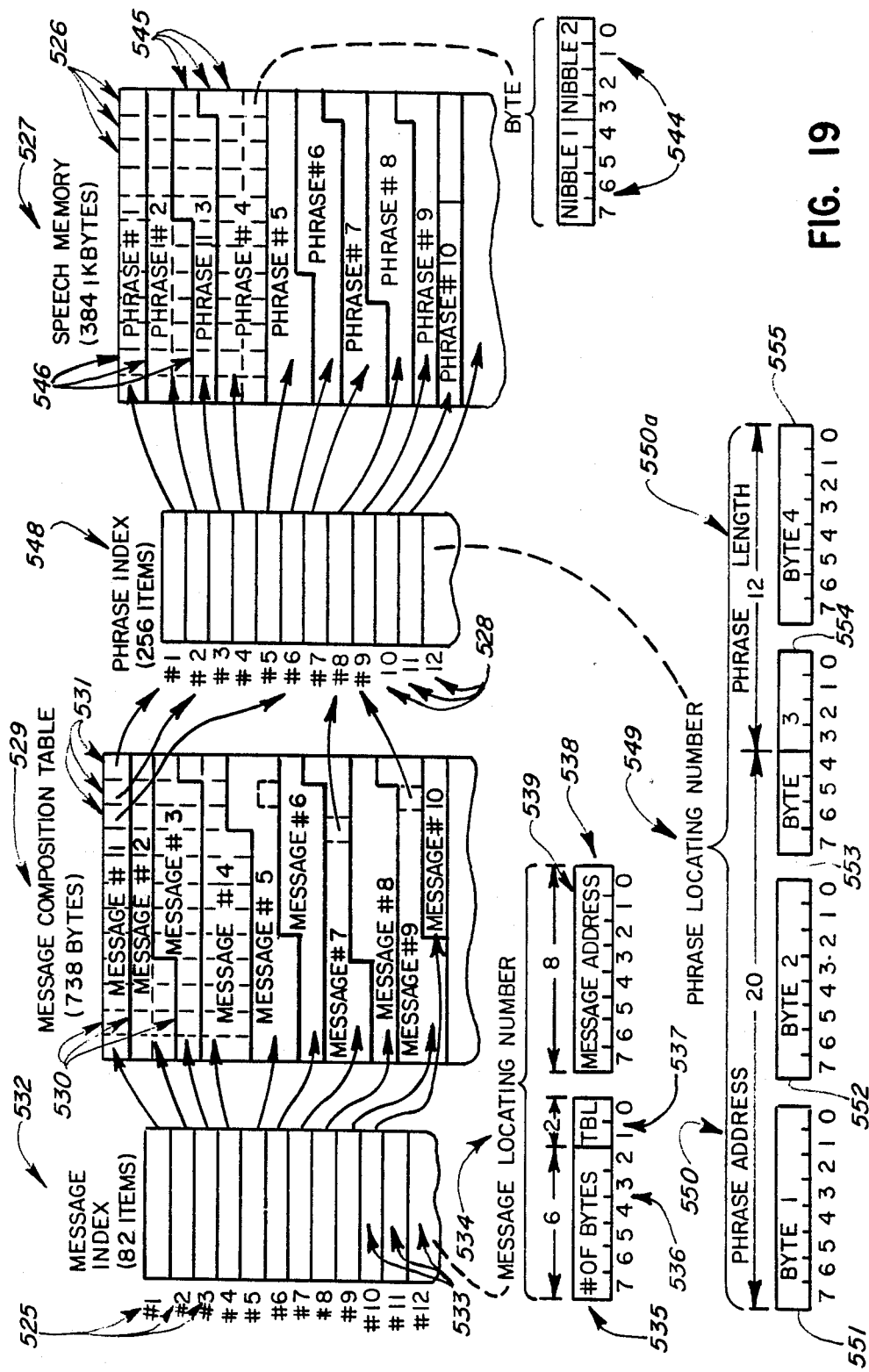

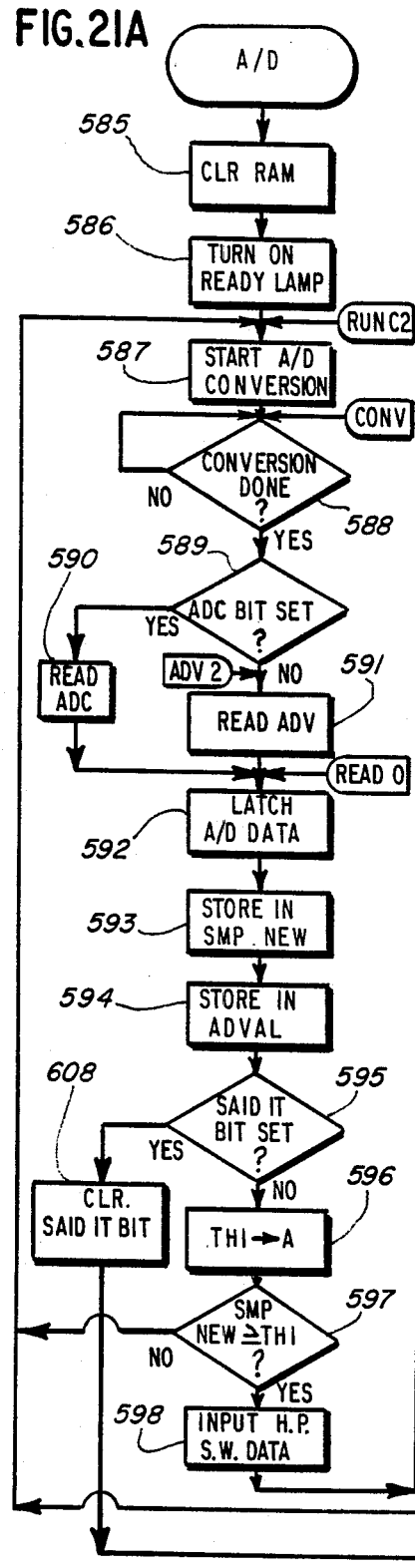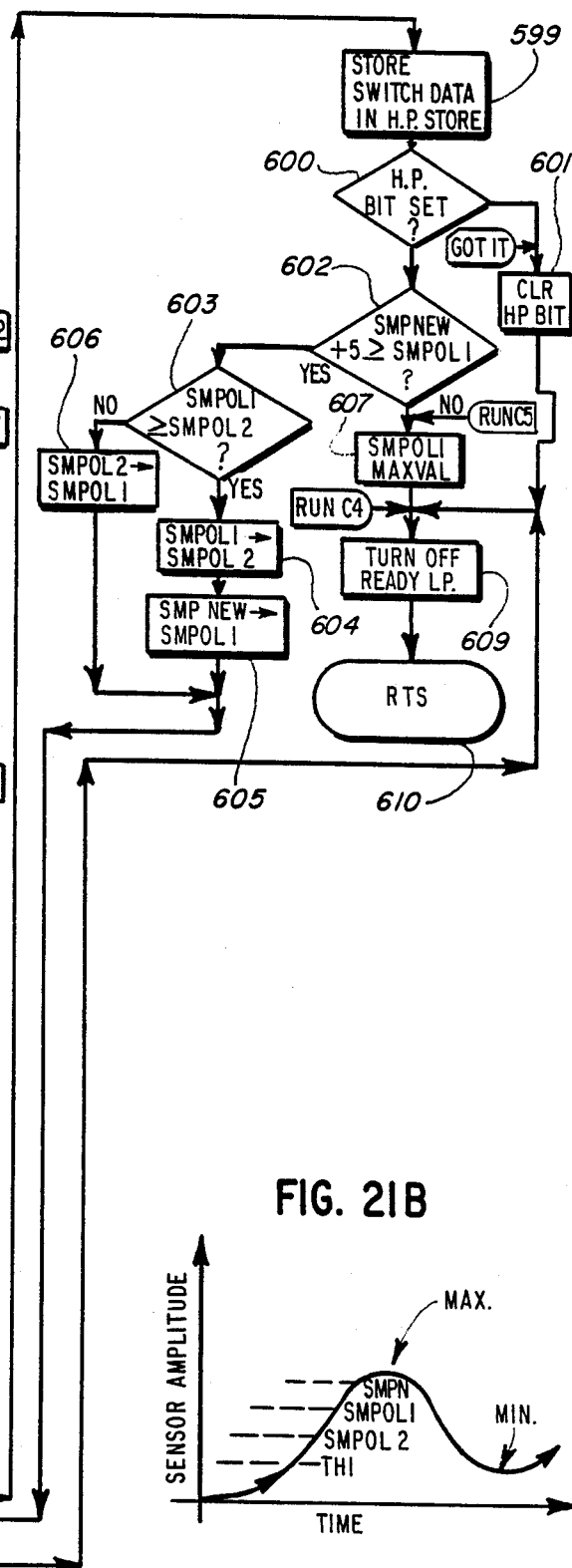
FIG. 21A
FIG. 21B

COMPACT INTERACTIVE TRAINING MANIKIN SYSTEM

This invention relates to training manikins, and more particularly to a training manikin system having a very compact controller with a prerecorded human voice interface for coaching the user.

BACKGROUND

Manikins Used with Live Instructors

Models of the human body called manikins are used in teaching many skills. In the medical and safety fields, manikins are a common and important aid in teaching Cardiopulmonary Resuscitation (hereafter "CPR"), a combination of artificial respiration and heart massage.

Traditionally a class of students is first taught the CPR procedure by a live instructor, after which the instructor divides the class into teams to practice on a manikin. During practice the instructor goes from team to team, commenting, correcting and coaching. The students use the manikin to practice mouth-to-mouth breathing, chest compressions for restoring circulation, and first aid procedures for choking.

Prior art training manikins for CPR have generally been equipped with an electronic signal box the front panel of which has lamps that give some feedback to the student. For example, in a typical arrangement the panel has three different colored lamps to signal the following:

Green lamp: Lights up when 800 cc of air enters the manikin's lungs. Is off when less than this amount is in the lungs.

Yellow lamp: Lights up when the chest is compressed 1½ inches. Is off when the chest is compressed less than this amount.

Red lamp: Lights up as a warning when an incorrect hand position is used during chest compressions.

Also, an electronic metronome has been provided which emits an audible "tick".

In addition to the above-mentioned lights, the higher cost manikins have been equipped with strip charts that record the student's performance as he practices. This enables an instructor to come by, read the chart, and discuss the results with the student. The instructor may also show the student how to read the chart himself.

Some CPR training manikins have been equipped with other internal and external devices that allow for some degree of measurement, recording, and visual indication of the student's efforts when he or she is practicing various procedures. But even the most sophisticated of these have many shortcomings and limitations. Also, most conventional training manikins, except for very expensive systems, are designed for use in training courses having a live instructor.

Instructorless Systems Systems that do not require a live instructor have advantages, since there is a shortage of trained, highly motivated persons with the required time and temperament for the very repetitive, vocalized teaching required. Another benefit is standardization of instruction.

Until now, however, complete elimination of the instructor has required an elaborate, complex, and cumbersome array of electronic hardware. In one such system, the manikin is internally fitted with sensors and coupled via an electrical cable to a system consisting of a computer, keyboard and light pen, two television monitors, a video disc machine, and a computer controlled audio machine. All of this is cabled together and powered by the AC line.

Such systems are not easily portable, and are also very expensive (in the neighborhood of $25,000). Their maintenance entails additional cost and requires highly skilled personnel. A principal objective of the present invention is therefore to equal or at least approach the performance of such a system at a far more reasonable cost, with a far less complex, much more compact, rugged and portable product.

SUMMARY OF THE INVENTION

This invention provides an improved teaching manikin system having an interactive teaching system with voice coaching which is expected to sell for about $1,000. The electronic controller for this system, in addition to being inexpensive, is compact enough to fit in a space about the size of a textbook.

This system enables one-on-one training and interaction with the student via sensors in the manikin, input buttons on a touch panel, and immediate voice feedback. The sensing means in the manikin are proportional in nature rather than simple on/off limit switches.

The system monitors the student and gives him or her instant coaching feedback by means of a natural-sounding prerecorded voice. It also allows the student to select the particular phase of training he or she wishes to practice.

The invention also provides a means of simulating shallow breathing and a carotid pulse in the manikin at times preselected or secretly chosen by an instructor so that the student has a more realistic opportunity to learn to recognize these faint signs of revival and adjust his or her actions accordingly.

Thus, in keeping with one aspect of the invention, a simulation manikin system is provided for use by a student attempting to practice a procedure normally applied to the human body, such as cardiopulmonary resuscitation. The system includes a manikin that has an artificial lung into which the student can blow to expand the lung, and a resilient chest which the student can compress.

Sensors are provided in the manikin to accurately detect the instantaneous amount of lung expansion and chest compression. An A/D converter converts the analog sensor output signals to digital codes, and inputs them to a compact controller based on an inexpensive microcomputer chip governed by a control program stored in a ROM.

Pushbuttons on the controller's front panel enable the student to select any one of a variety of teaching routines prestored in the microcomputer's ROM. The microcomputer then uses lamps on the panel and a speech synthesizer having prerecorded human speech stored in ROM chips to issue instructions and advice to the student. These are contingent on his performance of the selected routine as detected by the sensors. However, a prestored interrupt routine always enables the student to switch from the current routine to any other or to get an immediate repeat of the last message from the system.

Transducers are provided for simulating a carotid pulse and shallow breathing in the manikin which can be activated by remote control using a wireless transmitter and receiver pair.

The invention is suitable for use in retrofitting "dumb" manikins which are already out in the field, as well for incorporation into new manikin-controller assemblies; a fact which should be taken into account in interpreting the appended claims.

BRIEF DESCRIPTION OF THE DRAWINGS

These and other features of this invention will be best understood by reference to the following detailed description of a preferred embodiment of the invention, taken in conjunction with the accompanying drawings, in which:

FIG. 6A is a cross-section of a first embodiment of a carotid pulse simulator installed in the neck of the manikin of FIG. 1;

FIG. 6B shows a circuit for providing a bipolar driving voltage waveform for activating the motor of the carotid pulse simulator of FIG. 6A;

FIG. 6C is a cross-section of a second embodiment of a carotid pulse simulator for use in the manikin of FIG. 1;

FIG. 6D is a side elevational view of the carotid pulse simulator of FIG. 6C;

FIGS. 17, 17a and 17b are a flow chart for an embodiment of the Chest Compression Rhythm Teaching Routine incorporated in the Control Program of FIG. 11;

FIG. 19 is map showing how voice messages and phrases are stored in memory;

FIG. 21A is a flow chart for an embodiment of the A/D Conversion Subroutine incorporated in the Control Program of FIG. 11, and FIG. 21B is a graph of a typical sensor signal as a function of time;

DETAILED DESCRIPTION

A. System Construction

1. General Construction

Figure 1:
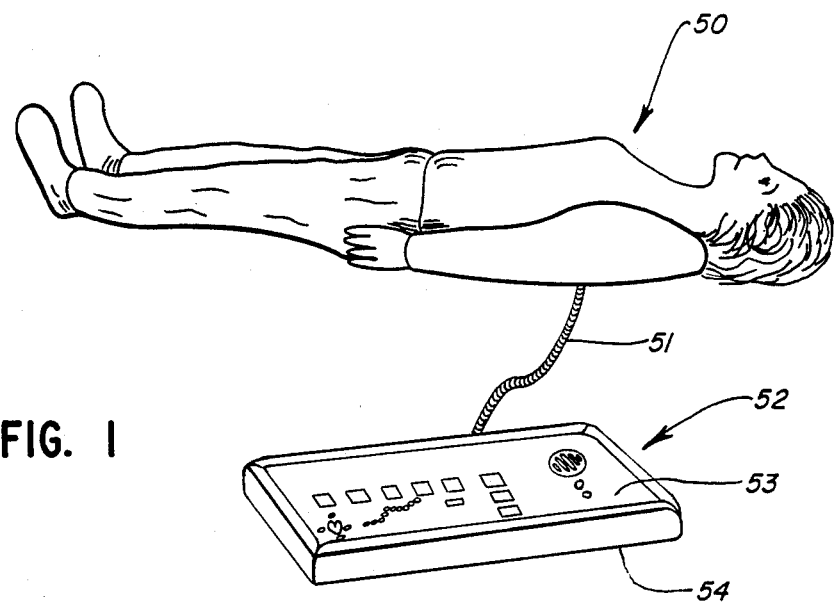
FIG. 1 is a perspective view of an interactive CPR training system including a simulation manikin and a control unit incorporating the principles of the invention.

As shown in FIG. 1, an interactive CPR training system constructed in accordance with the teachings of this invention comprises a simulation manikin 50 coupled by a cable 51 to a control unit 52 comprising a box 54 incorporating a control panel 53. Although control unit 52 is shown separated from the manikin 50, if desired the two may be combined into a single unit. For example, control unit 52 may be mounted in an otherwise unused lower portion of the manikin. Similarly, the electronics for the system may be distributed in any convenient manner between the control unit's box 54 and otherwise unused internal portions of the manikin.

2. Control Panel

Figure 2:
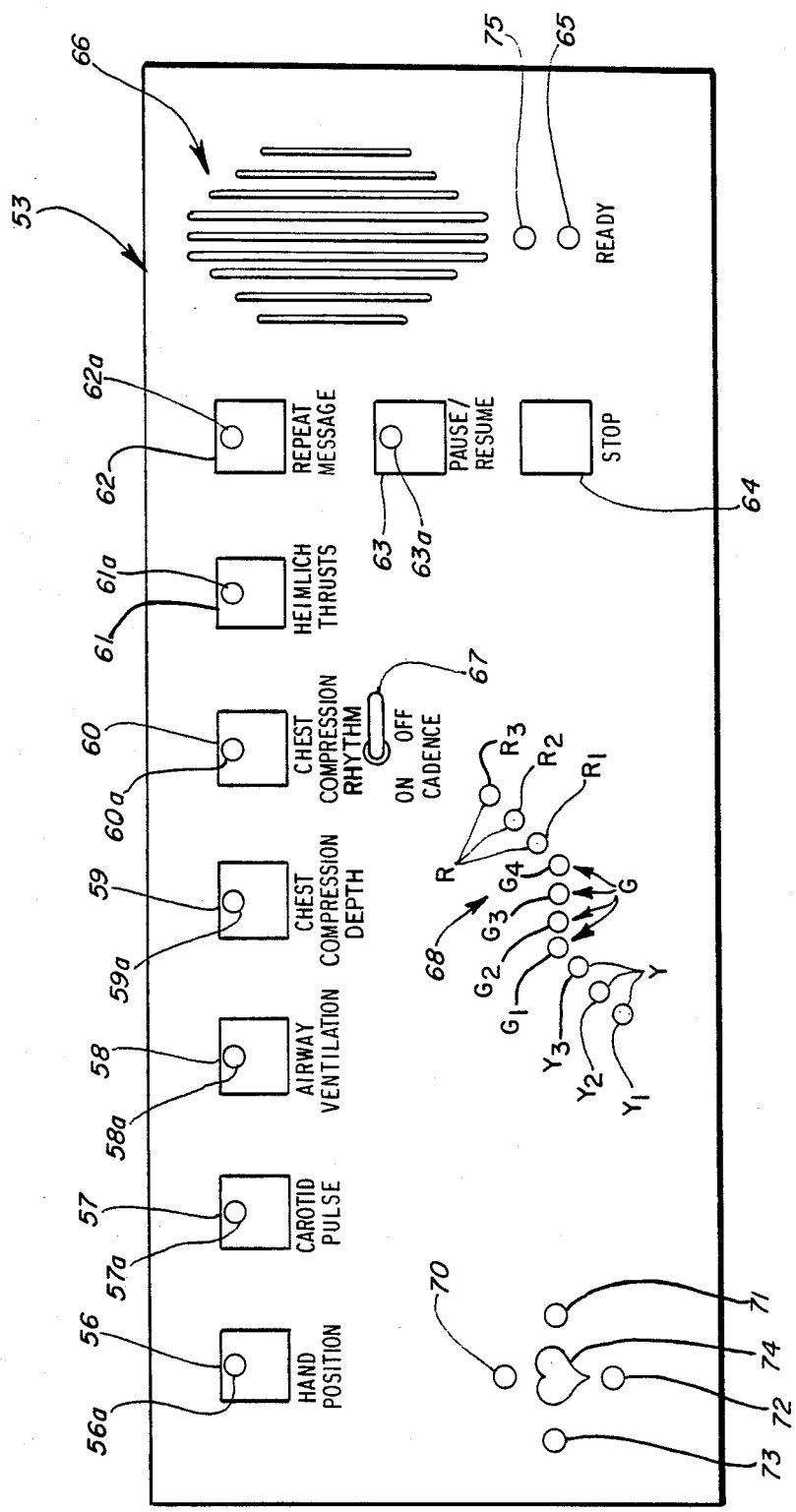
FIG. 2 is a top plan view of a control panel for the training system of FIG. 1.

FIG. 2 shows the control panel 53 in greater detail. The various resuscitation routines taught by the system in conjunction with simulation manikin 50 are chosen by the student, using selection buttons 56 for Hand Position, 57 for Carotid Pulse, 58 for Airway Ventilation, 59 for Chest Compression Depth, 60 for Chest Compression Rhythm, and 61 for Heimlich (Abdominal) Thrusts. An important feature of our invention is that the system is always ready to repeat the most recent message to the student if he or she presses the Repeat Message button 62.

Control panel 53 also includes a Pause/Resume button 63. Pressed once, this button causes the system to pause; pressed again this button causes the system to resume where it left off. If button 63 is pressed once for "Pause", the system will wait a predetermined period, for example four minutes, for the button to be pressed again for "Resume". If the second pressing does not occur within the predetermined period, the system abandons the routine that was "Paused" and resets itself to its standby low power state.

The selection buttons 56–61 for the teaching routines and the Repeat Message 62 and Pause/Resume 63 buttons have corresponding lamps 56a–63a, which may be light-emitting diodes (LED's). A Stop Button 64 causes the current routine being executed to halt and resets the system to its standby low power state.

At certain points in the various operating routines, the system is unable to accept inputs from the student. When the system is ready for student input, it blinks a ready lamp 65 on the control panel 53 of FIG. 2.

The system gives oral advice and coaching to the student via a speaker 66, using prestored messages chosen in context in response to various inputs from the user.

As visual feedback during the ventilation and chest compression training routines, an array 68 of colored LED's indicates the results of the student's efforts to breathe air into the manikin's "lungs" or to "restore circulation" by compressing the manikin's chest. This array consists of three yellow lamps Y1, Y2, Y3 for low readings, four green lamps G1, G2, G3, G4 for medium readings, and three red lamps R1, R2, R3 for high readings. The smallest effort above a certain threshold causes the lowest lamp Y1 to light, and successively larger signals light additional lamps in the order Y2, Y3, G1, G2, G3, G4, R1, R2, R3 until all the lamps are lit.

In the teaching routines this colored lamp array provides important visual feedback to the student: An effort (artificial respiration or chest compression) lighting only the yellow lamps is too low. An effort lighting one or more of the green lamps but none of the red lamps is good, an acceptable performance. But an effort that lights one or more of the red lamps is too much, indicating danger to the victim represented by the manikin.

During efforts to compress the manikin's chest, the student's hand position must be in a critical location corresponding to the lower half of the victim's sternum. As visual feedback, a set of lamps 70, 71, 72, 73 arranged around a stylized heart symbol 74 all remain lit if the hand position during compression is correct. If a lamp goes off, it indicates the hand position on the manikin is too far in a direction indicated by the turned off lamp relative to the center of the heart symbol. This allows the student to note his error and correct his hand position accordingly until all lamps are lit during compression.

In cardiopulmonary resuscitation it is important for the rescuer to periodically check to determine if the victim's breathing or heartbeat has resumed. Button 57 enables a training routine in which the student can practice locating and detecting a carotid pulse in the neck area of the manikin. As a more realistic simulation, the system provides for an instructor to secretly turn on in the manikin a simulation of shallow breathing or carotid pulse or both by means of an wireless signal to the control unit 52. With this objective in mind, the control panel 53 can also include a receiver sensor 75 in a convenient location, such as adjacent the Ready lamp 65. If, for example, an infrared beam is used for the wireless signal from the instructor, sensor 75 will be an infrared detector.

Control panel 53 also includes a cadence switch 67 to turn on a 1.5 Hz audible cadence beat to guide the student in performing a rhythmic series of chest compressions to restore blood circulation.

3. General Teaching Sequence

Figure 3:
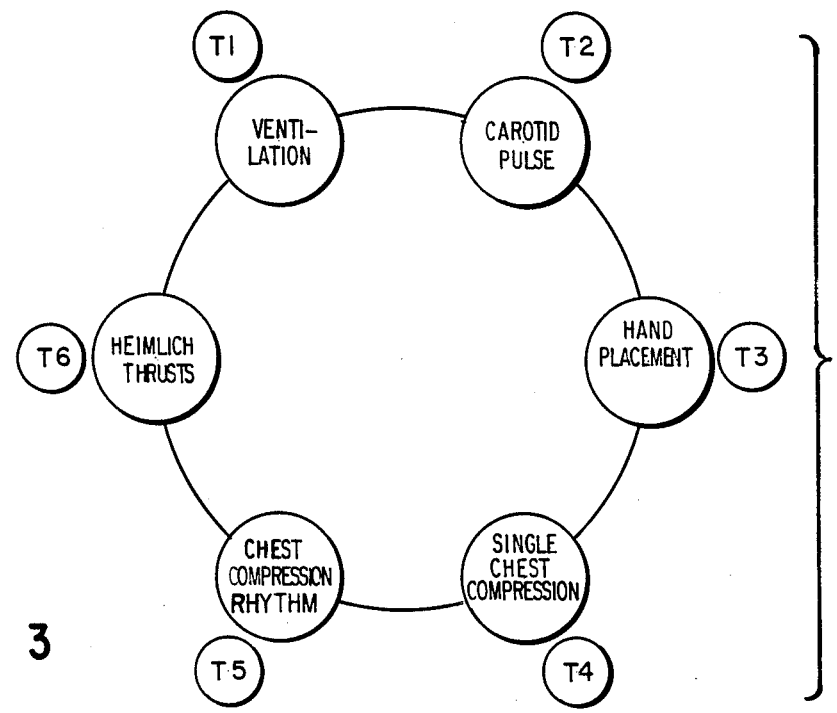
FIG. 3 is a flow diagram of a typical training sequence achieved by the training system of FIG. 1.

FIG. 3 shows a flow diagram of a typical training sequence enabled by the training system of FIG. 1, in which the student can proceed in the following sequence: Ventilation of the Airway (T1), Carotid Pulse Detection (T2), Hand Placement for Chest Compression (T3), Single Chest Compressions (T4), Chest Compressions in Rhythm (T5), and Heimlich Abdominal Thrusts to Remove Airway Obstructions (T6).

The system does not force the student to pursue the training in this sequence. Instead, the student is permitted to select any training routine at a time using the selection buttons 56–61 on the control panel of FIG. 2. However, like a good coach, as the student completes one training routine (e.g. Ventilation), the system vocally suggests the next appropriate sequence (Carotid Pulse), and for a brief interval even blinks the corresponding selection button for the suggested sequence. For example, at the close of the ventilation training the system plays the stored message "Excellent ventilation. If you feel confident, you should now practice checking the carotid pulse. If you don't, try giving two breaths again," and blinks the selection button lamp 57a of FIG. 2 located on the carotid pulse selection button 57.

4. Control Unit

Figure 4:
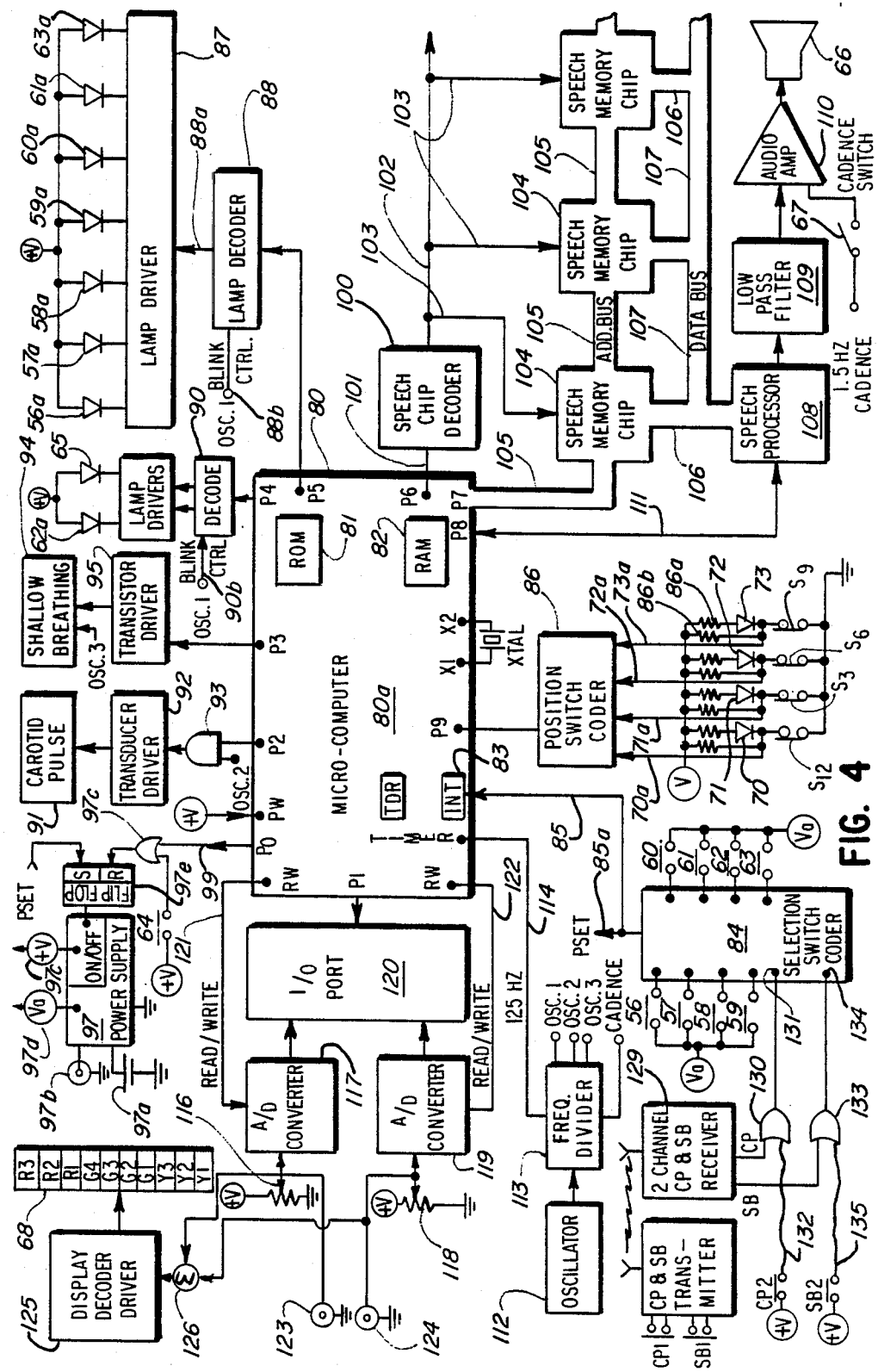
FIG. 4 is a functional block diagram of the control unit shown in FIG. 1.

FIG. 4 shows a functional block diagram of control unit 52 of FIG. 1. At the heart of control unit 52 is a microcontroller 80. It is a feature of our invention that while the monitoring, feedback, and vocal coaching of the student is a sophisticated simulation of a human coach, all this can be accomplished with relatively modest computational power, cost and size. While control unit 52 could be implemented by a suitably programmed personal computer or a minicomputer or the like, the necessary associated input/output circuits alone would be at least as complicated and expensive as our microcontroller-based system. Instead, our invention can be satisfactorily realized based on a much simpler single-chip microcomputer For example, microcontroller 80 can be a single chip microcomputer 80a such as the 8 bit HD637B05V0C microcomputer unit (MCU) available from Hitachi America, Ltd. of San Jose, Calif. Such a microcomputer 80a has a 4 kilobyte ROM (read only memory) 81 for holding a prestored control program and its associated prestored data. It also has a 192-byte RAM (random access memory) 82 which can be used as a scratchpad memory. The microcomputer's basic clock frequency can be set at a convenient frequency, such as 8.0 MHz (megahertz) by a suitable external crystal XTAL attached to terminals X1 and X2. To enable battery operation, the microcomputer unit is made with complementary metal-oxide semiconductor (CMOS) integrated circuits which have low power consumption.

FIG. 4 shows a number of peripheral chips used with microcomputer chip 80a, primarily as interface (input/output) chips. It is feasible, however, to use a more powerful microcomputer chip that will incorporate many of the functions of these external circuits. For example, Hitachi America, Ltd. also makes the HD63705ZO microcomputer unit that incorporates 8 channels with built-in A/D converters of 8-bit accuracy.

To enable it to respond to external control inputs, such as the selection buttons 56–63 on the control panel 53 of FIG. 2, microcomputer 80a has an interrupt port (INT) 83 for an external hardware interrupt. These selection buttons 56–63 provide inputs to a switch coder 84. Each time a selection button is pushed, switch coder 84 sends a coded interrupt signal on line 85 to interrupt port 83. The coded interrupt indicates which of the selection buttons has been pushed. The microcomputer 80a then interrupts its current task, storing internal register information in a stack (not shown) so it can return to it later. The microcomputer 80a responds to the interrupt by means of an Interrupt Routine (FIG. 12) that implements the function corresponding to the button pushed.

Microcomputer 80a has an eight-bit timer on board which can be configured to use an external timer clock input received at a TIMER input. The on-board timer in microcomputer 80a includes an eight-bit timer data register TDR, which contains the current value of the on-board timer.

Microcomputer 80a also has various ports P1–P8 which it uses for input/output of data or control signals to external circuits and devices. A coded signal output at port P5 is used to control the indicator lamps on control panel 53 of FIG. 2. A lamp decoder circuit 88 receives the coded output of port P5 and uses it to determine which lamps are to be lit. Lamp decoder circuit 88 sends control signals to a lamp driver circuit 87 via line 88a to switch on or off LED's 56a (HAND POSITION), 57a (CAROTID PULSE), 58a (AIRWAY VENTILATION), 59a (CHEST COMPRESSION DEPTH), 60a (CHEST COMPRESSION RHYTHM), 61a (HEIMLICH THRUSTS), and 63a (PAUSE/RESUME) on control panel 53. To provide for blinking of the lamps, an oscillator signal OSC1 is fed to lamp decoder 88 via blink control line 88b.

In a similar manner, the output at port P4 is used to control the panel lamps 62a (REPEAT MESSAGE) and 65 (READY) via a lamp decoder 90 and a lamp driver 89. To provide for blinking of the lamps 62a and 65, the oscillator signal OSC1 is also fed to lamp decoder 90 via blink control line 90b.

A port P2 is used to control a carotid pulse transducer 91 for simulating a carotid pulse in the manikin's neck. The two inputs of an AND gate 93 receive respectively the output of port P2 and a digital oscillator signal OSC2 of about 1 pulse per second (simulating the carotid pulse rate). The output of AND gate 93 is inputted as a control signal to a transducer driver circuit 92 whose output drives carotid pulse transducer 91.

Similarly, a port P3 is used to control a shallow breathing transducer 94 to enable the manikin to simulate a victim's shallow breathing. The output of port P3 is input as a control signal to a transistor driver 95 which drives shallow breathing transducer 94. An oscillator signal OSC3 having a period of about 4 seconds (simulating a breath every four seconds) is also input to shallow breathing transducer 94.

Electrical power for operating the system is provided by a power supply 97 that outputs supply voltage +V at 97c. It is an important feature of the invention that its circuits and auxiliary devices are small and efficient enough that a compact low-voltage battery 97a, such as six "D" size 1.5 volt dry cells, can provide the necessary electrical energy for the power supply. This permits the manikin to be conveniently portable. However, the power supply can also include an input jack 97b for an external DC supply voltage, such as can be provided by a conventional AC adapter (not shown) that depends on a 110 V. AC line cord for power.

Power supply 97 outputs a standby voltage $V_a$ at 97d and a main voltage +V at 97c. Standby voltage $V_a$ is always available if battery 97a is connected or there is a DC voltage input at 97b from an AC adapter. Standby voltage $V_a$ powers those few circuits which must always be able to respond to the pressing of a selection button, such as switch coder 84 and a power supply control flip-flop 97e.

The main voltage +V is turned on to run the teaching routines and turned off for power saving. The output of flip-flop 97e is inputted to power supply 97 so that the state of flip-flop 97e controls whether main voltage +V is on or off.

When the output of flip-flop 97e is a logical 1 (high), main voltage +V is turned on. This is done by inputting a signal that is a logical 1 to the S (SET) input of flip-flop 97e. Pressing any of program switches 56–63 causes selection switch coder 84 to output a power up PSET signal that is a logical 1 on line 85a to input S of flip-flop 97e. This puts flip-flop 97e in its 1 state, turning on main voltage +V for microcomputer 80a and its peripheral circuits. Pressing any of selector switches 56–63 also causes selection switch coder 84 to send an interrupt signal on line 85 to microcomputer 80a.

Once provided with the main voltage +V, microcomputer 80a automatically initializes itself and then services the interrupt signal from selection switch coder 84 to provide the teaching routine corresponding to the switch (56–63) which has been pressed.

Inputting a signal that is a logical 1 to the R (RESET) input of flip-flop 97e causes the flip-flop to output a logical 0 (low), turning off main voltage +V. The R input of flip-flop 97e is fed by the output of an OR gate 97f having two inputs, one from a power off port P0 of microcomputer 80a and the other from the STOP button 64 on control panel 53 of FIG. 2. If either of these two inputs is a logical 1, OR gate 97f outputs a logical 1, resetting flip-flop 97e to turn off main voltage +V, putting the system in its standby low power state.

Thus pressing the STOP button 64 on control panel 53 stops the system by turning off the main voltage but leaves it in the standby state. Normally, pressing the PAUSE/RESUME button on control panel 53 once causes the system to temporarily halt its present routine and wait a preset period for the button to be pressed again for RESUME. However, if the preset period, for example four minutes, is exceeded, microcomputer 80a outputs a logical 1 via power-off port P0, line 99, and OR gate 97f to turn off the main voltage +V.

Ports P6, P7 and P8 are used to provide a simulated speech output including coaching instructions to the student. As will be explained in more detail below, all messages to the student are composed of short, prestored phrases. Therefore, a message is reproduced by sequentially synthesizing each of the prestored phrases making up the message. The real voice sounds which make up the phrases sampled, and sample numbers from which the phrases can be synthesized by a speech processor 108 have been stored as bytes in speech memory chips.

To reproduce a prestored phrase, port P6 is used to output a signal on line 101 to a speech chip decoder 100 that sends an enable signal to the speech memory chip which holds the sample numbers for that phrase. Then port P7 is used to output an address on address bus 105. The contents at that address in the enabled speech chip are read out via a data bus 107 to speech processor 108. After synthesizing the corresponding sound from contents of that address, speech processor 108 sends a signal to port P8 of microcomputer 80a via line 111 to indicate that it is ready to receive the next sample number. The microcomputer 80a responds by outputting the next address on address bus 105. This process is repeated until all stored sounds of the phrase have been synthesized.

The synthesized output of speech processor 108 is smoothed by a low-pass filter 109 having a high frequency cutoff of about 4 kHz. The smooth audio output of low-pass filter 109 is amplified by audio amplifier 110, which drives the output speaker 66 on control panel 53 of FIG. 2.

To assist the student in developing the proper rhythm for chest compressions, a cadence beat is provided by a 1.5 Hz cadence signal. A cadence switch 67 on the control panel 53 connects this signal to audio amplifier 110 for audio output by speaker 66.

An external oscillator 112 is provided to generate a reference clock for the relatively low frequency signals. The output frequency of this oscillator is divided by frequency divider circuit 113. That circuit 113 has outputs for the various reference input signals OSC1 (indicator lamp flashing), OSC2 (carotid pulse), OSC3 (shallow breathing), as well as the 1.5 Hz cadence beat, and a 125 Hz timer clock signal that is inputted to microcomputer 80a at a TIMER terminal.

The normally closed switches S12, S3, S6, S9 shown in FIG. 4 are located on the manikin's chest to detect of the student's hand position during chest compression exercises. As will be discussed below in more detail in connection with FIGS. 8A–8F, a misplaced hand will open one or more of these switches. Each of the switches has one side connected to ground and the other side connected to a corresponding LED 70, 71, 72, 73 on the control panel 53 of FIG. 2. Each of the LED's is connected to the supply voltage +V via a respective load limiting resistor 86a. As visual feedback to the student, when a switch S12, S3, S6, S9 is closed, its corresponding LED 70, 71, 72, 73 will be ON, and when the switch is open, the corresponding LED will be OFF.

The non-grounded side of each of the switches S12, S3, S6, S9 has a respective output line 70a, 71a, 72a, 73a connected to a position switch coder 86 and through a respective load resistor 86b to the supply voltage. When a switch S12, S3, S6, S9 is closed, the voltage on the corresponding output line 70a, 71a, 72a, 73a will be a logical 0 (ground), and when the switch is open the output line voltage will be a logical 1 (high). Position switch coder 86 encodes the state of each of the switches and inputs the coded information to microcomputer 80a via port P9.

The manikin is fitted with position sensors for measuring the student's efforts to compress the manikin's chest and to ventilate the manikin's artificial lungs. In FIG. 4 a chest compression sensor 116 is shown as a potentiometer whose main resistive element is connected between ground and supply voltage +V, and whose output slider is mechanically linked to move as the chest is compressed. The output slider voltage is inputted to an A/D (analog to digital) converter 117 when a suitable READ pulse is received on READ/WRITE line 121. The digitized output of A/D converter 117 is inputted to port P1 of microcomputer 80a via a multiplexing I/O port 120.

Similarly, a ventilation sensor 118 is shown as a potentiometer whose main resistive element is connected between ground and supply voltage +V, and whose output slider is mechanically linked to move as air is blown into the manikin's artificial lungs via a mouth opening of the manikin.

The output slider voltage is inputted to a corresponding A/D converter 119 when a suitable READ pulse is received on READ/WRITE line 122. The digitized output of A/D converter 119 is inputted to multiplexing I/O port 120. By sending suitable control signals to the multiplexing I/O port via port P1, microcomputer 80a can read in either the digitized signal from the chest compression sensor 116 or the digitized signal from the ventilation sensor 118.

The slider outputs of the chest compression sensor and ventilation sensor are also outputted as analog signals to output jacks 123 and 124 respectively, which can be used to attach a strip chart recorder or other device for recording or monitoring the student's efforts.

During ventilation and chest compression training routines the LED array 68 on the control panel 53 of FIG. 2 provides visual feedback to the student of the magnitude of his or her efforts. This LED array consists of three yellow lamps Y1, Y2, Y3 for the lowest readings (student's efforts too weak or shallow to be effective), four green lamps G1, G2, G3, G4 for the medium readings (student's efforts acceptable), and three red lamps R1, R2, R3 for the high readings (student's efforts too strong, i.e. dangerous to victim). The smallest effort above a threshold causes the lowest lamp Y1 to light, and successively larger signals light additional lamps in the order Y2, Y3, G1, G2, G3, G4, R1, R2, R3 until all the lamps are lit. LED array 68 can be driven by a commercially available display decoder driver circuit used in a bar mode that increases the number of LED'S lit in proportion to the magnitude of the signal input received by it. For example, National Semiconductor's LED dot/bar generator chip LM3914 can be used for this circuit.

Because the student will not be attempting to compress the manikin's chest and ventilate the manikin's lungs simultaneously, the outputs of the chest compression and ventilation sensors may be visually displayed with a single LED array 68.

The chest compression sensor 116 and the ventilation sensor 118 are each adjusted to give a zero output in the "inactive or default position" corresponding to no activity by the student. The analog signals from chest compression sensor 116 and ventilation sensor 118 are added together by an adder circuit 126. The output (sum) signal of adder 126 is proportional to the magnitude of the active sensor, there being substantially no output contribution from the inactive sensor. The output of adder 126 is inputted to the display decoder driver 125 to drive the common LED array 68.

A rescuer giving cardiopulmonary resuscitation must regularly check for and be alert to whether the victim exhibits a carotid pulse or shallow breathing. The control panel 53 provides a selection button to practice sensing the carotid pulse in the manikin's neck. But an important element of realism is added by enabling the instructor to surreptitiously switch the carotid pulse and shallow breathing transducers on and off by remote control without warning. Additional control inputs 131 (to activate the carotid pulse transducer 91) and 134 (to activate the shallow breathing transducer 94) are provided on selection switch coder 84 for this purpose. Selection switch coder 84 treats control inputs 131 and 134 as if they were additional selector switch inputs for sending a coded interrupt to microcomputer 80a to enable the carotid pulse and shallow breathing transducers. If input 131 or 134 is a logical 1 (voltage high), the corresponding transducer is enabled by microcomputer 80a via the corresponding port P2 or P3. If input 131 or 134 is a logical 0 (voltage low), the corresponding transducer is not enabled.

The remote control can be by means of a two-channel wireless transmitter 128 that can signal to a matching receiver 129 the logical state desired for two receiver outputs, SB (shallow breathing) and CP (carotid pulse). Device controllers in the form of matching sets of transmitter and receiver circuits that work with infrared or ultrasonic emitters and detectors are commercially available for this purpose.

For example, Motorola Semiconductor Products of Schaumburg, Ill. makes a transmitter (MC14457) and receiver (MC14458) pair of CMOS chips designed for either infrared or ultrasonic ON/OFF remote control of up to 16 channels. If infrared signals are used, the transmitter circuit 128 receives the instructor's selection of the carotid pulse or shallow breathing transducers by means of corresponding selection buttons CP1 and SB1. Transmitter circuit 128 then encodes these choices and transmits them by modulating an output LED that emits an infrared beam. The matching receiver is provided with a receiving photodiode detector sensitive to infrared, whose detected signal is demodulated to determine the desired state of corresponding outputs CP and SB. Similarly, if ultrasonic signals are used, transmitter circuit 128 modulates an ultrasonic output transducer and matching receiver circuit 129 demodulates the output signal of an ultrasonic microphone detector.

The remote control can also be by means of control wires 132 and 135 to remote locations where the instructor can actuate corresponding pushbuttons CP2 and SB2 to send logical 1 signals for the carotid pulse or shallow breathing routines respectively.

In FIG. 4 both wireless and direct wire remote control are provided for. The two inputs of an OR gate 130 respectively receive the output CP of receiver 129 and the signal on wire 132 from pushbutton CP2. The output of OR gate 130 is inputted as a carotid pulse transducer control signal to input 131 of selection switch coder 84. Thus, if wireless output CP or signal wire 132 is a logical 1, OR gate 130 will output a logical 1 to input 131 to signal microcomputer 80a to activate the carotid pulse transducer 91.

Similarly, the inputs of an OR gate 133 receive the outputs SB of receiver 129 and the signal on wire 135 from pushbutton SB2. If wireless output SB or signal wire 135 is a logical 1, OR gate 133 will output a logical 1 to input 134 to signal microcomputer 80a to activate the shallow breathing transducer 94.

5. Shallow Breathing Simulator

Figure 5:
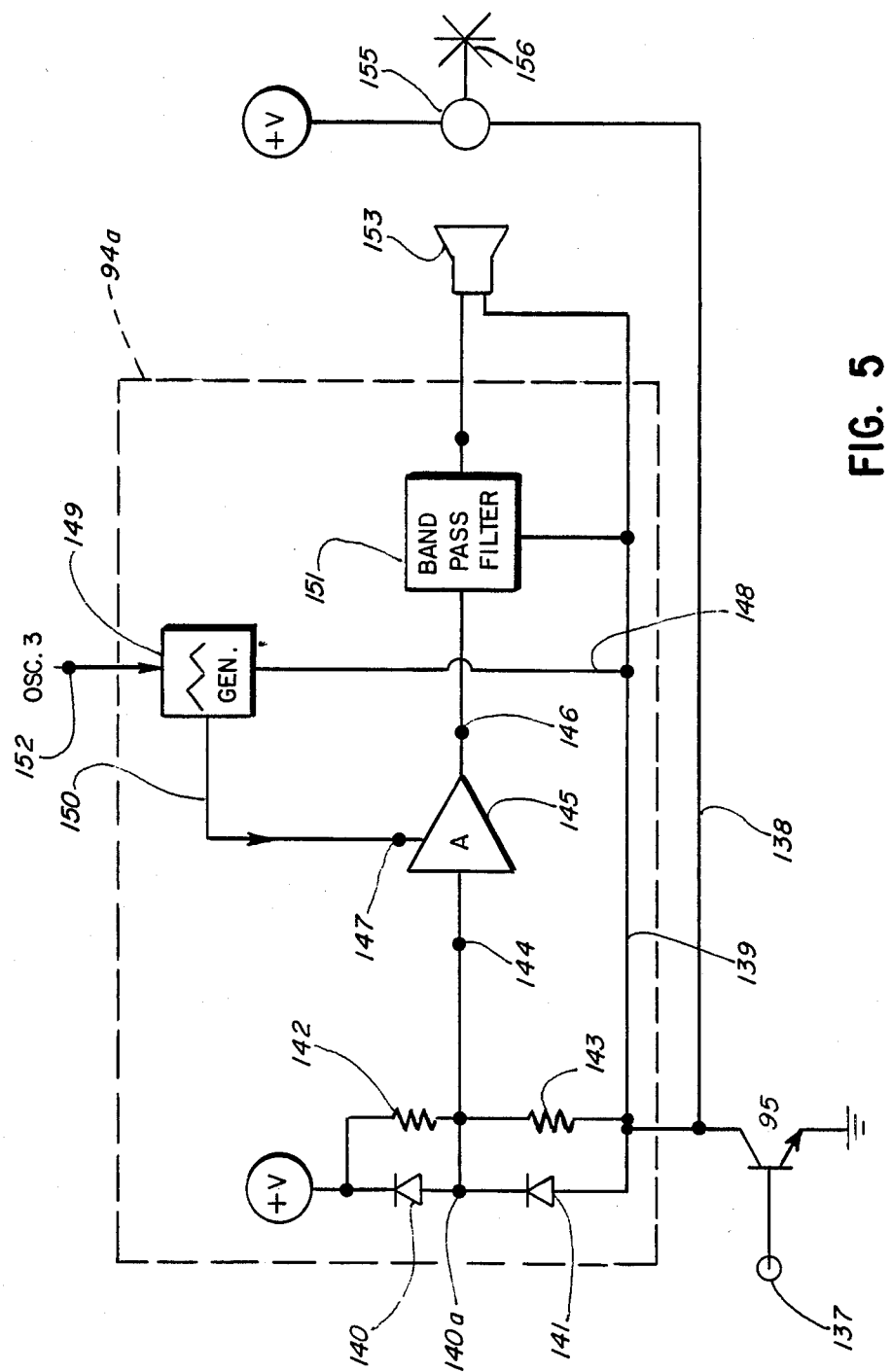
FIG. 5 is a simplified schematic of a shallow breathing simulator for use in the system of FIG. 1.

FIG. 5 shows a detailed example of the shallow breathing transducer 94 and transistor driver 95 of FIG. 4. Transistor driver 95 is a switching transistor having its emitter connected to ground receives at its base input 137 an enabling high signal (logical 1) from port P3 of the microcomputer whenever the operating program determines that the shallow breathing simulation is needed or has been requested (e.g., by instructor intervention). This switches transistor 95 ON, so that a circuit line 139 of a transducer driving circuit 94a is essentially at ground, enabling the driving circuit. Driving circuit 94a is adapted to simulate a "breathing" waveform to drive a miniature output speaker 153 located in the manikin's throat area.

Driving circuit 94a produces an amplitude-modulated random or white noise signal having an amplitude envelope that is a periodic triangular shaped wave with a period of about four seconds (one shallow breath every four seconds). To generate random noise, two reverse-biased diodes 140 and 141 are connected in series between the main voltage $+V$ and grounded line 139 to create random "shot noise" at their connection point 140a. This random noise is input at 144 to an operational transconductance amplifier 145, such as LM 13600 made by National Semiconductor, which provides for a voltage controlled gain input 147. The output of the amplifier at 146 is passed through a bandpass filter 151, such as National Semiconductor's MF5CN100 filter, having a bandpass of about 1 to 5 kHz, and then drives miniature speaker 153.

The gain of amplifier 145 is modulated at gain input 147 by a voltage output at 150 from a triangular waveform generator 149 having a period of 4 seconds. In the functional block diagram of FIG. 4, frequency divider 113 provides a suitable 0.25 Hz low-frequency clock signal OSC3 which can be inputted to triangular waveform generator 149 at 152 to regulate its 4-second triangular periodic waveform.

Each new four-second period of shallow breathing simulation begins with the gain of amplifier 145 set to zero, after which the gain is increased steadily to raise the volume of the white noise. The volume peaks after two seconds, and then the gain of amplifier 145 is steadily reduced to zero in the remaining two seconds of the period, causing the white noise sound to fade away. Thus, the volume of the white noise passed to speaker 153 via bandpass filter 151 rises and falls during the four second period of the triangular waveform, simulating the sound of breathing.

If desired, the movement of air from the mouth and nose during breathing can be simulated by providing a small fan 156 powered by a miniature DC fan motor 155 in the manikin's airway passage area. One terminal of DC motor 155 is attached to the main supply voltage $+V$ and the other terminal is attached to a line 138 wired to the collector of switching transistor 95. Whenever transistor 95 is turned ON by the input at base 137, line 138 is essentially grounded, turning on motor 155 to drive fan 156.

6. Carotid Pulse Simulator

A person performing cardiopulmonary resuscitation must initially determine if the victim's heart has stopped (cardiac arrest), and during the procedure to restore circulation by chest compressions must periodically check for a return of the heart function. This is done by checking the victim's pulse, preferably the carotid pulse in one of the arteries found on either side of the neck. This is done by placing the tips of the index and middle fingers at the correct pulse location at the side of the victim's neck.

FIG. 6A shows a first embodiment of a carotid pulse simulator 91 that can be suitably located in the hollow area 161 of the manikin's neck 160. The neck is a tubular structure enclosed by a cylindrical wall 162 of plastic "skin". A layer of resilient material 163, such as foam rubber, is attached, by adhesive or the like, to the inside face of neck wall 162. A small DC motor 164 is then axially mounted to the front of neck wall 162 with its drive shaft 164a parallel to the axis 160a of the manikin's neck. The resilient material 163 is used to provide a cushion between motor 164 and neck wall 162. For example, the motor can be attached to the resilient material by a suitable adhesive.

A pair of linkages 165 are symmetrically mounted at approximately a right angle to each other on the motor shaft 164a, and are driven by it. Mounted to each linkage at approximately a right angle is an outwardly directed radial beater arm 166 that rests against the resilient material. Each time DC motor 164 is driven in a clockwise direction, the beater arm 166 on the right impinges on resilient material 163 lining the manikin's neck wall 162. This delivers an impulse of force F to the neck wall in the "carotid" region that can be felt by the student's fingers as a simulated beat of a carotid pulse on that side of the neck. Similarly, when motor 164 is driven counterclockwise, beater arm 166 on the left impinges on material 163, delivering an impulse F to simulate one beat of a carotid pulse on the left side The resilient material 163 is stretched during the impulse. When the impulse ends, the resilient material's restoring force returns the beater arm to its initial position.

FIG. 6B shows a bridge circuit 170 which provides a bipolar driving voltage waveform for activating the motor of the carotid pulse simulator of FIG. 6A. On one side of the bridge circuit, electronically controlled normally open, single-pole, double-throw switches CS1 and CS2, which preferably are switching transistors, are connected in series between the main voltage +V and ground. Similar electronically controlled switches CS3 and CS4 are connected in series between the main voltage +V and ground on the other side of the bridge circuit. The DC motor 164 for simulating the carotid pulse is wired between a first terminal 171 joining switches CS1 and CS2 and a second terminal 172 joining CS3 and CS4.

To turn DC motor 164 in the clockwise direction, only switches CS1 and CS4 are closed by a drive voltage on terminals A just long enough to activate the motor to simulate a carotid pulse on one side of the neck. Then drive voltage A terminates, so that switches CS1 and CS4 are allowed to open, and only switches CS2 and CS3 are closed by a drive voltage on terminals B just long enough make the motor turn counterclockwise to simulate a carotid pulse on the other side. In the functional block diagram of FIG. 4, frequency divider 113 provides a suitable low-frequency bipolar clock signal OSC2 of about 0.65–0.85 Hz which can be used as a clock for controlling the switch pairs CS1 and CS4 on the one side, and CS3 and CS4 on the other.

FIGS. 6C and 6D show a second embodiment of a carotid pulse simulator 91b that can be transversely mounted in the manikin's neck 160 and driven by voltage pulses of a single polarity. As in the first embodiment of FIG. 6A, the neck wall 162 is lined with a resilient material 174, but only in the regions where the pulses are to be simulated. A motor 176 is transversely affixed at an offset $D_O$ to the neck wall 162 by a base support 175, which may also be of resilient material. Motor 176 is traversed by a rotatable shaft 177 that supports a perpendicular leg 178 at each end. The other end of each leg 178 is joined to an elongated beater foot 179 whose long axis is substantially parallel to the axis 160a of the manikin's neck. Each foot 179 nestles in the resilient material 174.

As can be seen in FIG. 6D, when the motor is pulsed in a single direction (counterclockwise, as indicated by the circular arrow C) each beater foot 179 delivers an impulse of force F to its adjacent area of the neck wall 160. Therefore, with this embodiment a bipolar driving voltage waveform is unnecessary, and the bridge circuit 170 of FIG. 6B need not be used. Instead, the transducer driver 92 shown in FIG. 4 can be a relatively simple switching transistor turned ON and OFF by the output of AND gate 93 to drive motor 176 whenever a beat of the carotid pulse is called for. The other input of AND gate 93 is the 0.65–0.85 Hz clock signal OSC2 from frequency divider 113 to provide the beat of the pulse The resilient material 174 restores the beater feet 179 to their initial positions during the interval between pulses.

7. Ventilation Sensor

Figure 7A:
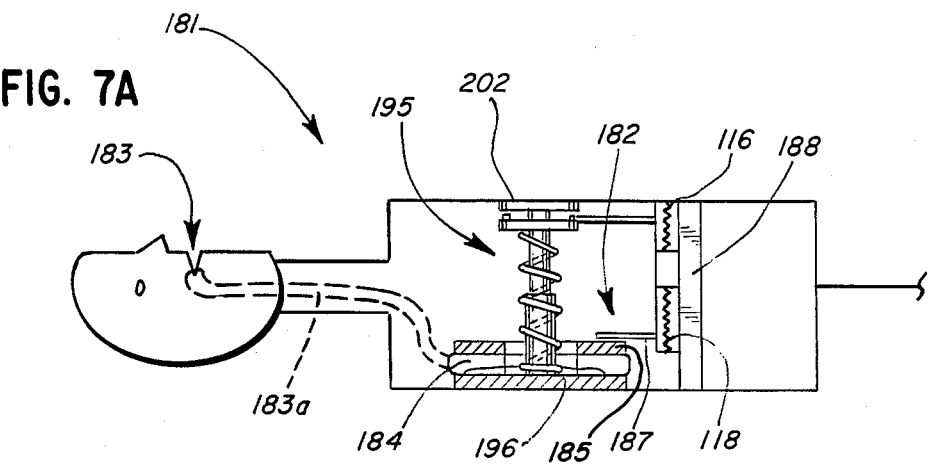
FIG. 7A is a simplified cross-section of a manikin fitted with a ventilation sensor and a combined hand position and chest compression sensor, seen at a time when there is little air in the ventilation sensor.

FIG. 7A shows a simplified cross-section of a manikin 181 fitted with a ventilation sensor 182 and a combined hand position and chest compression sensor 195, seen at a time when the manikin's artificial lungs are deflated. Ventilation sensor 182 has an opening at the manikin's mouth 183 into which the student can blow to inflate the manikin's artificial lungs. The air blown in at the mouth 183 is conveyed by an airway tube 183a, which may be made of plastic, to an inner-tube shaped resilient sac or artificial lung 184 which inflates (compare FIG. 7A with FIG. 7B) as air is forced into it via tube 183a. Artificial lung 184 can be made of rubber or flexible plastic and is toroidally shaped to provide a central passageway 184a for components of chest compression sensor 195 which will be described in more detail below.

Artificial lung 184 is sandwiched between a base plate 196 and a flat lung plate 185 which is attached to the top of plastic lung 184. Plates 196 and 185 are made of plastic or other suitable rigid material. Lung plate 185 also has a central opening 186 to provide for passage of components of the chest compression sensor. As air blown into the manikin's mouth 183 causes lung 184 to inflate, it pushes up against lung plate 185.

Figure 7B:
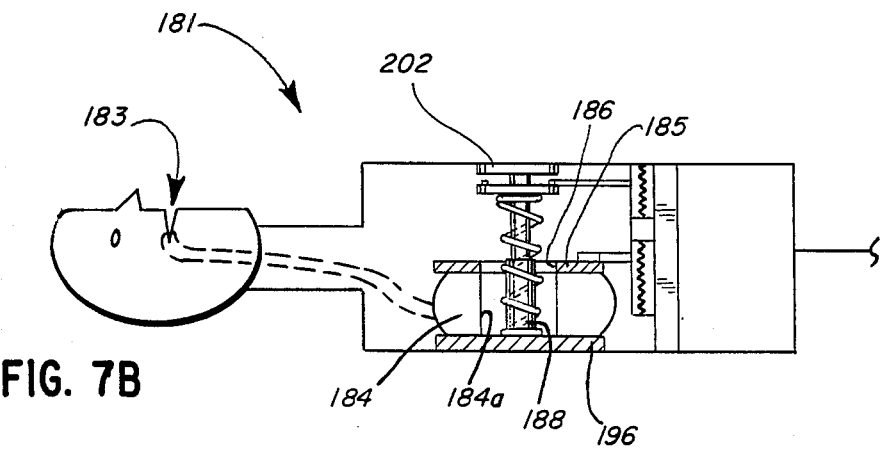
FIG. 7B is a simplified cross-section of the manikin of FIG. 7A seen at a time when air has been blown into the ventilation sensor.
Figure 7C:
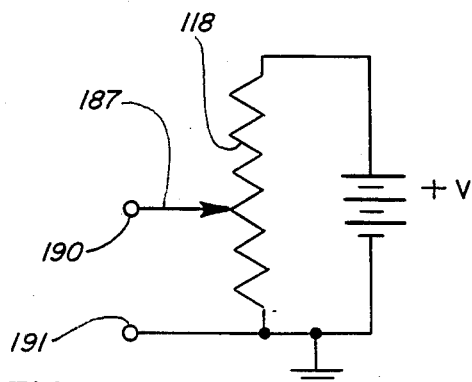
FIG. 7C is a circuit diagram of an analog detection circuit used with the ventilation sensor or chest compression depth sensor shown in FIGS. 7A and 7B.

Adjacent the lung 184 is a vertical support 183 on which is mounted a potentiometer 118 for measuring the excursion of lung plate 185 to determine how much air has been blown into lung 184. Slide potentiometer 118 has a wiper arm 187 mechanically fixed to lung plate 185 to move with the plate. FIG. 7C shows a circuit diagram of an analog detection circuit used with the ventilation sensor of FIGS. 7A and 7B. Potentiometer 118 is connected between the main voltage +V and ground, and its wiper arm 187 provides an output voltage at 190 proportional to the relative position of wiper arm 187 in its stroke along the resistor of the potentiometer. Thus, inflation of the manikin's lungs causes a change in position of lung plate 185 that is reflected in the output of potentiometer 118, providing a means by which the amount of air in artificial lung 184 can be determined.

The purpose of potentiometer 118 is to sense the position of lungplate 185. With suitable adjustments some other type of position sensor, such as a Hall effect sensor, can be substituted for potentiometer 118. Such a substitution can also be made for potentiometer 116 which is used to sense position in chest compression sensor 195, as discussed below.

8. Hand Position and Chest Compression Sensor

Figure 8A:
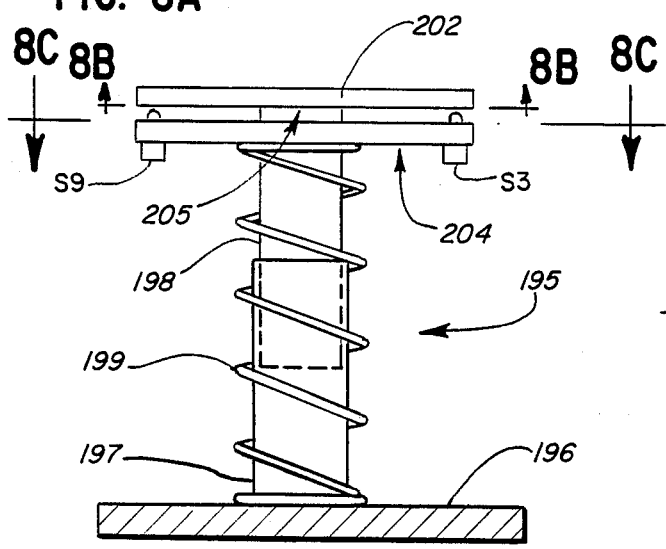
FIG. 8A is a simplified cross-section of a combined hand position and chest compression sensor for use with the manikin of FIGS. 7A and 7B.

In performing cardiopulmonary resuscitation, if a carotid pulse check indicates that the victim's heart has stopped, circulation is restored by external cardiac compression, i.e. rhythmically pressing on the victim's chest. FIGS. 7A, 7B and 8A show a simplified view of a combined hand position and chest compression sensor 195 for installation in the chest area of the manikin. Sensor 195 has a base plate 196 that supports a lower guide tube 197 into which is slidably telescoped an upper guide tube 198 carrying a circular switchplate 204 at its upper end. A coil compression spring 199 is fitted around upper and lower guide tubes 197, 198, the spring's expansion being constrained by the inner opposing faces of base plate 196 and switchplate 204. Resting on a raised circular protrusion 205 in the center of the upper face of switchplate 204 is a circular handplate 202 which may be attached to the inside surface of the plastic skin of the manikin's chest (see FIG. 7A). Handplate 202 and switchplate 204 are each formed of a suitable rigid material, such as plastic or metal, about 4 inches in diameter and a quarter of an inch thick, and are concentrically aligned with guide tubes 197, 198. Circular protrusion 205 is about one inch in diameter and protrudes about one eighth of an inch above the upper face of switchplate 204.

When there is no external downward force on handplate 202, spring 199 pushes switchplate 204 (and its handplate 202) upward until it rests against a stop (not shown). Pushing down on handplate 202 forces upper guide tube 198 into lower guide tube 197 while compressing spring 199 between plates 196 and 204. This simulates the resilient resistance the student would feel when pressing on a real victim's chest. By measuring the excursion of switchplate 204 from its rest position, the amount of compression applied to manikin's chest by the student at any time may be determined. For this measurement a potentiometer 116 is mounted in the manikin on a vertical support 188 and a wiper arm of potentiometer 116 is mechanically fixed to switchplate 204 (see FIGS. 7A and 8D) to move with the switchplate.

Figure 8E:
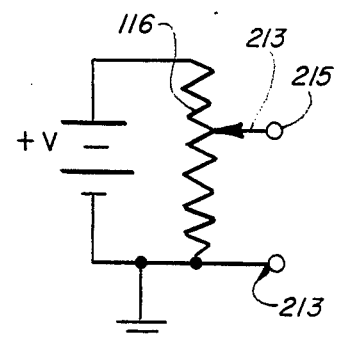
FIG. 8E is a circuit diagram of an analog detection circuit used with the detecting potentiometer of FIG. 8D.
Figure 8B:
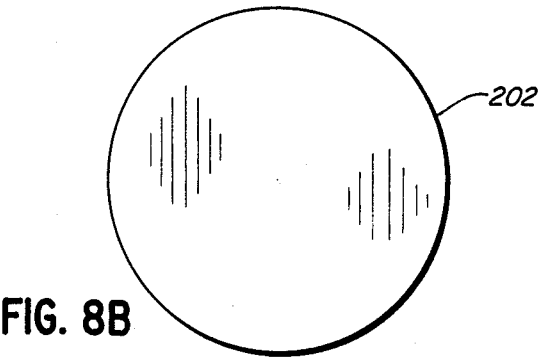
FIG. 8B is a plan view of the lower face of a handplate of the combined sensor along the line C—C of FIG. 8A.

FIG. 8E shows a circuit diagram of an analog detection circuit used with the compression sensor of FIGS. 8A-8D. Potentiometer 116 is connected between the main voltage +V and ground, and its wiper arm 213 provides an output voltage at 215 proportional to the relative position of wiper arm 213 in its stroke along the resistor of the potentiometer. Thus, pressing down on the manikin's chest pushes down handplate 202, causing a change in position of switchplate 204. The current position of switchplate 185 is reflected in the output of potentiometer 116, providing a means by which the amount of compression of the manikin's chest can be determined.

As the position of the student's hand on the manikin's chest is critical, handplate 202 and switchplate 204 cooperate to detect any error in hand position. The circular raised portion 205 on the upper face of switchplate 204 supports handplate 202 at distance d when handplate 202 is parallel to switchplate 204. The circular raised area 205 acts as a pivot about which handplate 202 can tilt if the student's hand is pressing off center, but only if it is sufficiently far off center to be outside the periphery of the upper surface of the raised portion 205.

Figure 8F:
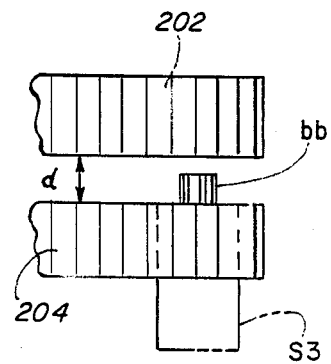
FIG. 8F is an enlarged cross-section of a top portion of the combined sensor of FIG. 8A near the edge.

Switchplate 204 carries a number of normally closed microswitches S3, S6, S9, S12 respectively mounted at the 3, 6, 9, and 12 o'clock positions near the plate's edge with their activating buttons bb protruding beyond the upper face of switchplate 204 as shown in FIG. 8F. The interplate distance d (when handplate 202 is parallel to switchplate 204) is chosen to provide enough clearance between the lower face of handplate 202 and the activating buttons of microswitches S3, S6, S9, S12 so that the microswitches remain open. However, if the student's hand position is not correct, handplate 202 will rock about the pivot protrusion 205, pushing down the activating buttons of one or more of the microswitches.

Figure 8C:
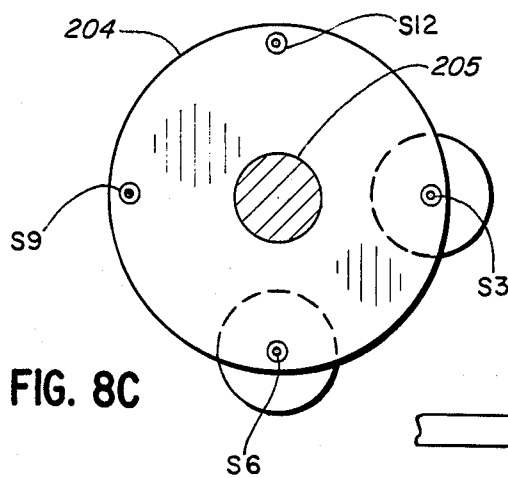
FIG. 8C is a plan view of the upper face of a switchplate of the combined sensor along the line C—C of FIG. 8A.

For example, if the student presses the handplate 202 at the relative position indicated by an X on switchplate 204 in FIG. 8C, handplate 202 will push down the activating buttons of switches S3 and S6. This causes normally closed switches S3 and S6 to open. The area of that upper surface of boss 205, however, defines a circle of hand position tolerance, within which the student's hand can be a little bit off center but not far enough to tilt the plate 202, and therefore will not actuate any of the microswitches S3, S6, S9, S12.

As can be seen in the control unit block diagram of FIG. 4, the opening of switches S3 and S6 will break the circuits providing current to LED's 71 and 72, turning off those LED's, which are physically located on control panel 53 of FIG. 2. Normally all four LED's surrounding the stylized heart symbol on control panel 53 of FIG. 2 are lit, but LED's 71 and 72 will now be off, indicating to the student the general direction (between 3 and 6 o'clock) of his hand placement error.

The opening of switches S3 and S6 will also change the corresponding voltage on inputs 71a and 72a to Position Switch Coder 86 from low (ground) to high, enabling coder 86 to report the presence of a hand position error to microcomputer 80a via port P9. This makes it possible to incorporate feedback coaching messages about the hand position in the teaching routines.

9. A/D Converters

Figure 9A:
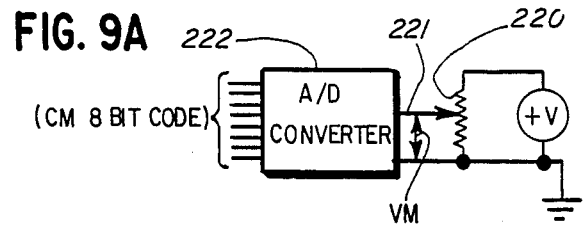
FIG. 9A is a simplified schematic of a conversion circuit which converts measurements of the student's efforts to an eight bit digital code.

To enable microcomputer 80a to digitally process the analog voltage signals from the ventilation sensor 182 and chest compression sensor 195, the voltage outputs from the corresponding measurement potentiometers 118 and 116 must be converted from analog voltage signals to an eight-bit digital code by respective A/D converters 119 and 117. FIG. 9A shows a typical conversion circuit in which measuring potentiometer 116 or 118 is connected between the main voltage +V and ground. The potentiometer's wiper arm 221 delivers an output voltage VM that represents the measured value of the ventilation or chest compression.

The output voltage VM is inputted to a suitable A/D converter integrated circuit 222. For example, National Semiconductor Corporation of Santa Clara makes a 5-volt input, 8-bit digital code A/D integrated circuit chip ADC 0803 that can be used for converter circuit 222. Each time A/D converter 222 converts the input VM to digital, the output is an eight-bit digital number whose value can range from decimal 0 ((hex, i.e. hexadecimal, 0) to decimal 255 (hex FF) and is proportional to voltage VM.

Figure 9B:
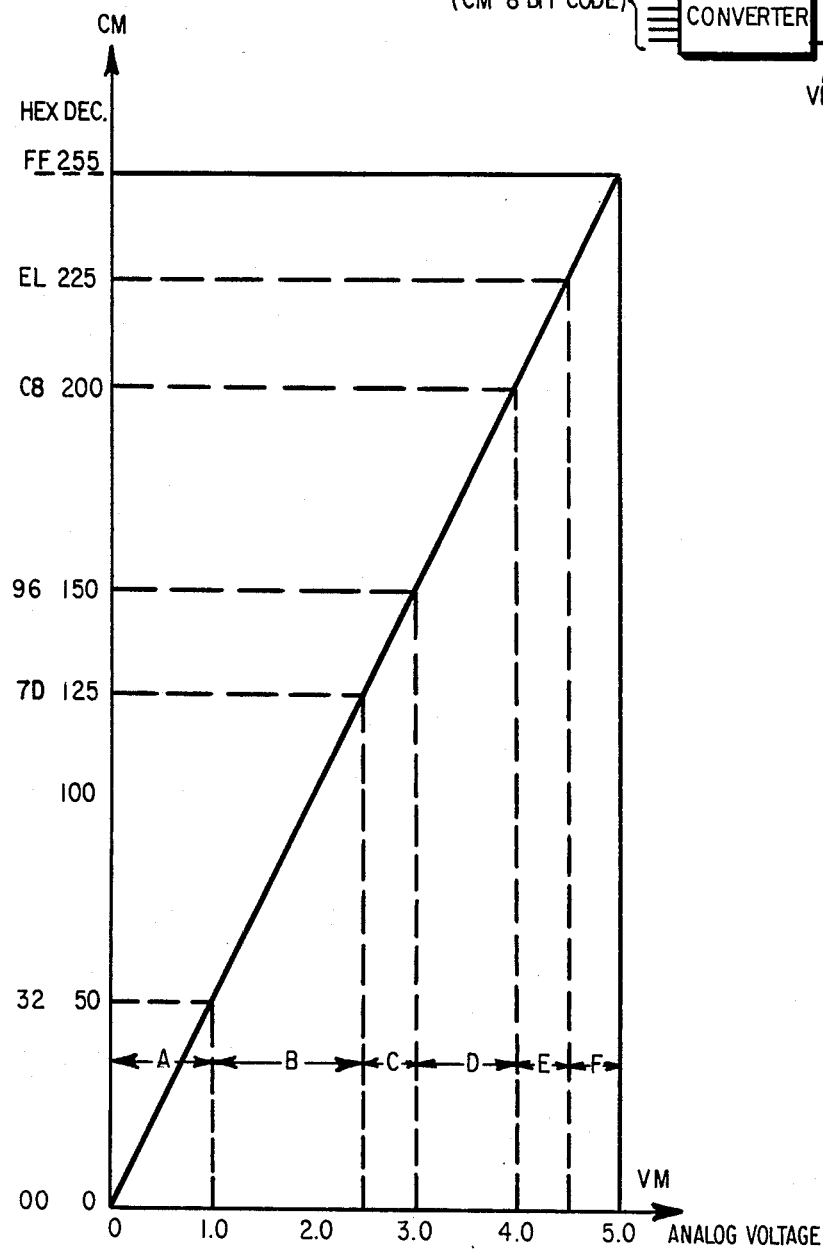
FIG. 9B is a curve showing the relationship between an input analog voltage measurement and an output digital code of the measurement.

The curve of FIG. 9B shows the relationship between the input analog voltage measurement VM and the output digital code measurement CM. Although the 255 levels of an eight-bit code enable the input signal VM to be quantized in steps finer than 1%, in judging the student's performance it is generally sufficient if the quantized signal is categorized into one of the six ranges A-F shown in FIG. 9B. For convenience in working with the microcomputer, integer values of the digital code CM are chosen for the boundaries between ranges rather than integral percentages. Thus, for example, range A, which represents the lowest values, is about the lowest 20% of the total range. However, for convenience this range A ends when the code measurement CM reaches the decimal value 50 (out of a maximum value of 255). Consequently, in terms of percent, range A covers from 0 to 19.2% of the maximum (0 to 0.96 volts). Table 1, which is more accurate than FIG. 9B, gives a detailed listing of the conversion values and the ranges A-F.

TABLE 1

A/D CONVERSION & RANGES

| RANGE | INPUT VOLTS VM | INPUT PERCENT | HEX OUTPUT CM | (DECIMAL VALUE) |
|---|---|---|---|---|
| A | 0.00–0.96 | 0.0–19.2 | 0–31 | 0–49 |
| B | 0.98–2.43 | 19.6–48.6 | 32–7C | 50–124 |
| C | 2.45–2.90 | 49.0–58.4 | 7D–95 | 125–149 |
| D | 2.94–3.92 | 58.8–78.4 | 96–C8 | 150–200 |
| E | 3.94–4.41 | 78.8–88.2 | C9–E1 | 201–225 |
| F | 4.43–5.00 | 88.6–100.0 | E2–FF | 226–255 |

Ventilation sensor 182 is calibrated to measure the volume of air in liters blown by the student into the manikin's artificial lung 184; a 100% reading (5 volts) is 2.5 liters. Chest compression sensor 195 is calibrated to measure the depth of the student's compression of the manikin's chest (at handplate 202) in inches; a 100% reading (5 volts) is a 2.5 inch compression. Table 2 shows how the ranges A-F are defined in terms of the measured quantities.

TABLE 2

| RANGE | INPUT AIR VOLUME (LITERS) | INPUT CHEST COMPRESSION (INCHES) | INPUT PERCENT | HEX OUTPUT CM |
|---|---|---|---|---|
| A | 0.00–0.48 | 0.00–0.48 | 0.0–19.2 | 0–31 |
| B | 0.49–1.22 | 0.49–1.22 | 19.6–48.6 | 32–7C |
| C | 1.23–1.46 | 1.23–1.46 | 49.0–58.4 | 7D–95 |
| D | 1.47–1.96 | 1.47–1.96 | 58.8–78.4 | 96–C8 |
| E | 1.97–2.21 | 1.97–2.21 | 78.8–88.2 | C9–E1 |
| F | 2.22–2.50 | 2.22–2.50 | 88.6–100.0 | E2–FF |

The ranges defined by FIG. 9B and Tables 1 and 2 are generally interpreted as follows in measuring the student's performance. Values in range A are below a minimum set to avoid erroneous readings. Values in range B are much too weak or shallow (too little air, too little chest compression); consequently the student is typically given the verbal feedback "MORE!" (where the exclamation mark indicates special emphasis in the tone of voice in which the message is delivered). Values in range C are close but still too weak or shallow; the verbal feedback is typically "MORE". Range D is the ideal range, so the verbal feedback is typically "GREAT". Values in range E are close but a bit too much; the verbal feedback is typically "LESS". Values in range F are much too strong, endangering the victim; therefore the verbal feedback is typically "LESS!".

10. Instructor Intervention System

Figure 10:
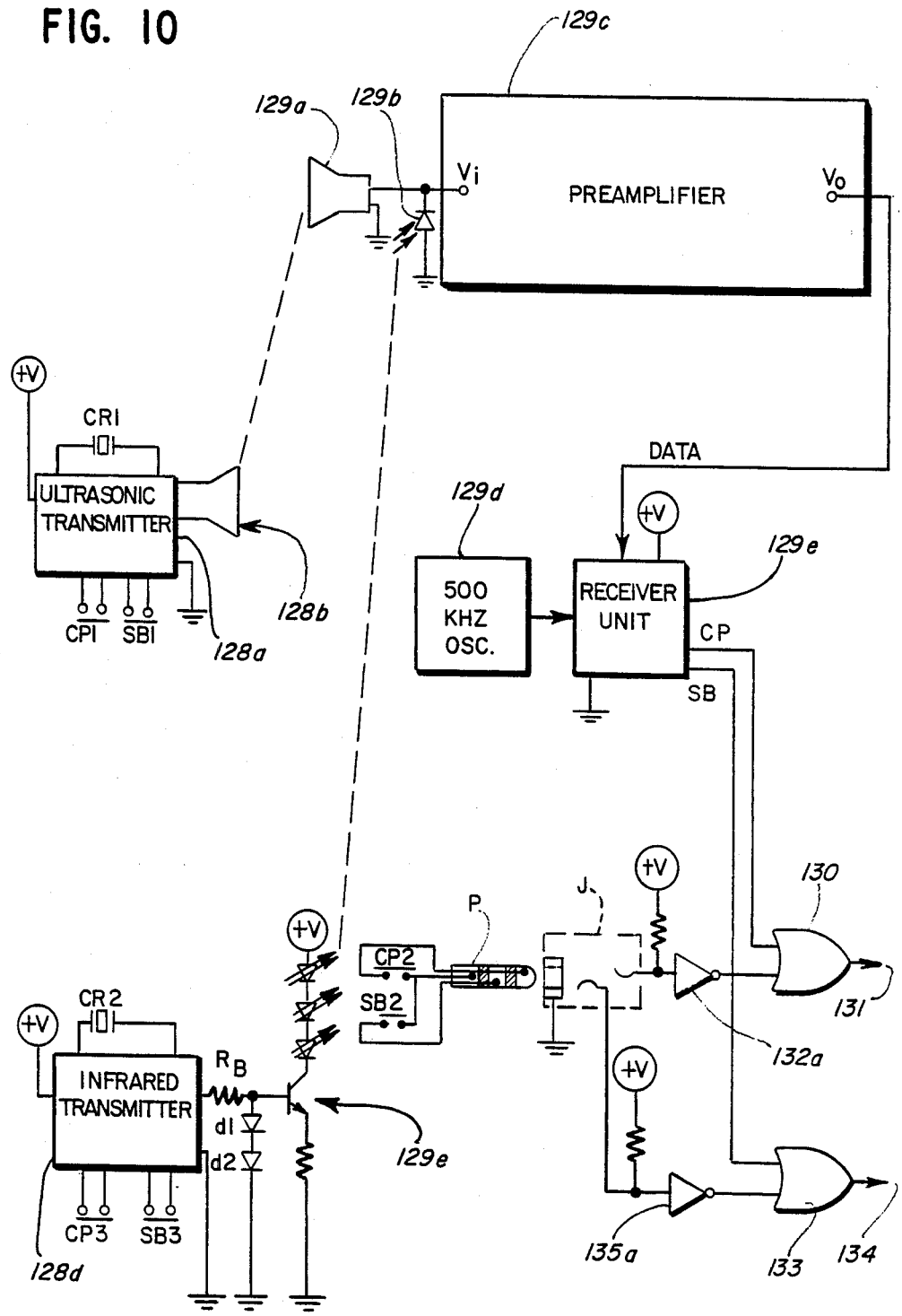
FIG. 10 is a detailed schematic of a remote-controlled instructor intervention system used with the control unit of FIG. 4.

FIG. 10 shows a more detailed schematic of the remote controlled instructor intervention system used with the control unit of FIG. 4. For wireless control, a two-channel ultrasonic transmitter 128a having control pushbuttons SB1 (shallow breathing) and CP1 (carotid pulse) is provided for the instructor. The transmitter sends an ultrasonic signal to a matching receiver 129e to indicate the logical state desired for two corresponding receiver outputs, SB and CP. It can be built from an integrated circuit chip of the type commercially available for ultrasonic control of TV receivers, games, etc, such as Motorola's CMOS monolithic transmitter chip MC14457.

The Motorola chip has an amplifier for driving a miniature ultrasonic ceramic microphone with a frequency-modulated biphase signal. A ceramic resonator CR1 is attached to provide a 500 kHz clock signal that is divided down to yield a high-frequency output of 41.67 kHz and a low-frequency output of 38.46 kHz. To transmit a logical 0, the microphone is driven for 256 periods of the low frequency, followed by 256 periods of the high frequency. For a logical 1, the order of the two frequencies is reversed. Circuitry in the transmitter chip incorporates these frequency-coded signals into a 7-bit data word format having a fixed two-bit start pattern and five data bits, not all of which are used by this invention.

At the receiver end, a ceramic mike 129a is provided to detect the modulated ultrasonic signals and convert them to an electrical signal that is inputted to a preamplifier 129c. The preamplifier receives the detected signal at an input $V_i$ and amplifies and limits it in a conventional manner to shape it into a digital square wave DATA signal, which is then outputted at a terminal $V_o$.

The DATA signal from preamplifier 129c is inputted to a suitable receiver chip 129e matched to decode the modulated signals from the transmitter. For example, Motorola Semiconductor Products sells a matched receiver MC14458 chip for decoding signals modulated by its MC14457 transmitter chip. To match the clock in the transmitter, a 500 kHz oscillator 129d provided to input a basic clock pulse to the receiver chip. The receiver chip 129e then decodes the DATA signal to detect which of the selection buttons, CP1 or SB1, was pushed at the transmitter. A corresponding output CP or SB of receiver 129e is then set to 1.

The remote control signal sent by the instructor can also be conveyed by means of control wires. FIG. 10 shows selection buttons CP2 and SB2 for the instructor that are carried by a suitable 3-wire cord to a three-wire plug P. A matching three-wire jack J on the control unit 52 receives the plug P. By means of the wire, plug and jack, pressing selection button CP2 results in the grounding of the input to an inverter 132a, causing the inverter to output a logical 1 whenever the instructor pushes button CP2. Similarly, pressing button SB2 grounds the input of an inverter 135a, which then outputs a logical 1.

The two inputs of OR gate 130 respectively receive the output CP of receiver 129e and the signal from inverter 132a. The output of OR gate 130 is inputted as a carotid pulse transducer control signal to input 131 of selection switch coder 84. Thus, if wireless output CP or the output of inverter 132a is a logical 1, OR gate 130 will output a logical 1 to input 131 to signal microcomputer 80a to activate the carotid pulse transducer 91.

Similarly, the inputs of OR gate 133 receive the output SB of receiver 129e and the signal from inverter 135a. If wireless output SB or the output of inverter 135a is a logical 1, OR gate 133 will output a logical 1 to input 134 to signal microcomputer 80a to activate the shallow breathing transducer 94.

Alternatively, the instructor can be provided with a wireless transmitter 128d that sends infrared signals to indicate which of two buttons, CP3 (carotid pulse) or SB3 (shallow breathing) has been pressed. The modulation scheme can be similar to that used for the ultrasonic signals.

The previously mentioned Motorola MC14457 transmitter chip can alternatively be wired to modulate the output of LED diodes $d_I$ that emit an infrared beam. As before, a ceramic resonator CR2 is attached to form a 500 kHz clock signal used to provide the high- and low-frequency modulation signals. The frequency-modulated biphase signal formed by the transmitter chip is inputted through a base resistor $R_B$ and clipping diodes $d_1$ and $d_2$ to the base of a driving transistor 129e. Transistor 129e modulates the infrared beam by switching on and off the current through the LED diodes $d_I$, which are wired in series between the collector of transistor 129e and the main voltage +V.

At the receiver end, a suitable infrared photodiode 129b is 25 provided at input $V_i$ of preamplifier 129c for detection of the modulated infrared beam. Otherwise, the receiver circuitry and signal processing remains unchanged from that used for the ultrasonic signals.

SYSTEM OPERATION

1. Start Up

Until a selection button is pressed, the system remains in a low-power standby mode in which the main voltage +V is off and microcomputer 80a is not operating. Only a standby voltage $V_a$ powers those few circuits which must always be able to respond to the pressing of a selection button, such as selection switch coder 84. However, as explained above in connection with the control unit 52 of FIG. 4, pressing any program switch 56–63 causes the standby circuits to turn on the main voltage +V and also causes selection switch coder 84 to send a hardware interrupt signal on line 85 to microcomputer 80a.

Figure 11:
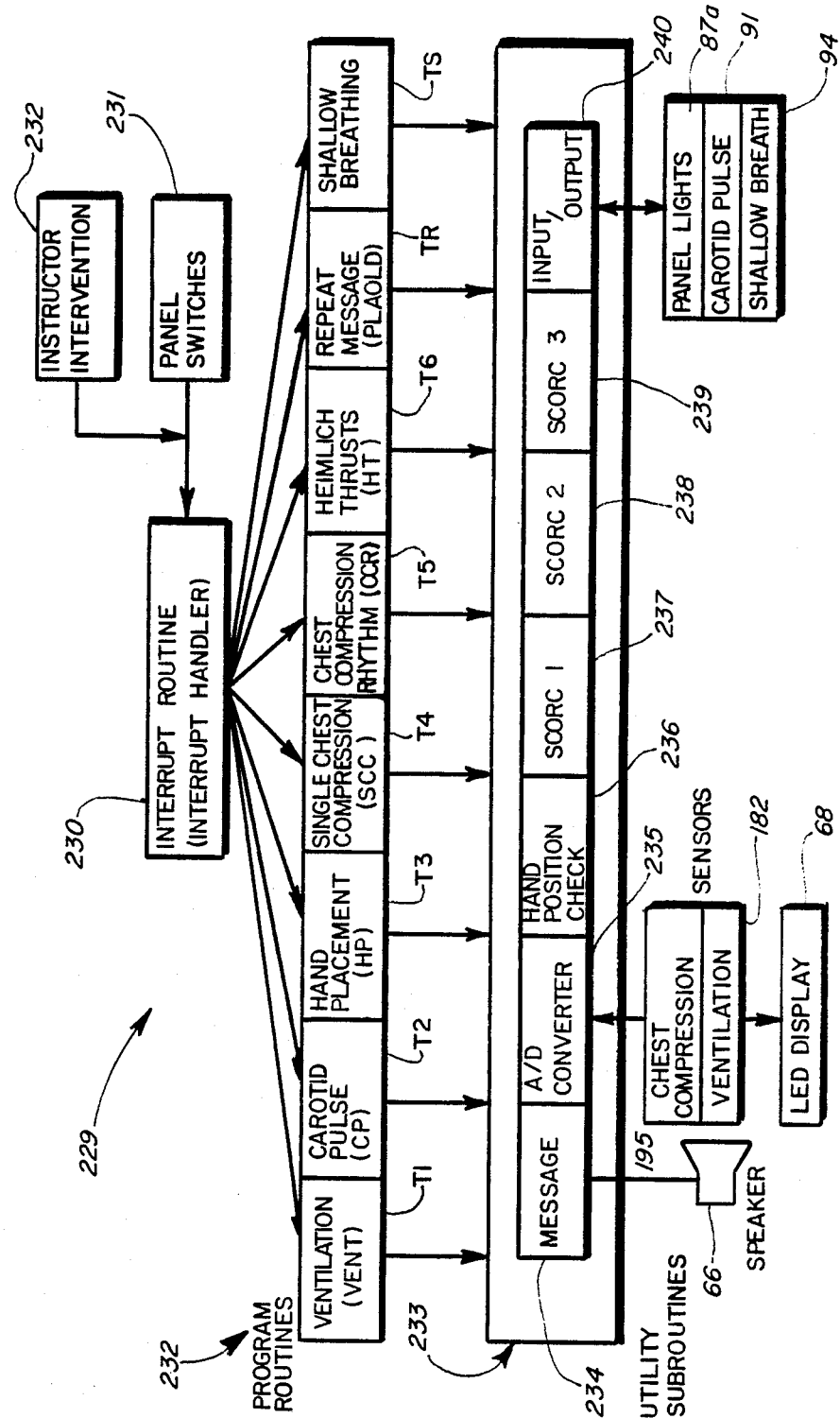
FIG. 11 is a block diagram of an embodiment of a Control Program for use with the control unit of FIG. 4.

Once provided with main voltage +V, microcomputer 80a automatically initializes itself and then transfers control to an Control Program 229 represented in FIG. 11. All of the instructions enabling the microcomputer 80a to implement the Control Program are prestored in the four-kilobyte ROM 81 on board the microcomputer chip 80a, with the exception of speech sounds prestored in the speech memory chips 104.

The complete Control Program is listed in assembly language in Appendix II filed with this patent application.

2. Interrupt Routine

Control Program 229 begins with an Interrupt Routine 230 to service the interrupt signal from selection switch coder 84 to provide a particular program routine 232 corresponding to whichever one of the panel switches 231 has been pressed. If the instructor makes a remote-controlled request for a carotid pulse or shallow breathing, this instructor intervention 232 also sends a hardware interrupt to microcomputer 80a which is immediately serviced by Interrupt Routine 230.

Interrupt Routine 230 gets its name from the fact that an interrupt signal on the microcomputer's line 85 causes microcomputer 80a to stop whatever routine it is currently processing and jump to the instructions of the Interrupt Routine 230 in order to respond to the interrupt signal. To permit a subsequent return to the routine that was interrupted, if desired, the contents of the working registers and the address of the next instruction for the interrupted routine are pushed onto the microcomputer's stack, a last-in-first-out (LIFO) storage area of RAM 82. After the interrupt is processed, the information on the stack can be retrieved to resume processing of the interrupted routine.

The interrupt signals sent to microcomputer 80a on line 85 by selection switch coder 84 are coded to indicate the particular program routine selected. As can be seen in FIG. 11, the program routines available are Ventilation T1, Carotid Pulse T2, Hand Placement T3, Single Chest Compression T4, Chest Compression Rhythm T5, Heimlich Thrusts T6, Repeat Message TR, and Shallow Breathing TS. Also available, but not shown in FIG. 11, is a Pause Routine incorporated into Interrupt Routine 230.

To carry out their functions, the program routines can invoke Utility Subroutines 233. These utility routines are Message 234, A/D Conversion 235, Hand Position Check 236, scoring routines SCORC1 237, SCORC2 238 and SCORC3 239, and Input/Output 240. Message subroutine 234 outputs a message of a designated number via speaker 66 for voice feedback. A/D Conversion subroutine 235 takes readings from ventilation sensor 182 and compression sensor 195 and converts them to an eight-bit digital code (FIGS. 9A and 9B). Hand Position Check routine 236 gives corrective comments on the student's hand position for chest compressions.

The utility routines include three scoring subroutines: SCORC1 subroutine 237 scores and tallies the amount of each ventilation of the manikin's artificial lung or the depth of each chest compression, interjecting an immediate single brief (about $\frac{1}{3}$ second) word of praise or criticism to the student via message subroutine 234. Tee SCORC2 subroutine 238 vocalizes the tally of the student's efforts for 15 successive chest compressions. The SCORC3 subroutine 239 voices a criticism of the rhythm of the student's 15 chest compressions.

The Input/Output subroutine 240 enables control of the panel lights 87a carotid pulse transducer 91, and shallow breathing transducer 94.

Figure 12A:
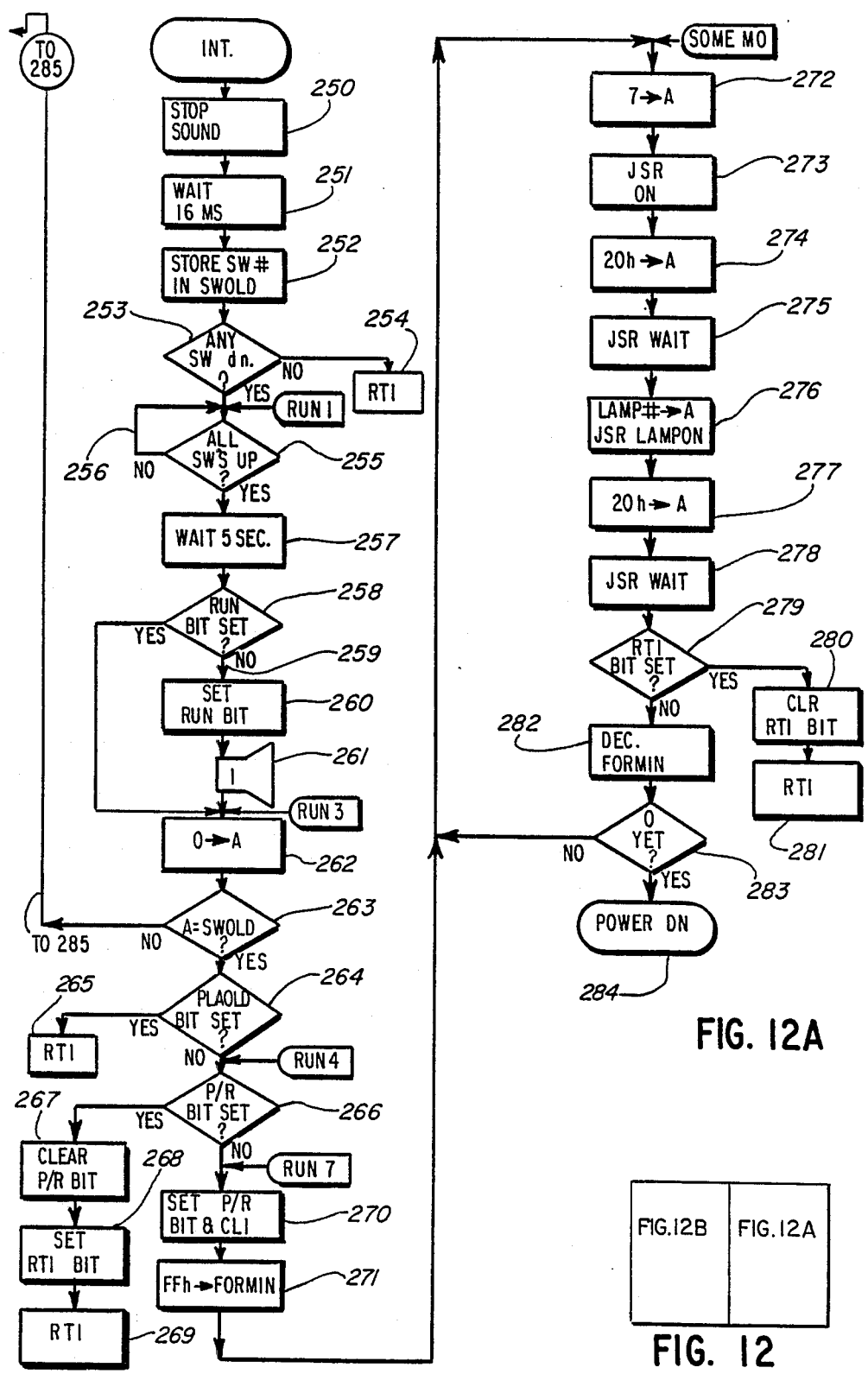
FIGS. 12, 12a and 12b are a flow chart for an embodiment of the Interrupt Routine incorporated in the Control Program of FIG. 11 and includes the Repeat Message Subroutine of FIG. 11.
Figure 12:
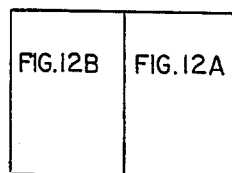

A flow chart for an embodiment of the interrupt routine is shown in FIG. 12. For convenience in programming the routine in assembly language, mnemonic labels have been added at certain key steps (e.g. see the label RUN1 at STEP 255). However, the description of this and other routines that follows ignores these occasional mnemonic labels and instead uses appended reference numbers.

Microcomputer 80a interrupts whatever program code it is processing and jumps to this routine whenever selection switch coder 84 sends a coded interrupt. As microcomputer 80a might have been in the middle of playing a message, a control signal is sent to stop the sound to speaker 66 (STEP 250). A short 16 ms wait is introduced (STEP 251) to block out any effects of bouncing of the switch contacts of selection switches 56-63. Switch coder 84 sends a coded interrupt giving the number of the selection switch that was pressed; this number is stored as SWOLD (switch old) (STEP 252). To rule out the possibility of a brief noise transient causing the interrupt signal, a check is made to see if some selection switch is still down, that is, is the interrupt signal still present on line 85 (STEP 253). If no switch is down, a false interrupt by a noise transient is assumed, and a return from interrupt (RTI) is made to resume the interrupted routine (254).

If a switch is down at STEP 253, a further check of the interrupt line is made at STEP 256 to see if all switches are now up (interrupt no longer present). If some switch remains down, the program loops back (STEP 256) until all switches are up. Before proceeding, a half-second delay is introduced to avoid the problems of too quick a response (STEP 257).

If the interrupt routine is running for the first time since the main voltage +V was turned on, the memory will be clear and a bit called RUN BIT will not be 1 (it will be 0). A check of RUN BIT is made (STEP 258). If RUN BIT is not 1, it is set to 1, and a welcoming Message 1 (see Appendix I) is voiced via the Message subroutine (STEP 261).

Now the interpretation of switch number SWOLD begins. The selection switches use the following code:

| SWOLD | SWITCH NAME | PART NUMBER |
|---|---|---|
| 0 | PAUSE/RESUME | 63 |
| 1 | REPEAT MESSAGE | 62 |
| 2 | HEIMLICH THRUSTS | 61 |
| 3 | CHEST COMPRESSION RHYTHM | 60 |
| 4 | SINGLE CHEST COMPRESSION | 59 |
| 5 | HAND POSITION | 56 |
| 6 | CAROTID PULSE | 57 or 131 |
| 7 | VENTILATION | 58 |
| 8 | SHALLOW BREATHING | 134 |

A zero is loaded in the accumulator A (STEP 262) so SWOLD can be compared with 0 (STEP 263). If the P/R bit is not set to 1 (is 0), a PAUSE is desired, and the P/R bit is now set (STEP 270). An operation called CLI, Clear Interrupt Mask bit, is performed so that the PAUSE itself can be interrupted by the later pressing of a selection key, either the PAUSE/RESUME key or another selection key.

The PAUSE routine is designed to wait as long as 4 minutes for the PAUSE/RESUME button to be pressed again for RESUME. As a counter, the variable FOURMIN is set to hex FF (decimal 255).

While in the pause mode, the PAUSE/RESUME lamp 63a on control panel 53 (FIG. 2) and the lamp of the routine that was in progress before the PAUSE are alternately flashed. The accumulator A is set the code number (7) of the PAUSE/RESUME lamp 63a, and a service routine ON is called to turn on the lamp whose code is in accumulator A. A half second delay (512 ms) is introduced by setting A to hex 20 (decimal 32) in STEP 274 and calling a service subroutine WAIT (STEP 275) that introduces a delay of 16 ms times the number in Accumulator A.

The lamp number of the interrupted routine, found as the current value of a variable LAMP, is then loaded in the accumulator A and service routine ON called to light the indicated lamp (STEP 276) for a half second (STEPS 277 & 278).

If at STEP 279 a bit called RTI is found to have been set to 1 (by a method to be explained shortly), the PAUSE is ended by clearing the RTI bit to 0 and executing a RETURN FROM INTERRUPT (RTI) to resume the routine interrupted by the PAUSE. On the other hand, if the RTI bit is not yet set, the variable FOURMIN is decremented by 1 (STEP 282) and if it is not yet 0 (STEP 283) the program loops back to STEP 272 to blink the lamps again. If FOURMIN does get decremented to zero, four minutes have elapsed since the PAUSE button was pressed and the system enters the lower power standby mode by turning off the main voltage +V.

If at STEP 266 the bit called P/R is found to be a 1, a PAUSE is already in progress and the current pressing of PAUSE/RESUME indicates that a RESUME is desired. The P/R bit is cleared to 0, the bit called RTI is set to 1 to indicate that the PAUSE should be ended the next time STEP 279 is passed. Next a return from interrupt (RTI) is made (STEP 281) that transfers control back to the loop of steps between STEPS 272 and 283 used to implement the PAUSE. In other words, the way to end the PAUSE is to interrupt it for a brief interval by pressing the PAUSE/RESUME key again: this enables the RTI bit to be set to 1 at STEP 269, so that when the PAUSE is resumed it will terminate via STEPS 279, 280 and 281.

Returning to STEP 263, if SWOLD is not a 0, Accumulator A is incremented from 0 to 1 (STEP 285) and a check is made to see if SWOLD is a 1 (STEP 286), which would indicate that the REPEAT (last) MESSAGE button 62 was pressed. If it was, a check is made to see if a bit called PLAOLD is set (STEP 287). If it is not, a repeat of the last message played can be executed. The REPEAT MESSAGE lamp 62 on panel 53 is turned on (STEP 289), and to indicate to later interrupts that a REPEAT MESSAGE is in progress, the PLAOLD bit is set to 1 (STEP 290). The operation called CLI, Clear Interrupt Mask bit, is performed (STEP 291) so that the REPEAT MESSAGE itself can be interrupted by the later pressing of a selection key.

The message number of the last message is found from the current value of the variable LASTMS (last message), which is loaded in register X (STEP 292) and the subroutine Message is called to play the message whose number is in register X.

A bit called the RETURN bit is set (STEP 294) so that should the interrupt end with control resuming in the playing of message, that message will be aborted (having already been replayed by the REPEAT MESSAGE button). Since the message desired has been fully repeated, the PLAOLD bit is now cleared (STEP 295).

If the REPEAT MESSAGE button was pressed while a WAIT subroutine was being executed, the WAIT should be preferably aborted when control is passed back to it, so the student can act on the repeated message. Such an abort or quick return is enabled by setting a variable WAITC to 1 (STEP 296). Similarly, a bit called SILREG (silence register) bit and a variable called SILREG (silence register) are zeroed (STEPS 297 & 298) to remove any now unnecessary voicing pauses when control is resumed by the interrupted routine. The REPEAT MESSAGE lamp is turned off (299) and a Return From Interrupt (RTI) is executed (300).

Returning to STEP 287, if the PLAOLD bit is set, a REPEAT MESSAGE must already be in progress (see STEP 290). The REPEAT MESSAGE button must have been pushed and should be ignored, which is done by terminating the interrupt by a Return From Interrupt (RTI).

Returning to STEP 286, if SWOLD is not a 1, one of the other selection buttons must have been pressed for a switch to a fresh teaching routine; there will be no Return From Interrupt (RTI) to the interrupted routine. Since there will be no return from the interrupt, a Reset Stack Pointer (RSP) instruction is executed (STEP 301). As housekeeping measures before executing the new routine, the microcomputer's flags are cleared (STEP 302), and the byte ALLBIT and a byte called RAMBIT are cleared (STEP 302), the carotid pulse driver 92 is turned off (should it be on), and a service routine LAMPS is called to turn off the READY (also called "WAIT[ING]") or REPEAT MESSAGE lamps.

STEPS 305, 306 load a 2 into Accumulator A and compare it with SWOLD. If SWOLD is 2, there is a jump to the Heimlich Thrusts teaching routine (STEP 307). Otherwise, STEPS 308, 309 increment Accumulator A from 2 to 3 and compare it with SWOLD. If SWOLD is 3, there is a jump to the Chest Compression Rhythm routine (STEP 310). Otherwise, STEPS 311, 312 increment Accumulator A from 3 to 4 and compare it with SWOLD. If SWOLD is 4, there is a jump to the Single Chest Compression teaching routine (STEP 313).

Similarly in STEPS 314, 315, if SWOLD is 5, there is a jump to the Hand Position teaching routine (STEP 316). In STEPS 317, 318, if SWOLD is 6, the jump is to the Carotid Pulse teaching routine (STEP 319). In STEPS 320, 321 if SWOLD is 6, there is a jump to the Ventilation teaching routine (STEP 322). Otherwise, at STEP 323 a jump is made to the Shallow Breathing routine.

Thus the Interrupt Routine acts as the central routine by which the student, or the instructor by intervention, can select the next routine to be run, or interrupt a currently running routine for a quick repeat of the last message or a pause of up to four minutes.

3. Ventilation Teaching Routine

Figures 13, 13A, 13B:
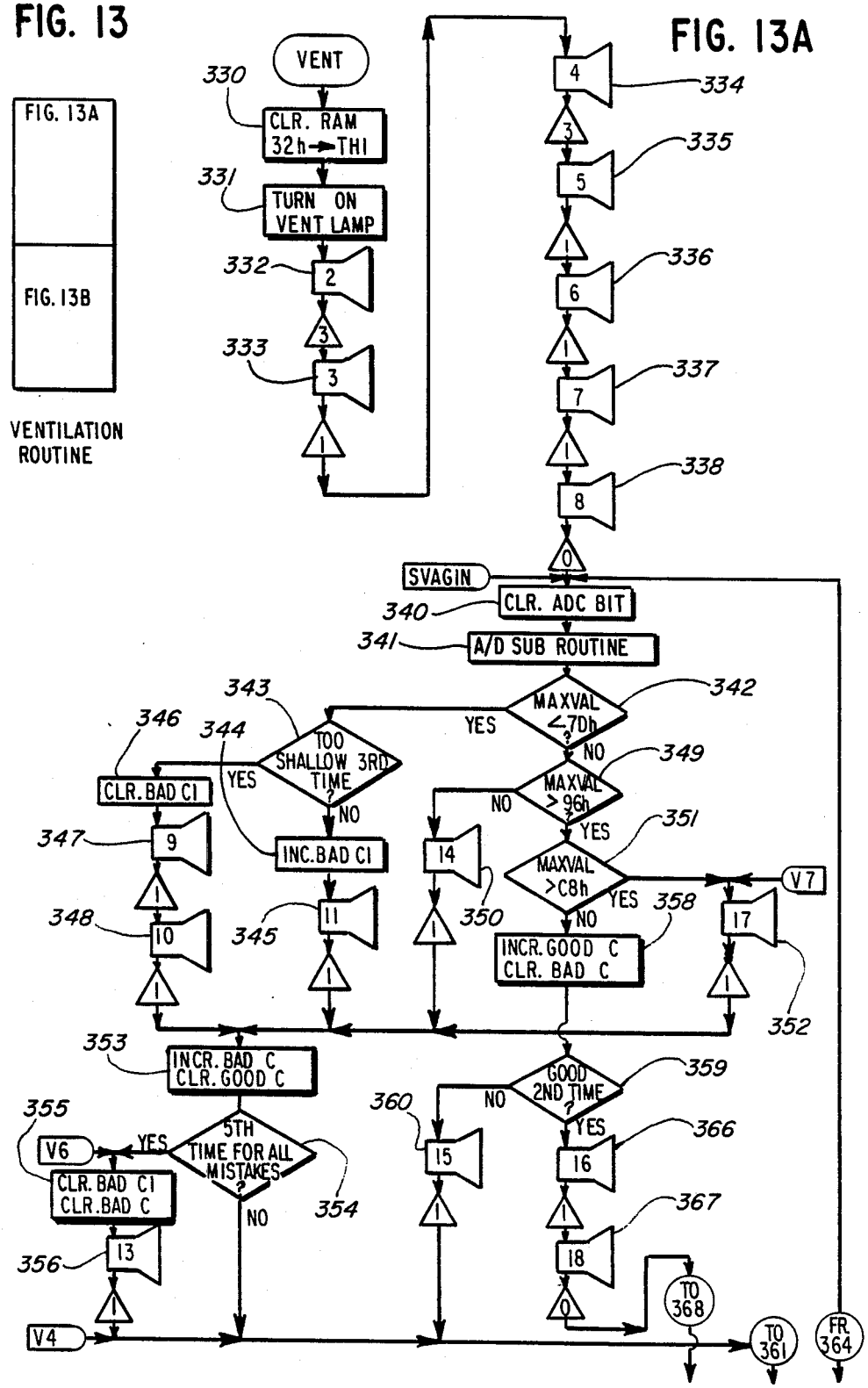
FIGS. 13, 13a and 13b are a flow chart for an embodiment of the Ventilation Teaching Routine incorporated in the Control Program of FIG. 11.
Figure 13B:
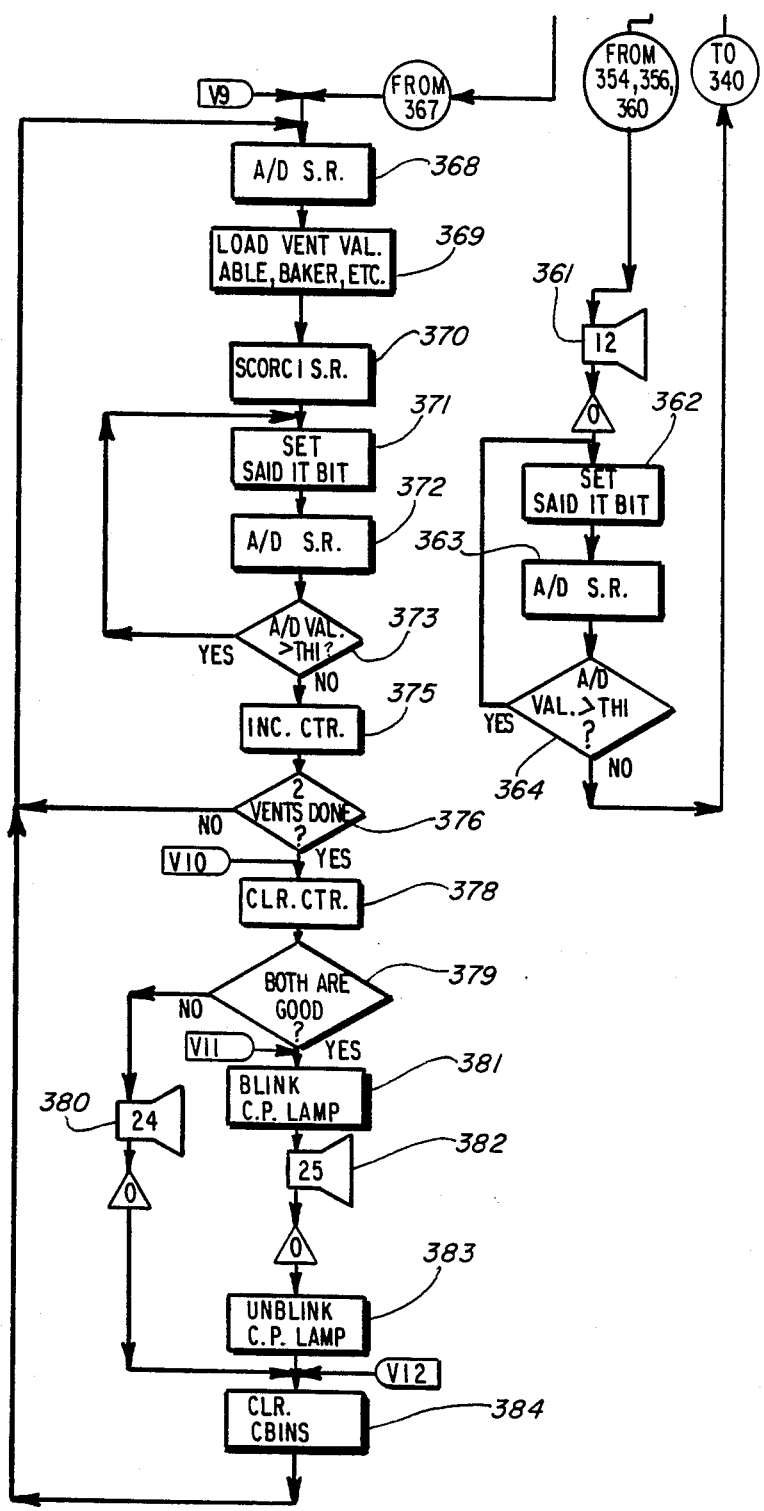

FIG. 13 shows a flow chart of an embodiment of the Ventilation Teaching Routine for practice of artificial respiration. The purpose of the routine is to have the student practice blowing air into the manikin's artificial lung until the student can do two successive correct single ventilations. Then the student practices multiple ventilations, two at a time.

The Ventilation routine begins by clearing the microcomputer's RAM 82 (STEP 330) and setting a noise reducing threshold value TH1 which a given ventilation sensor measurement must reach before being recognized as an effort by the student. The threshold TH1 is set to hex 32, which corresponds to threshold of 0.49 liters of air in the manikin's lung 184. Values in Range A of FIG. 9B and Table 2 are below the threshold. To show which routine is running, the AIRWAY VENTILATION lamp 58 is turned on (STEP 331).

To indicate various messages which are voiced by the Message routine, the flow chart of FIG. 13 includes a speaker symbol for each message, on which appears the number of the message. A complete listing of the messages by message number appears in Appendix I. Pauses introduced between the messages by the delay subroutine called WAIT are indicated by a triangle symbol, on which is written the number of seconds of delay. Since these pause symbols are self-explanatory, they will not be explicitly mentioned as numbered steps in the following description of the Ventilation and other routines.

STEPS 332–338 voice Messages 2–8 as instructions to the student for beginning artificial respiration. The result is as follows:

Ventilation. Open the airway by gently tilting the head way back. Press down on the manikin's forehead with the palm of one hand. With your other hand, lift either under the neck, near the base of the head, or with the fingertips, under the bony part of the jaw near the chin. Pinch off the manikin's nostrils. Open your mouth wide, take a deep breath, and make a tight seal with the manikin's mouth and blow. Try a single ventilation. I will tell you how you did.

A bit called the ADC bit is cleared to 0 (STEP 340) to indicate that the A/D Conversion utility subroutine should read in analog data from the ventilation sensor 118 rather than the chest compression sensor 116. Then the A/D subroutine is called (STEP 341). Whenever the A/D subroutine is called to take data, it begins by turning on READY lamp 65 on control panel 53 (FIG. 2), so the student will know the system is ready to monitor his efforts. When the student then tries blowing into the manikin's lung, the A/D subroutine quickly takes a series of sample readings of the ventilation sensor 118. When the student's effort has peaked, the A/D subroutine sets a variable called MAXVAL equal to the A/D converted peak or maximum value and returns control to the Ventilation routine.

If STEP 342 determines that MAXVAL is less than hex 7d (1.23 liters), the student's attempt lies in Range B and is too weak. If STEP 343 determines (from a counting variable called BADC1) that it is not yet the third time the student's attempt was in Range B, the counting variable BADC1 is incremented by 1 (STEP 344) and coaching Message 11 is voiced: Blow Harder. Then the routine proceeds to STEP 353.

On the other hand, if the student's attempts repeatedly fall in Range B, variable BADC1 will soon be incremented to a 2. In this case, after the third such weak attempt STEP 343 switches control to STEP 346. The variable BADC1 is cleared to zero and coaching messages 8 and 9 are voiced: "More air. Be sure that you're taking a deep breath and keeping a tight seal with the manikin's nostrils." Then the routine proceeds to STEP 353.

The coaching messages are voiced promptly after the student's attempt has peaked, with a natural timing, inflection, tone, and volume that simulates human coaching.

If STEP 342 finds that MAXVAL is equal to or greater than hex 7d, STEP 349 determines if MAXVAL is greater than hex 96. If it isn't, the student's effort lies in Range C (1.23-1.46 liters), still too little. Therefore, at STEP 350 Message 14 is voiced: "Close, but blow harder." Then the routine proceeds to STEP 353.

If STEP 349 determines that MAXVAL exceeds hex 96, STEP 351 determines if MAXVAL is greater than hex C8 (1.96 liters). If it is, the student's attempt lies in Range E or F and is too strong. Therefore, STEP 352 voices Message 17: Good, but blow less forcefully. Then the routine proceeds to STEP 353.

The acceptable range for the student's efforts is 1.47-1.96 liters, Range D. Efforts in Range A will be below threshold. Efforts in Ranges B, C, E, and F all lead to STEP 353, which increments a counter variable BADC (bad count). Because the student has produced a bad ventilation, STEP 353 also penalizes him by setting to zero a counter variable GOODC (good count) used to count any acceptable ventilations in Range D.

STEP 354 checks variable BADC to see if 5 bad ventilations have accumulated. If BADC is currently less than 5, the routine jumps to STEP 361. But if 5 bad ventilations have accumulated, the student needs a fresh start with special instructor coaching. STEP 355 clears counter variables BADC1 and BADC and STEP 356 voices Message 13: "Please ask the instructor for help." Then the routine proceeds to STEP 361.

If STEP 351 determines that MAXVAL is not greater than C8, then the student's attempt lies in Range D and is acceptable. STEP 358 increments counter variable GOODC (good count). Because the student has now produced a good ventilation, STEP 358 also erases his past learning errors by setting to zero the "bad count" counter variable BADC. If STEP 359 determines that two good ventilations have not yet been produced, the student is praised at STEP 360, "Excellent", but the routine proceeds for more practice to STEP 361.

STEP 361 uses Message 12 to direct the student to "Try it again." STEP 362 sets a bit called SAIDIT to 1 to indicate that a maximum of the student's effort has already been determined and a critique voiced.

The microcomputer's response may be so prompt that the student is still in the process of blowing into the manikin, though the peak of his effort has passed. Therefore, STEP 363 calls the A/D subroutine to read and convert the current instantaneous value of the ventilation sensor, and set the variable ADVAL equal to it. Because the SAIDIT bit is set, the A/D subroutine will just give the instantaneous reading ADVAL and not try to determine a maximum from a series of readings as before. The A/D subroutine also clears the SAIDIT bit to 0.

STEP 364 determines if ADVAL exceeds the threshold TH1. If it does, the student is not through blowing and the routine loops to STEP 362 to again set the SAIDIT bit and take another instantaneous reading.

When ADVAL falls below the threshold TH1, the student is finished and ready to make a fresh effort. The routine loops back to STEP 340 to find the maximum of the student's fresh effort via the A/D subroutine.

Eventually the student will achieve two good ventilations in a row. The counter variable GOODC will become 2 and at STEP 359 the routine will go to STEPS 366 and 367, which respectively voice Messages 16 and 18: Perfect, now try giving two slow breaths. Blow into the manikin's mouth with complete refilling of your lungs after each breath.

STEP 368 calls the A/D subroutine to get the peak or maximum value of the first of the student's two efforts and store it as the variable MAXVAL. The ranges above threshold, B, C, D, E, and F, have the respective maximum hex values 7C, 95, C8, and E1. These are respectively stored under the variable names ABLE, BAKER, CHUCK, and DOG (STEP 369), and then the scoring subroutine SCORC1 is run. Depending on the value of MAXVAL, SCORC1 will voice one of the following brief words of criticism or praise, and increment one of the following counter variables:

TABLE 3

| MAXVAL (HEX) | RANGE | OUTPUT OF SCORC1 BRIEF CRIT. | MESS. # | INCREMENT COUNTER |
|---|---|---|---|---|
| 32-7C | B | MORE! | 19 | CBIN1 |
| 7D-95 | C | MORE | 20 | CBIN1 |
| 96-C8 | D | GREAT | 21 | CBIN2 |
| C9-E1 | E | LESS | 22 | CBIN3 |
| E2-FF | F | LESS! | 23 | CBIN3 |

The single short word of praise or criticism MORE!, MORE, GREAT, LESS, OR LESS!, is an important feature of the invention since it can be voiced in the brief time between the student's efforts, yet gives immediate aural feedback, including inflection, tone, volume, and urgency. This feedback technique is also used in the chest compression rhythm sequence, where typically there is only about 0.6 seconds between chest compressions. Because such short words can be voiced in about 0.3 seconds, they are effective in giving immediate feedback and advice after each compression.

Then STEPS 371 AND 372 wait for the student to finish the current attempt in same manner as STEPS 362 and 363 described above. A counter CTR is incremented (STEP 375) to keep track of the number of attempts by the student. If the count in counter CTR is not equal to or greater than two, the routine loops back to STEP 368 for the second of the student's two efforts.

When counter CTR shows that two efforts have been processed in this manner, the counter CTR is cleared (STEP 378). The number of good ventilations will be in CBIN2. If this number is not two, STEP 380 voices Message 24: Try giving two breaths again. Then STEP 384 clears the counter variables CBIN1, CBIN2, and CBIN3 and the routine loops back to STEP 368 for the student to try again.

If at STEP 379 the number in CBIN2 was two (both ventilations good), the student is ready to try the next teaching routine. The lamp 57a for the Carotid Pulse routine is blinked (STEP 381), and STEP 382 voices Message 25: "Excellent ventilation. If you feel confident, practice checking the carotid pulse. If you don't, try giving two breaths again."

STEP 383 stops the blinking of the Carotid Pulse lamp, and STEP 384 clears the counter variables CBIN1, CBIN2, and CBIN3. Although the routine loops back to STEP 368 for the student to try again, he can break out of the ventilation routine by pressing the selection button for another routine, such as the following.

Carotid Pulse Teaching Routine

Figure 14:
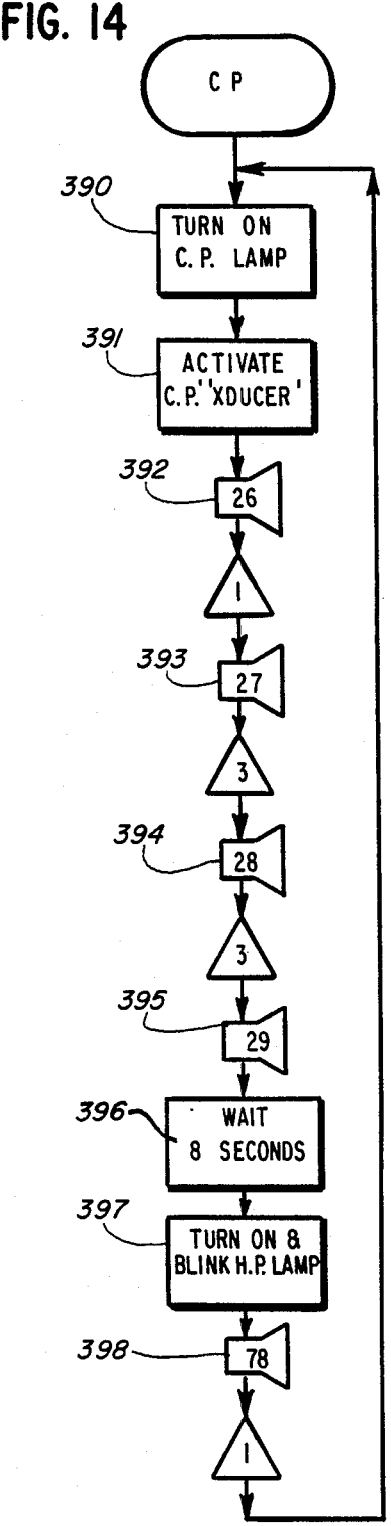
FIG. 14 is a flow chart for an embodiment of the Carotid Pulse Teaching Routine incorporated in the Control Program of FIG. 11.

FIG. 14 shows a flow chart of an embodiment of the Carotid Pulse Teaching Routine for practice in locating and feeling the carotid pulse simulated in the manikin's neck by the carotid pulse transducer 91. STEPS 390 and 391 turn on the Carotid Pulse lamp 57a and activate the carotid pulse transducer 91. STEPS 392–395 respectively voice Messages 26–29, with the following result:

Carotid pulse. The carotid pulse is located on either side of the Adam's Apple. Gently, try to sense it with the index and middle fingers of one hand. Maintain the head tilt with the palm of your other hand. If you have difficulty checking it, please ask the instructor for help.

STEP 396 provides about an eight-second pause for the student to carry out the procedure. The Hand Position lamp 56a is blinked (STEP 397) and Message 78 is voiced (STEP 398): Now practice the correct hand position. Although the routine loops back to STEP 390 for the student to try again, he can break out of the carotid pulse routine by pressing the selection button for another routine, such as the Hand Position routine.

Hand Placement Teaching Routine

Figure 15:
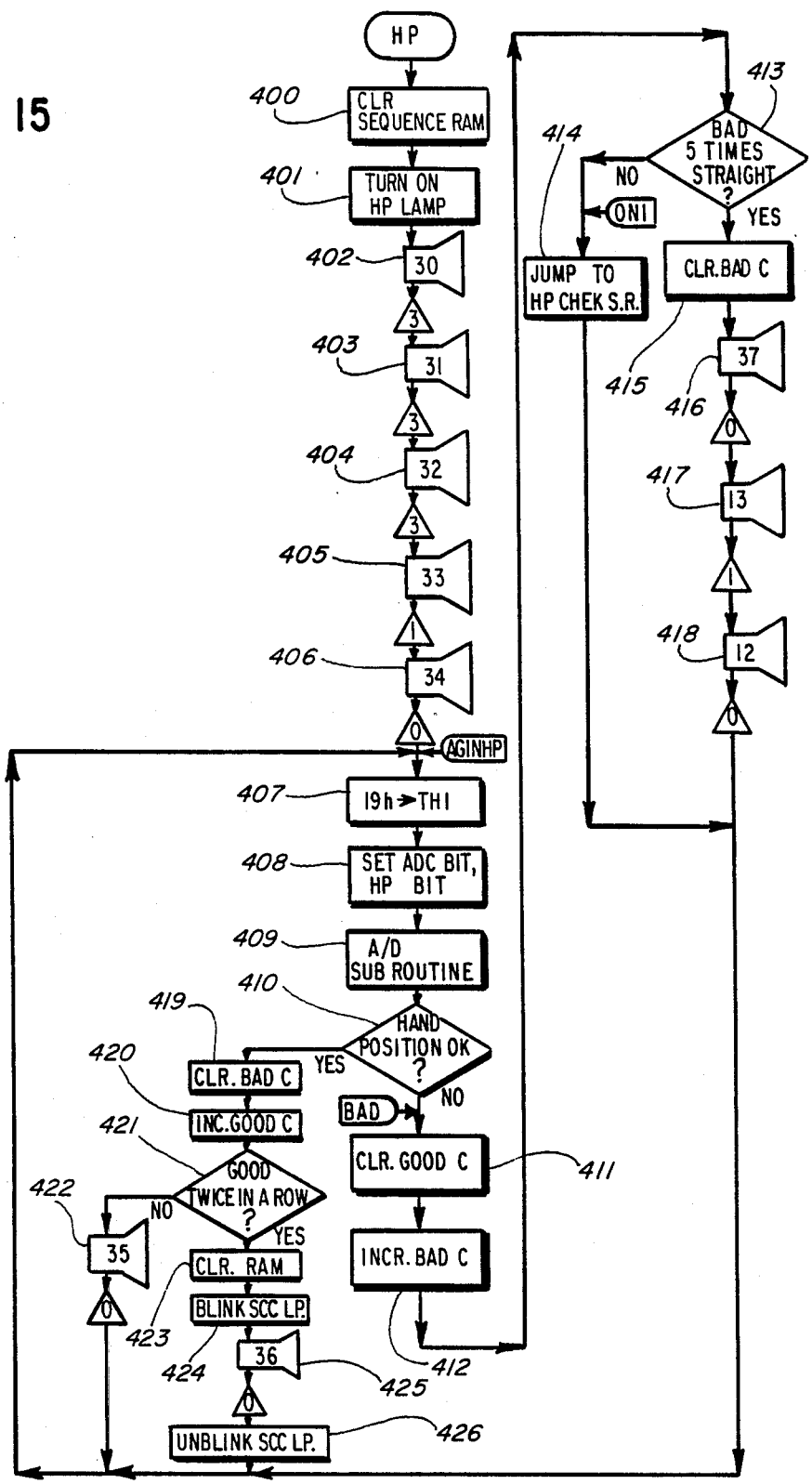
FIG. 15 is a flow chart for an embodiment of the Hand Placement Teaching Routine incorporated in the Control Program of FIG. 11.

FIG. 15 shows a flow chart of an embodiment of the Hand Placement Teaching Routine for practicing the correct position for the hand in chest compressions to restore circulation. The routine has the student reposition his hand and press down as many times as are needed to learn the correct location, giving feedback and advice each time. When the student can push down on the chest in the correct position twice in succession, he is encouraged to proceed to the Single Chest Compression routine.

The Hand Placement routine begins by clearing the microcomputer's RAM 82 (STEP 400) and turning on the Hand Placement lamp 56a. Then STEPS 402–406 voice Messages 30–34 which instruct the student how to position his hand on the manikin's chest as follows:

Hand position. Feel for the border of the manikin's ribs with the index and middle fingers of the hand closest to the manikin's waist. Move them upward along the rib cage until you reach the ribcage notch. Place the heel of your other hand just above the two fingers. Then place the first hand on top of it. Keep your fingers off the manikin's ribs. Push down, I will check your hand position.

STEP 407 sets a threshold value TH1 which a given chest compression sensor measurement must reach in order to exceed a background noise level before being recognized as an effort by the student. This threshold TH1 for practicing hand placement is set to hex 19 (decimal 25), corresponding to about 0.25 inches, which is about half the threshold used in practicing chest compressions, hex 32, corresponding to about 0.49 inches.

A bit called the ADC bit is set to 1 (STEP 408) to indicate that the A/D Conversion utility subroutine should read in analog data from the chest compression sensor 116 rather than the ventilation sensor 118. STEP 408 also sets a bit called the HP bit to 1 to indicate to the upcoming A/D utility subroutine that only hand position data (HPSTORE) is needed, not a maximum of chest compression (MAXVAL).

Then the A/D subroutine is called (STEP 409). When the A/D subroutine lights READY lamp 65, the student places his hand on the manikin's chest and tries pushing down. The A/D subroutine quickly takes a series of sample readings until the threshold TH1 has been exceeded. When the threshold has been passed, the A/D subroutine reads the positions of normally closed hand position switches S3, S6. S9, S12 of FIGS. 4 and 8C. Then it adjusts the four least significant bits HS0, HS1, HS2 and HS3 of a byte in memory called HPSTORE in accordance with the switch positions:

| If S3 is CLOSED, | HS0 = 1; | otherwise HS0 = 0 |
| If S6 is CLOSED, | HS1 = 1; | otherwise HS1 = 0 |
| If S12 is CLOSED, | HS2 = 1; | otherwise HS2 = 0 |
| If S9 is CLOSED, | HS3 = 1; | otherwise HS3 = 0 |

If STEP 410 determines that any of bits HS0, HS1, HS2, HS3 is a 0, the student's hand position is not acceptable. The routine goes to STEP 411 where the counter variable GOODC is cleared to zero and the counter variable BADC is incremented by 1 (STEP 412). If STEP 413 determines that there have not yet been five successive bad attempts at hand position (BADC is less than five), STEP 414 calls the utility subroutine Hand Position Check. The Hand Position Check subroutine immediately voices one or more corrective messages about the student's hand position:

| HPSTORE BIT | (CAUSED BY) | MESS # | MESSAGE |
|---|---|---|---|
| HS0 = 0 | (S3 OPEN) | 40 | Off Center |
| HS1 = 0 | (S6 OPEN) | 39 | Too Low! |
| HS2 = 0 | (S12 OPEN) | 38 | Too High |
| HS3 = 0 | (S9 OPEN) | 40 | Off Center |

Then STEP 414 voices Message 41: "Release compression! Try it again!" The routine then loops back to STEP 407 so the student can try positioning his hand again.

If at STEP 413 it is found that five bad attempts have accumulated in BADC, the student needs a fresh start with special instructor coaching. Counter variable BADC1 is cleared and Messages 37, 13, and 12 are voiced as follows:

Your hand position is not quite right. Please ask the instructor for help. Try it again.

Then the routine loops back to STEP 407 so the student can try positioning his hand again.

When STEP 410 determines that the student's hand position is acceptable, the routine goes to STEP 419 where the student's past mistakes are erased by clearing the counter variable BADC to zero. Then the counter variable GOODC is incremented by 1 (STEP 420). If STEP 421 determines that there have not yet been two successive acceptable attempts at hand position (GOODC is less than two), STEP 422 voices Message 35: "Fine. Remove and reset your hands. Try it again." Then the routine loops back to STEP 407 for a new try.

When STEP 421 determines that the student has achieved two successive acceptable hand position efforts (GOODC=2), STEP 423 clears the RAM. The Single Chest Compression lamp 59a is blinked (STEP 424) and Message 36 is voiced as follows (STEP 425):

Good, if you feel confident, you should now practice a single chest compression. If you don't, try it again.

STEP 426 then turns off the blinking Single Chest Compression lamp. Although the routine next loops back to STEP 407 for the student to try again, he can break out of the hand placement routine by pressing the selection button for another routine, such as the Single Chest Compression routine.

6. Single Chest Compression Routine

Figure 16:
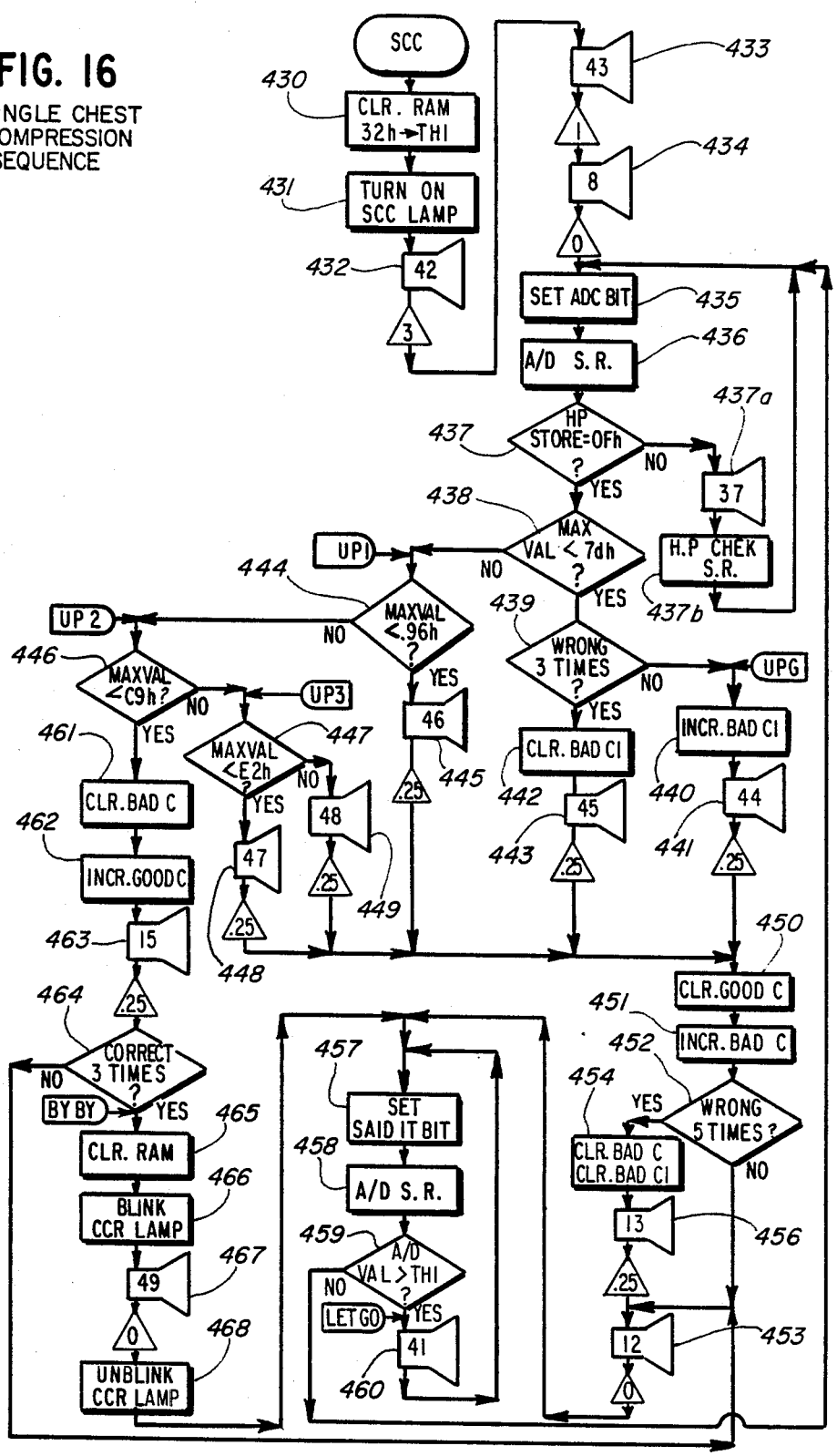
FIG. 16 is a flow chart for an embodiment of the Single Chest Compression Teaching Routine incorporated in the Control Program of FIG. 11.

FIG. 16 shows a flow chart of an embodiment of the Single Chest Compression (SCC) Teaching Routine for practice of chest compressions to restore circulation during cardiac arrest. The routine has the student practice doing single chest compressions of the correct depth, giving feedback and advice each time until the student can do three successive correct single compressions.

The SCC routine begins (STEP 430) by clearing the microcomputer's RAM 82 and setting a noise reducing threshold value TH1 given chest compression sensor measurement must reach before being recognized as an effort by the student. The threshold TH1 is set to hex 32, which corresponds to threshold of 0.49 inches. Values in Range A of FIG. 9B and Table 2 are below the threshold. To show which routine is running, the CHEST COMPRESSION DEPTH lamp 59a of FIG. 2 is turned on (STEP 431).

STEPS 432–434 voice Messages 42, 43, and 8 as follows, as instructions to the student for beginning chest compressions:

Single chest compression. Take the correct hand position, your elbows locked and your shoulders directly over the sternum. The chest should be compressed smoothly one and one half to two inches. Try a single chest compression. I will tell you how you did.

The ADC bit is set to 1 (STEP 435) to indicate that the A/D Conversion utility subroutine should read in analog data from the chest compression sensor 116 rather than the ventilation sensor 118. Then the A/D subroutine is called (STEP 436). The A/D subroutine turns on READY lamp 65 on control panel 53 (FIG. 2) so the student will know the system is ready to monitor his efforts.

When the student places his hands on the manikin's chest and tries a chest compression, the A/D subroutine quickly takes a series of sample readings of the chest compression sensor 116. When the student's chest compression has reached its maximum, the A/D subroutine sets a variable called MAXVAL equal to the A/D converted maximum value.

As described in connection with the Hand Placement Routine, the A/D subroutine also reads hand position switches S3, S6, S9, S12 and stores a hand position report in the four least significant bits of the byte in memory called HPSTORE. The A/D subroutine then returns control to the SCC routine.

If the student's hand position is correct, the four least significant bits of HPSTORE will all be 1's. Because the (unused) four most significant bits of HPSTORE are kept 0, HPSTORE will be hex 0F (binary 00001111) when the hand position is correct. If STEP 437 determines that HPSTORE is not hex 0F, STEP 437a voices Message 37: "Your hand position is not quite right." Then STEP 437b calls the Hand Position Check subroutine. As described in connection with the Hand Placement Routine, the Hand Position Check (HPCHEK) subroutine verbally reports what is wrong with the student's hand position (Too High, Too Low!, or Off Center). After the HPCHEK routine winds up with Message 41 ("Release compression! Try it again!"), the SCC routine loops back to STEP 435 for the student to try again until he gets the correct hand position.

When STEP 437 finds that HPSTORE is hex 0F, the hand position is correct and STEP 438 determines if MAXVAL is less than hex 7d (1.23 inches). If it is, the student's compression lies in Range B and is too shallow. If STEP 439 determines (from checking counting variable BADC1) that it is not yet the third time the student's attempt was in Range B, the counting variable BADC1 is incremented by 1 (STEP 440) and coaching Message 441 is voiced: "Too shallow." Then the routine proceeds to STEP 450.

On the other hand, if the student's attempts repeatedly fall in Range B, BADC1 will soon be incremented to a 2. In this case, after the third such shallow attempt STEP 439 switches control to STEP 442. Because of the successive errors, the student needs a fresh start and some advice. The variable BADC1 is cleared to zero and STEP 443 voices Message 45:

Too shallow! Be sure that you're pressing straight down, your elbows locked and your shoulders directly over the sternum.

Then the routine proceeds to STEP 450.

Should STEP 438 find that MAXVAL is equal to or greater than hex 7D, STEP 444 then determines if MAXVAL is less than hex 96. If it is, the student's effort lies in Range C (1.23–1.46 liters), still too little. Therefore, at STEP 445 Message 46 is voiced: "Close, but too shallow." Then the routine proceeds to STEP 450.

If instead STEP 444 determines that MAXVAL is equal to or greater than hex 96, STEP 446 determines if MAXVAL is less than hex C9 (1.96 liters). If it isn't, STEP 447 determines if MAXVAL is less than hex E2. If it is, the student's compression lies in Range E and is too deep. Therefore, STEP 448 voices Message 47: "Close but too deep." Then the routine proceeds to STEP 450.

But if STEP 447 determines that MAXVAL is greater than or equal to hex E2, the student's compression lies in Range F and is much too deep. Therefore, STEP 449 voices Message 48: "Too deep." Then the routine proceeds to STEP 450.

The acceptable range for chest compressions is 1.47–1.96 inches, Range D. Efforts in Range A will be below threshold. Efforts in Ranges B, C, E, and F all lead to STEPS 450 and 451, which clear counter variable GOODC (good count) and increment counter variable BADC (bad count).

STEP 452 checks variable BADC to see if 5 bad compressions have accumulated. If BADC is currently less than 5, the routine jumps to STEP 453. But if 5 bad ventilations have accumulated, the student needs a fresh start with special instructor coaching. STEP 454 clears counter variables BADC1 and BADC and STEP 456 voices Message 13: "Please ask the instructor for help." Then the routine proceeds to STEP 453.

If STEP 446 determines that MAXVAL is less than hex C9, then the student's attempt lies in Range D and is acceptable. Because the student has now produced a good compression, STEP 461 also erases his past learning errors by setting to zero the "bad count" counter variable BADC. STEP 462 increments counter variable GOODC (good count), and the student is praised at STEP 463: Excellent.

If STEP 464 determines from counter variable GOODC that three good ventilations have not yet been produced, the routine proceeds to STEP 453 for more practice.

STEP 453 uses Message 12 to direct the student to "Try it again." Then STEP 457 sets a bit called SAIDIT to 1 to indicate that a maximum of the student's effort has already been determined and a critique voiced.

The microcomputer's response may be so prompt that the student is still in the process of pressing on the manikin's chest, though the maximum of the compression has already occurred. Therefore, STEP 458 calls the A/D subroutine to read and convert the current instantaneous value of the compression sensor, and set the variable ADVAL equal to it. Because the SAIDIT bit is set, the A/D subroutine will just give the instantaneous reading ADVAL and not try to determine a maximum from a series of readings as before. The A/D subroutine also clears the SAIDIT bit to 0.

STEP 459 determines if ADVAL exceeds the threshold TH1. If it does, the student is not through compressing the manikin's chest. STEP 460 voices Message 41, "Release compression! Try it again!". Then the routine loops to STEP 457 to again set the SAIDIT bit and take another instantaneous reading.

When ADVAL falls below the threshold TH1 at STEP 459, the student is finished and ready to make a fresh effort. The routine loops back to STEP 435 to have the student do another compression.

Eventually the student will achieve three good compressions in a row. The counter variable GOODC will become 3 and at STEP 464 the routine will go to STEPS 465 and 466, which respectively clear the microcomputer's RAM 82 and blink the CHEST COMPRESSION RHYTHM lamp 60a. STEP 467 voices message 49: "Great, now practice chest compression rhythm or try it again." STEP 468 stops the blinking of lamp 60a.

The routine then proceeds to STEP 457 in case the student is still pressing on the manikin's chest. After clearing STEP 459, the routine loops back to STEP 435 for the student to try again. But the student can break out of the SCC routine by pressing the selection button for another routine, such as the Chest Compression Rhythm routine.

7. Chest Compression Rhythm Routine

FIG. 17 shows a flow chart of an embodiment of the Chest Compression Rhythm (CCR) teaching routine for practicing fifteen successive chest compressions at about 80-100 compressions per minute. The student is forced to restart if during any compression he uses an incorrect hand position or fails to come all the way up from the compression. As each chest compression passes its maximum, the student gets a word of praise or criticism. As soon as the fifteen compressions are completed the student receives a voice summary of how many compressions were excellent, too shallow, or too deep. The student is also is told if the rhythm of his fifteen chest compressions was excellent, too fast or slow, or irregular.

The CCR routine begins (STEP 470) by turning on the CHEST COMPRESSION RHYTHM lamp 60a. STEPS 471, 472 voice Messages 50 and 8 as follows, as instructions to the student for beginning this routine:

Chest compression rhythm. Give fifteen chest compressions smoothly, no bouncing, using a one and two and three and four ... to fifteen cadence. Come all the way up between compressions. I will tell you how you did.

The microcomputer's RAM 82 is cleared (STEP 473) and the threshold value for the chest compressions TH1 is set to hex 32, corresponding to 0.49 inches (STEP 474). Values in Range A of FIG. 9B will below the threshold.

The ranges above threshold, B, C, D, E, and F, have the respective maximum hex values 7C, 95, C8, and E1. These are respectively stored under the variable names ABLE, BAKER, CHUCK, and DOG (STEP 475), and then the ADC bit is set to 1 (STEP 476) to indicate that the A/D Conversion utility subroutine should read in data from the chest compression sensor 116. Then to tag the first chest compression, a bit 1STCC is set to 1 (STEP 477), and STEP 478 calls the A/D subroutine to get data on the student's hand position in HPSTORE and the maximum of the converted compression in MAXVAL.

As in the Single Chest Compression (SCC) routine (see STEP 437), the correct hand position is confirmed if HPSTORE is hex 0F (STEP 479). If it is not, a counter variable MAXC used to count which compression is currently being processed is cleared to 0 (STEP 480), and STEP 481 voices Message 37: "Your hand position is not quite right." STEP 482 calls the Hand Position Check (HPCHEK) utility subroutine 236, which verbally reports what is wrong with the student's hand position. After the HPCHEK routine winds up with Message 41 ("Release compression! Try it again!"), the CCR routine loops back to STEP 473 for the student to begin again with the correct hand position.

If the hand position is correct at STEP 479, an eight-bit timer mechanism on board microcomputer 80a is configured or initialized (STEP 483) so when started it will use the 125 Hz timer clock input at the microcomputer's TIMER input from frequency divider 113 of FIG. 4. In FIG. 4 the timer mechanism in microcomputer 80a is represented by its eight bit timer data register TDR, which can be read for the current value of the on board timer.

If the 1STCC bit is set (STEP 484), the current compression is the first of the 15 and STEPS 486 and 487 can be omitted. The 1STCC bit is cleared, and the routine proceeds to STEP 488, where the microcomputer's timer is started. Just a few steps earlier, the A/D subroutine called by STEP 478 will have returned immediately after finding a maximum in the depth of the student's compression. Microcomputer 80a is running at 8.0 MHz. Therefore, to a good approximation in determining the period of the compression, STEP 488 starts the microcomputer's timer immediately after a compression has reached its maximum depth.

In a manner similar to that used in the Ventilation routine (see STEP 370), STEP 489 now calls scoring subroutine SCORC1 to immediately comment on the value of MAXVAL (compression maximum) obtained by the A/D subroutine at STEP 478:

TABLE 4

OUTPUT OF SCORC1

| MAXVAL (HEX) | RANGE | CHEST COMPRESSION (INCHES) | BRIEF CRIT. | MESS. # | COUNTER INCREMENTED |
|---|---|---|---|---|---|
| 32–7C | B | 0.49–1.22 | MORE! | 19 | CBIN1 |
| 7D–95 | C | 1.23–1.46 | MORE | 20 | CBIN1 |
| 96–C8 | D | 1.47–1.96 | GREAT | 21 | CBIN2 |
| C9–E1 | E | 1.97–2.21 | LESS | 22 | CBIN3 |
| E2–FF | F | 2.22–2.50 | LESS! | 23 | CBIN3 |

As can be seen in Table 4, the SCORC1 subroutine also accumulates the number of compressions that are too shallow, acceptable, and too deep by incrementing corresponding counter variables CBIN1, CBIN2, and CBIN3.

The student will now be occupied in trying to maintain a steady rhythm for 15 successive chest compressions at a rate that may leave as little as 0.6 second for each compression. It is an important feature of the invention that the one word brief criticisms of Table 4 can be voiced in about 0.3 second, enabling feedback by a prestored natural human voice having inflection, tone, volume and urgency.

As in the Single Chest Compression routine (see STEPS 457–460), the student must come up all the way from each compression. STEPS 490–493, 495–497 verify this using the A/D subroutine. The SAIDIT bit is set to 1 (STEP 490), enabling the A/D subroutine to determine ADVAL, the current instantaneous value of the compression sensor (STEP 491). The A/D subroutine also clears the SAIDIT bit to 0. STEP 492 determines if ADVAL is less than a Release Level of hex 2D (decimal 45), slightly less compression than the Threshold TH1. If ADVAL is not less than the Release Level, the timer data register TDR is read (STEP 493) to determine the interval since the last maximum of compression.

Table 5 is a Timer Conversion Table for the timer data register TDR. The microcomputer's timer receives a 125 kHz timer clock signal (clock pulse every 8 ms). This decrements the timer data register TDR every 8 ms from an initial value of hex 00 (interpreted as decimal 256). For example, it takes 49 clocks to decrement register TDR from hex 00 to hex CF, measuring an interval of 392 ms (49×8 ms).

TABLE 5

TIMER CONVERSION TABLE

| TIMER DATA REGISTER (HEX) | TIMER READING (DEC) | ELAPSED 8 MS CLOCKS | ELAPSED TIME MS | COMPRESSION. FREQUENCY PER/MIN |
|---|---|---|---|---|
| 00 | 256 | 0 | 0 | — |
| FF | 255 | 1 | 8 | — |
| CF | 207 | 49 | 392 | 153 |
| B5 | 181 | 75 | 600 | 100 |
| A2 | 162 | 94 | 752 | 79.8 |
| 83 | 131 | 125 | 1000 | 60 |
| 40 | 64 | 192 | 1536 | 39 |
| 00 | 0 | 256 | 2048 | 29 |

At the lowest acceptable rate, 80 compress/minute, the peak-to-peak period for one compression will be 750 ms, and the time from a maximum to a minimum will be a half period of 375 ms. STEP 495 uses a reading of timer data register TDR (STEP 493) to determine if the interval since the last maximum of compression is greater than a Cutoff of 392 ms (a Cutoff interval slightly more than the 375 ms half period associated with 80 compressions per minute.) This is equivalent to asking, "Is register TDR less than hex CF?"

If more than 392 ms have not elapsed since the last compression maximum, the routine loops back to STEP 490 for a new reading of ADVAL. If STEP 495 determines that more than 392 ms have elapsed, the student is not coming up all the way in releasing the compression. STEPS 496, 497 then voice Messages 73 and 74:

Come all the way up between compressions.

Give fifteen chest compressions again.

Then the CCR routine loops back to STEP 473 for the student to restart the series of fifteen compressions.

If the student is coming up all the way between chest compressions, at STEP 492 ADVAL will become less than hex 2D before 392 ms have elapsed. The routine will proceed to STEP 498, which determines, from the value of a counter variable MAXC, if there have been 14 previous compressions. If there haven't, the counter variable MAXC is incremented at STEP 499, and the routine loops back to STEP 478 so the student's next compression can be processed.

After the first compression, bit 1STCC will not be set to 1 when STEP 484 is reached. Therefore, STEP 486 will read register TDR to determine a compression period in accordance with Table 5. For example, at STEP 486 the TDR register might be found to have been decremented to hex B5. In such case, 600 ms would have elapsed between the previous maximum (when the timer was started) and the current maximum. In a series of fifteen compressions, the peak-to-peak period can be measured fourteen times in this way. Each measured compression period is stored in memory in one of 14 bytes called PERIOD(MAXC), where MAXC is an index integer incremented from 1 to 14 as the routine repeatedly passes through STEP 499 for successive compressions.

As each successive measured period is determined at STEP 486, a running total is calculated at STEP 487 in the form:

Let TOTAL=TOTAL+PERIOD (MAXC)

where the expression on the right is evaluated first and then replaces TOTAL, and MAXC is the previously mentioned integer index variable indicating the most recently measured period.

Eventually, index variable MAXC will be incremented to 14. Then the next (15th) time a compression maximum is measured and the routine executes STEP 498, the CCR routine will proceed to step 500. Beginning at this step some elementary statistics are calculated for the 14 measured compression periods, here denoted as $P_i$. A simple mean of P is computed (STEP 500) as follows:

$$\overline{P} = \frac{\sum\limits_{i=1}^{14} P_i}{14} \quad \text{(Eq. 1)}$$

In fact, $\overline{P}$ can be calculated by dividing the variable TOTAL, which already equals the sum of the fourteen measured periods, by fourteen.

Then STEP 501 makes a computation, somewhat like that used for calculating the standard deviation, to determine SIGMA, an estimate of how much the 14 individual measured periods differ from the average:

$$\text{SIGMA} = \frac{\sum\limits_{i=1}^{14} |P_i - \overline{P}|}{14} \quad \text{(Eq. 2)}$$

Equation 2 is introduced for computational simplicity, since only an estimate of the standard deviation is needed. However, if desired, microcomputer 80a can be suitably instructed to calculate the precise mathematical standard deviation, since it has sufficient computational power. As a housekeeping measure, the index variable MAXC is set to zero (STEP 502).

As mentioned in connection with STEP 489, during the fifteen compressions the SCORC1 subroutine accumulates the number of compressions that are too shallow, acceptable, and too deep by incrementing corresponding counter variables CBIN1, CBIN2, and CBIN3 (Table 4). Now STEP 503 calls the SCORC2 utility subroutine to select from among Messages 51-66 to report the results as follows:

| | |
|---|---|
| (CBIN1) | were too shallow. |
| (CBIN2) | were great. |
| (CBIN3) | were too deep. | where the appropriate number stored in the counter variable is voiced. Of course, if the number for any category is zero, there is no message about it.

Similarly, at STEP 504 the SCORC3 subroutine is called to report on the speed and evenness of the student's compression rhythm, based on the computations of STEPS 500 and 501. In fact, since the readings of the timer data register TDR at STEP 486 have a linear relationship to the compression period, the computations of Equations 1 and 2 (which are also linear) can be done on the TDR readings themselves. These can then be interpreted by Table 6:

TABLE 6

| INTERPRETATION OF AVERAGE TDR READING | | |
|---|---|---|
| AVERAGE PERIOD (MS) | AVERAGE TDR READING | WORDS USED IN MESSAGE |
| <600 | >B5 | Rhythm is too fast. |

TABLE 6-continued

| INTERPRETATION OF AVERAGE TDR READING | | |
|---|---|---|
| AVERAGE PERIOD (MS) | AVERAGE TDR READING | WORDS USED IN MESSAGE |
| 600-752 | B5-A2 | Excellent rhythm. |
| >752 | <A2 | Rhythm is too slow. |

When Equation 2 is applied to the TDR readings themselves, if the resulting SIGMA is equal to or greater than hex 5 the compression rhythm is voiced as "Irregular". Since the timer clock pulses are spaced 8 ms apart, this corresponds to a SIGMA equal to or greater than 40 ms.

As can be seen from Messages 67-72, SCORC3 reports about the rhythm speed and regularity together in a single appropriately selected combined message. A typical message used by SCORC3 that combines the speed and rhythm comments is Message 67:

Rhythm is too fast and irregular.

SCORC2 sets a bit called SCBIT to 1 if CBIN2<10, i.e., less than 10 of the 15 compressions have the proper depth. If STEP 505 finds this bit is 1, the bit is cleared to 0 (STEP 506) and STEP 507 voices Message 74: "Give fifteen chest compressions again." Then the routine loops back to STEP 473 for the student to redo the fifteen compressions. Similarly, SCORC3 sets a bit called RHYTHM BIT to 1 if the rhythm is slow, fast, or irregular. If STEP 508 finds this bit is 1, the bit is cleared to 0 (STEP 509) and the routine proceeds to STEP 507.

If neither the SCBIT nor the RHYTHM BIT is set, the student's performance is satisfactory. The routine proceeds from STEP 508 to turn on the HEIMLICH THRUST lamp 61a (STEP 510), and STEP 511 voices Message 76:

If you feel confident, practice clearing the airway. If you don't, give fifteen chest compressions again.

Then the HEIMLICH THRUST lamp is turned off (STEP 512), and the CHEST COMPRESSION RHYTHM lamp is turned back on (STEP 513). Although the routine loops back to STEP 473 for the student to try again, he can break out of the CCR routine by pressing the selection button for another routine, such as the Heimlich Thrust routine.

8. Heimlich Thrust Teaching Routine

Figure 18:
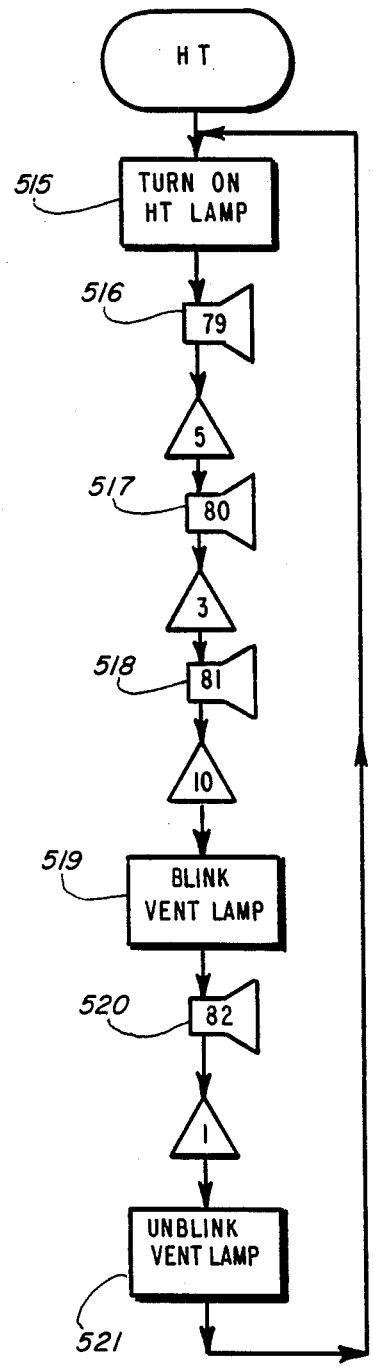
FIG. 18 is a flow chart for an embodiment of the Heimlich Thrust Teaching Routine incorporated in the Control Program of FIG. 11.

FIG. 18 shows a flow chart of an embodiment of the Heimlich Thrust Teaching Routine for practice in clearing the manikin's airway of an obstruction, such as a piece of food. No measurements are made in this routine, but the student practices abdominal (Heimlich) thrusts on the manikin. However, if desired, the manikin can be fitted with suitable sensors for this routine, such as strain gages just above the navel. If such sensors are installed, the teaching routine can be elaborated to use and report the sensor data in a manner similar to the other teaching routines.

STEPS 515-518 respectively turn on the Heimlich Thrust lamp 61a and voice Messages 79-81:

Clearing the airway. Kneel astride the manikin's thighs. Place the heel of one hand slightly above the navel. Place the other hand on top of it. Press into the abdomen with quick upward thrusts. Each thrust should be distinct and delivered with the intent of clearing the airway. Do it ten times.

Then the AIRWAY VENTILATION lamp 58a is blinked (STEP 519) and STEP 520 voices Message 82: "When you feel confident, practice ventilating the manikin." Then the blinking of the AIRWAY VENTILATION lamp is halted. Although the routine loops back to STEP 515 for the student to try abdominal thrusts again, he can break out of the Heimlich Thrust routine by pressing the selection button for another routine, such as the Airway Ventilation routine.

9. Storage of Messages and Phrases a. Message Coding and Storage

FIG. 19 shows how voice messages and phrases are stored in memory. Each voice message is identified by a sequential message identification number 525 (Message Nos. 1, 2, 3, ... ). A message 530 is composed of a series of short (less than 1 second) preselected phrases 546. The preselected phrases 546 are stored in a speech memory 527, external to the microcomputer unit. The speech memory can be implemented by a read only memory (ROM), such as a ROM semiconductor memory. In practice, a programmable read only memory (PROM) that can be programmed once, or an erasable programmable read only memory (EPROM) can be used for the speech memory.

By "phrase" is meant not the conventional linguistic unit, but any short sequence of sound which is, from an engineering point of view, convenient for encoding and storage. Thus, as used here a "phrase" may be a part of a word, a whole word, a linguistic phrase, or any portion of a linguistic phrase. Examples of such phrases are "PINCH_OFF", "THE_MANIKIN'S", "NOSTRIL", and "S".

For message coding purposes, each phrase is uniquely identified by an 8-bit (1 byte) phrase identification number 528. An eight-bit identification number provides for up to 256 different preselected phrases.

A message is specified by the particular series of 1-byte phrase identification numbers designating the phrases making up the message. For example, the message "PRESS DOWN" is composed of the phrases "PRESS" and "DOWN". If the phrase identification number for "PRESS" is 01110101 and the phrase identification number for "DOWN" is 11111001, the message "PRESS DOWN" is specified by the two bytes 01110101, 11111001 .

A Message Composition Table 529, in which the messages 530 are sequentially stored, is provided in memory to hold the make-up of each message in terms of a series of 1-byte entries 531, each a phrase identification number, designating the phrases in the appropriate sequence to compose the message. The present embodiment provides for about 82 different messages, though this number can be increased if desired. Although the messages are of various different lengths, the capacity of the Message Composition Table 529 is sufficient to allow for an overall average length of up to 9 phrases per message. Since it takes 1 byte (8 bits) to identify each phrase in a message, the entire Message Composition Table can be only 738 (82×9) bytes long, enabling the Table to be stored in the onboard EPROM memory of the microcomputer unit.

A Message Index 532 is provided in memory to help locate the bytes composing a particular message stored in the Message Composition Table. The Message Index has 82 entries, corresponding to the 82 possible message identification numbers. The index entry 533 corresponding to a particular message number is a 16-bit (2 byte) message locating number 534. Thus, the entire Message Index is only 164 (82×2) bytes long, enabling it also to be stored in the onboard EPROM memory of the microcomputer unit.

In the first byte 535 of the message locating number, the six most significant bits (MSB's) 536 are read as a binary number indicating how many 1-byte phrase identification numbers compose the message. The six bits provide for messages composed of as many as $2^6=64$ preselected phrases.

To facilitate addressing with an 8-bit address bus, the 768 bytes of the Message Composition Table are subdivided into three smaller 256 byte Tables L, M, and N. The two least significant bits (LSB's) 537 of the first byte are read as a code indicating which of the Tables L, M, or N holds the message in question. The two-bit code is 00=L Table, 01=M Table, 10=N Table.

The second byte 538 of the message locating number is read as an 8-bit number 539 indicating the address location, in the appropriate table L, M, or N, where the first phrase identification number (a 1 byte number) of the message is stored. The remaining phrase identification numbers of the message follow in sequence.

In sum, given a message number, the Message Index gives the location and length of that message as encoded in the Message Composition Table. At the specified location in the Message Composition Table is a series of phrase identification numbers, each entry one byte long, which compose the message.

b. Phrase Coding and Storage

As each phrase is identified by a 1-byte phrase identification number, this provides for up to 256 preselected phrases. Each phrase is composed of a series of audio nibbles 544 stored in the speech memory. A nibble is a binary number of four bits, i.e. one-half byte long. It is convenient to use a speech memory that stores a byte (an 8-bit number) at each address. Therefore, the audio nibbles are grouped in pairs so that they can be stored and retrieved in bytes 545.

These audio nibbles are obtained by sampling an actual voice input signal for the phrase concerned and converting the sampled values to digital nibbles for later reproduction by a suitable speech synthesizer. Special equipment (not shown) for coding speech as binary numbers is commercially available, such as the SAS-1 Real-Voice Memory Processor sold by OKI Semiconductor of Santa Clara, Calif. In effect, such a speech encoder makes it possible to digitally prerecord sounds as nibbles, storing them in the speech memory for later reproduction.

The speech encoder of the OKI Processor (not shown) uses adaptive differential pulse-code modulation (ADPCM), a very efficient method of analog-to-digital conversion of a sampled analog signal. The OKI processor can be configured to take 8,000 samples per second of an input real voice audio signal. This permits the frequency of the sampled and stored voice audio to be as high as 4,000 Hz, i.e. half the sampling frequency, which is adequate to provide very natural-sounding voice reproduction.

In response to each sample, the speech encoder of the OKI Processor outputs a 4-bit (1 nibble) binary number. Since a nibble is one half byte, the sampling produces 4,000 bytes each second for storage in the speech memory 527. In other words, it takes 4,000 bytes stored in the speech memory to digitally store a phrase 1 second long.

In dealing with computer memories, it is common to work with a unit of measure equal to 1024 bytes, called a "kilobyte" or "KB" of memory. Therefore, a one-second phrase, when sampled, takes up about 4 KB (4 kilobytes) in the speech memory.

There are about 256 phrases 546 of different lengths stored in the speech memory 527. Although any one phrase can be as long as 4KB (1 second), overall average duration is no more than 1.5 KB (0.375 seconds) per phrase. Therefore, the speech memory need have a capacity of only 384 KB (256×1.5K) to hold all the sampled phrases, which is a total of about 96 seconds of voice sounds.

Such a speech memory can be conveniently and inexpensively implemented from EPROM chips that have a 16-bit address input and that store 64KB each. Such EPROM chips are commercially available from Fujitsu (its memory chip 27C512) and others. The 16-bit address line provides for $2^{16}$ (64×1024) different address locations, each of which can store 1 byte of information. Six of these commercially available 64 KB EPROM chips will provide the 384KB speech memory capacity needed to store all the sampled phrases.

To play back the recording of a particular phrase, the audio nibbles making up the phrase are read from the speech memory and inputted one at a time to a digital-to-analog (D/A) speech synthesizer matched to reproduce the phrase as an audio signal. For this purpose, a matching ADPCM speech synthesizer integrated circuit chip is available from Oki Semiconductor: speech synthesizer chip MSM 5218.

The output of the speech synthesizer chip is passed through a low-pass filter having a high-frequency cutoff of about 4 kHz, amplified, and passed to an output speaker. For example, the low-pass filter can be conveniently implemented from a digital low-pass filter integrated circuit chip, such as National Semiconductor's MF6CN100, and the audio amplifier can also be any suitable amplifier circuit, such as National Semiconductor's LM388N2 integrated circuit amplifier chip.

A Phrase Index 548 is provided in memory to help locate the nibbles composing a particular phrase stored in the speech memory. The Phrase Index has 256 entries, corresponding to the 256 possible phrase identification numbers. The index entry corresponding to a particular phrase number is a 32-bit phrase locating number 549 occupying four successive bytes. Thus, the entire Phrase Index is only 1024 (256×4) bytes long, enabling it to be stored in the onboard EPROM memory of the microcomputer unit.

The 32-bit (4 bytes long) phrase-locating number 549 has two parts, a 20-bit phrase address 550 and a 12-bit phrase-length indicator 550a. In other words, given an 8-bit phrase identification number, of value 0–255, the Phrase Index gives the location and length of that phrase as stored in the speech memory. At the specified location in the speech memory is a series of bytes that contain the nibbles which store the phrase.

The 20-bit phrase address enables 550 up to $2^{20}$ addresses, a million memory addresses, to be individually specified. This is more than adequate to address any of the 384 kilobytes of speech memory. To facilitate addressing memory chips having a 16-bit address bus, the first 16 bits of the phrase address are interpreted as a 16-bit address in one of the six 64-KB speech memory chips. These 16 bits of the phrase address are found in the first two bytes 551, 552 of the phrase-locating number The remaining 4 bits of the phrase address are interpreted as a binary number, starting with zero, indicating the particular chip (0, 1, 2, 3, 4, 5) in which the phrase is stored. In the embodiment described, these 4 bits are the four least significant bits 553 of the third byte of the phrase-locating number.

Even though the phrases are stored as audio nibbles, the 12 bit phrase-length indicator 550a specifies the phrase length in bytes. That is, the phrase length is specified to the nearest byte. A 12-bit phrase-length indicator number enables a phrase as long as 4KB ($2^{12}$ bytes) to be specified. In the embodiment described, the four most significant of these 12 bits are the four most significant bits 554 of the third byte of the phrase-locating number. The eight least significant of these 12 bits are the fourth byte 555 of the phrase-locating number.

In sum, given an 8-bit phrase-identification number, of decimal value 0–255, the Phrase Index gives the location and length of that phrase as stored in the speech memory. At the specified location in the speech memory is a series of bytes that contain the nibbles from which the phrase can be reproduced by the speech synthesizer chip.

c. Pause Coding

In natural speech, there are pauses (silence periods) between adjacent syllables or words that must be accounted for in coding the messages and the phrases used to form the messages. For example, the word "WELCOME" may be pronounced with a short pause, on the order of 60 milliseconds, between the syllables "WEL" and "COME". IF such a 60-millisecond pause is inputted to a speech encoder outputting 4 kilobytes of speech code per second, the 0.060 second pause would cause the output of 240 bytes of "pause" (no sound) nibbles for storage in the speech memory. This would be a very inefficient way to encode a "no sound" interval or pause. Therefore, three more efficient ways are used to encode pauses in the stored messages and phrases.

First, the 8-bit phrase-identification numbers are assigned to phrases in a way that indicates if there is normally a pause after the phrase. The two least significant bits (LSB's) of the 8-bit phrase-identification number are used as a code to assign the phrase to one of four subdivisions of the Phrase Index, called the S, T, U and V Tables. This 2-bit code is as follows:

| 2 LSB's | Table | Pause |
|---------|-------|-------|
| 00 | S | none |
| 01 | T | 32 ms |
| 10 | U | 64 ms |
| 11 | V | 128 ms |

First, when processing a phrase for reproduction, the two least significant bits of the phrase-identification number can be used as a control code to turn off the speech synthesizer for a suitable number of milliseconds after the phrase is synthesized, creating the desired pause.

The remaining six bits (six most significant bits) of the phrase-identification number enable up to 64 different phrases to be specified in each table.

Second, eight of the 8-bit phrase identification numbers are not used to identify phrases, and instead these eight numbers are reserved as pause-control codes. When a pause-control code is inserted in the message composition table before a phrase-identification number, the control code modifies the pause interval following the phrase represented by the phrase-identification number. For example, if a phrase-identification number belongs to Table S above, normally there is no pause after the phrase it identifies. But if a control code (e.g., 11111001) is inserted before the phrase-identification number, a 32-ms pause specified by the control code follows the phrase.

The pause control codes are inserted as needed before phrases when messages are encoded in the Message Composition Table. As the phrase-identification numbers composing a message are read out of the Message Composition Table, each control code is detected by the message processor, which then effectuates the necessary pause after the phrase which follows the control code.

The following phrase-identification numbers are reserved as pause control codes:

| Binary Number | Hex Value | Decimal Value | Pause Length |
|---|---|---|---|
| 11111000 | F8 | 248 | none |
| 11111001 | F9 | 249 | 32 ms |
| 11111010 | FA | 250 | 64 ms |
| 11111011 | FB | 251 | 128 ms |
| 11111100 | FC | 252 | 384 ms |
| 11111101 | FD | 253 | 2 sec |
| 11111110 | FE | 254 | 4 sec |
| 11111111 | FF | 255 | 8 sec |

The third method of adding or increasing pauses is to insert wait instructions in the control programs for the microcomputer unit before or after instructions calling for message reproduction. For example, a program instruction might call for Message #5, "PINCH OFF THE MANIKIN'S NOSTRILS," to be voiced by the speech synthesizer. Suppose a pause is needed after this message to allow the student time to respond before voicing the next coaching message. The pause can be introduced by following the instruction to voice Message #5 with an instruction to wait a predetermined number of milliseconds or seconds.

The wait instruction can be a suitable WAIT subroutine called whenever a pause is needed, provided that for the subroutine's reference a number indicating the desired length of the pause is first inserted in a suitably accessible register or memory location before calling the WAIT subroutine.

In sum, the identification number of a phrase indicates if the speech synthesizer should normally add a preselected pause after reproducing the phrase. In addition, some of the bytes composing a message in the Message Composition Table may be pause control codes for modifying the normal pause of the phrase that follows them. Pauses may also be introduced between messages by inserting a WAIT instruction in the microcomputer unit's control program.

10. Message Subroutine a. General Flow

This subroutine plays a message whose message number is held in the X register when the subroutine is called. If the PLAOLD bit has been set, the message is a repeat of the previously played message.

To play a message, first, the preselected phrases which compose the message are determined. Then for each phrase, the encoded audio nibbles of the phrase prestored in the speech memory must be read out as input to the speech synthesizer chip. The synthesizer chip uses this input to reproduce each phrase as an audio output signal for the amplifier and speaker.

To determine which phrases compose the message, the message number in the X register is used to compute an input address in the Message Index. The entry at that address gives the starting location and length of the message as encoded in the Message Composition Table. At the specified location in the Message Composition Table is a series of phrase identification numbers and pause control codes, each one byte long, which are read out of memory to indicate which phrases compose the message.

As each byte of a message is read out of the Message Composition Table, it is examined to determine whether it is a pause-control code or a phrase-identification number. If it is a pause-control code, the normal pause of the phrase that follows, represented by its phrase identification number, will be accordingly altered.

If the byte read out of the Message Composition Table is a phrase-identification number, it is used to determine where the audio nibbles of that phrase are located in the speech memory. It is also used to determine if after reproducing the phrase the speech synthesizer should normally be turned off for a specified interval to add a preselected pause.

An input address to the Phrase Index is computed from the phrase-identification number. The entry at that input address gives the starting address and number of bytes in the speech memory of the series of bytes which store the phrase. Each byte in the speech memory holds an adjacent two of the audio nibbles which compose the phrase. After each byte of the phrase is read out from the speech memory, the two nibbles it contains are inputted in message order, one at a time, to the speech synthesizer.

b. Detailed Operation

The subroutine is entered (STEP 561) with the number of the message to be played held in the X register. This number is read and stored as MESSNUM (STEP 562). Next a bit called PLAOLD BIT (play old message) is read (STEP 562) and checked (STEP 563). If the PLAOLD BIT is 0, the message is a new message. To enable the message to be repeated at a subsequent time (by pressing the REPEAT MESSAGE button on the control panel of FIG. 2), the variable LASTMS (last message) is set equal to the message number in the X register (STEP 564), and the routine proceeds to STEP 565.

If at STEP 563 the PLAOLD BIT is found to be 1, the message is a repeat of the last message, and there is no need to update the variable LASTMS, so there is a jump to STEP 565.

In either case, based on the message number MESSNUM a table look-up is performed using the Message Index to obtain the starting message address MESSADDRESS and the number of bytes (or message length MESSLENGTH) of the message as stored in the Message Composition Table (STEP 565).

The first byte of the message is then read from the Message Composition Table at the address MESSADDRESS and the variable BYTE is set to that value (STEP 566). As stored in the Message Composition Table, each byte of a message is either a phrase identification number or a pause control code.

If at STEP 567 the number BYTE is determined to not be greater than the hex number F7 (decimal 247), it is interpreted as a phrase-identification number. The two least significant bits of BYTE are then read (STEP 568) as a binary code indicating the pause length SILENCE that should follow the phrase in question when reproduced by the speech synthesizer:

| CODE | SILENCE |
|------|---------|
| 00   | 0 ms    |
| 01   | 32 ms   |
| 10   | 64 ms   |
| 11   | 128 ms  | routine then proceeds to STEP 572.

On the other hand, if at STEP 567 the number BYTE is determined to be greater than hex F7, it is interpreted as a pause-control code. The three least significant bits of BYTE are then read (STEP 569) as a binary code indicating the pause length SILENCE that should follow the phrase whose identification number comes next after the pause-control code:

| CODE | SILENCE | CODE | SILENCE |
|------|---------|------|---------|
| 000  | 0 ms    | 100  | 384 ms  |
| 001  | 32 ms   | 101  | 2 secs  |
| 010  | 64 ms   | 110  | 4 secs  |
| 011  | 128 ms  | 111  | 8 secs  |

If the number BYTE is a control code, then in order to indicate the address of the phrase identification number which follows it, the variable MESSADDRESS is incremented (STEP 570). At the same time, the variable MESSLENGTH, which keeps track of the number of bytes remaining in the coded message, is decremented.

The next byte of the message is then read from the Message Composition Table using the current value of MESSADDRESS as the address. The variable BYTE is set to that value (STEP 571), and the routine proceeds to STEP 572.

At STEP 572 the current value of BYTE is interpreted as a phrase identification number, and the variable PHRASENUM (phrase identification number) is set equal to it. Based on the phrase identification number PHRASENUM a table look-up is performed using the Phrase Index to obtain the starting phrase address PHRASEADDRESS and the number of bytes (or phrase length PHRASELENGTH) of the message as stored in the Speech Memory.

The first byte of the phrase is then read from the Speech Memory at the address PHRASEADDRESS and the variable SOUNDBYTE is set to that value (STEP 573). As the sounds of a phrase are coded in nibbles, the 4 most significant bits of SOUNDBYTE are read as NIBBLE1 and the 4 least significant bits as NIBBLE2 (STEP 574). Each of these nibbles is fed in turn to the sound synthesizer and the sampled sound corresponding to each nibble synthesized as the manikin's voice output for the speaker 66 (STEP 575).

The variable PHRASEADDRESS is incremented (STEP 576). At the same time, the variable PHRASELENGTH, which keeps track of the number of bytes remaining in the coded phrase, is decremented. If the current value of PHRASELENGTH is not yet zero, the routine jumps back to STEP 573 to read and synthesize the next coded byte of the phrase (STEP 577).

If, on the other hand, PHRASELENGTH has been reduced to zero by STEP 577, all coded bytes of the phrase have been read and synthesized. The routine moves to STEP 578 and a sound pause or interval of silence is maintained for the interval specified by variable SILENCE.

To move on to the next byte of the message in the MESSAGE COMPOSITION TABLE, the variable MESSADDRESS is incremented (STEP 579). At the same time, the variable MESSLENGTH, which keeps track of the number of bytes remaining in the coded message, is decremented (STEP 580).

If the current value of MESSLENGTH is not yet zero, the routine jumps back to STEP 566 to read and synthesize the next coded byte of the message. On the other hand, if MESSLENGTH has been reduced to zero by STEP 580, the subroutine has completed playing the MESSAGE indicated in the X register, and a RETURN to the routine which called it is executed at STEP 581.

11. A/D Conversion Subroutine

FIG. 21A shows a flow chart for an embodiment of the A/D Conversion Subroutine. This combined utility subroutine reads and converts to digital format the analog signals from the ventilation sensor 118 or chest compression sensor 116, as well as reading data from hand position switches S3, S6, S9, and S12. Before calling the subroutine, a variable TH1 is set to a noise threshold for the sensor signal.

The states of three reference bits, ADC, SAIDIT, and HPBIT at the time the subroutine is called determine which functions the A/D subroutine performs. The ADC bit determines whether chest compression sensor data (ADC=1) or ventilation sensor data (ADC=0) is read and converted. The SAIDIT bit determines whether the current instantaneous value (SAIDIT=1) or a local maximum (SAIDIT=0) of the sensor signal is to be provided. The instantaneous value is returned in a variable ADVAL (A/D value) and the local maximum is returned in a variable MAXVAL (maximum value). If HPBIT is 1, hand position switch data is to be returned, in a variable HPSTORE (hand position store).

The microcomputer's RAM 82 (STEP 585) is cleared, and READY lamp 65 on control panel 53 of FIG. 2. is turned on (STEP 586) to prompt the student to begin his efforts. The conversion is begun (STEP 587), and continued until data from both the ventilation sensor 118 and chest compression sensor 116 is separately converted by respective A/D converters 119 and 117 (STEP 588). If the ADC bit is a 1, the output of compression A/D converter 117 is read in to microcomputer 80a (STEPS 589, 590); otherwise, the output of ventilation A/D converter 119 is read in (STEP 591).

The sensor data which has been read in is latched (STEP 592), and then stored in two variables, SMPNEW (sample new) (STEP 593) and ADVAL (STEP 594). If the SAIDIT bit is not set, the threshold value TH1 is loaded in the accumulator (STEP 596) and compared with SMPNEW (STEP 597). If SMPNEW (the student's sampled effort) does not yet equal or exceed TH1, the subroutine loops back to STEP 587 to begin another conversion.

FIG. 21B shows a typical sensor signal as a function of time in the case where SMPNEW exceeds the threshold TH1. Although the microcomputer actually deals with a quantized digitally converted sensor signal, since the quantization is relatively fine (256 levels), this detail is not shown in FIG. 21B.

When SMPNEW is equal to or greater than TH1 at STEP 597, data from the hand position switches S3, S6, S9, S12 is read in (STEP 598), and stored (STEP 599) in the four least significant bits HS0, HS1, HS2, HS4 of an eight-bit variable HPSTORE as follows:

| | | |
|---|---|---|
| If S3 is CLOSED, | HS0 = 1; | otherwise HS0 = 0 |
| If S6 is CLOSED, | HS1 = 1; | otherwise HS1 = 0 |
| If S12 is CLOSED, | HS2 = 1; | otherwise HS2 = 0 |
| If S9 is CLOSED, | HS3 = 1; | otherwise HS3 = 0 |

The four most significant bits of HPSTORE remain zero.

If HPBIT is 1 at STEP 600, the routine calling the A/D subroutine only needs the current value of HPSTORE. Therefore, READY lamp 65 is turned off (STEP 609), and a Return from Subroutine RTS is executed.

If neither the SAIDIT bit (STEP 595) nor HPBIT (STEP 600) is a 1, the routine calling the A/D subroutine wants it to monitor SMPNEW until the sensor signal reaches a maximum. As shown in FIG. 21B, to keep track of changes in SMPNEW on successive readings, the A/D subroutine uses two variables SMPOL1 (sample old 1) and SMPOL2 (sample old 2); initially these two variables are cleared to zero.

To avoid false detection of a maximum, a little hysteresis or delay is built into the test (STEP 602) for whether SMPNEW has begun to fall compared its value on prior readings (SMPOL1). Thus, at STEP 602 only if the quantity SMPNEW+5 is not equal to or greater than SMPOL1 will the subroutine jump to STEP 607, in effect ending the search for a maximum.

Before the sensor signal maximum is reached, at STEP 602 SMPNEW+5 will be equal to or greater than SMPOL1. Then at STEP 602, usually SMPOL1 will be equal to or greater than SMPOL2. If it is, the value of SMPOL1 is stored in SMPOL2 (STEP 604) and SMPOL1 itself updated to equal SMPNEW (STEP 605). The subroutine then loops back to STEP 587 to read the sensor for a fresh value of SMPNEW.

STEP 602 determines when the peak has been reached. Just past the peak of the sensor, SMPNEW+5 can be greater than SMPOL1 and at the same time SMPOL2 can be greater than SMPOL1. This will cause the flow to move from 602 to 603. In order to freeze SMPOL1 to the maximum value of the waveform, so that a maximum value is used for SMPOL1 the next time the comparison of STEP 602 is made, SMPOL1 is made equal to SMPOL2 at 606.

Eventually, at STEP 602 SMPNEW+5 will not exceed SMPOL1; i.e. SMPNEW will be at least 5 less than SMPOL1. This is taken as an indication that a maximum of the ventilation or compression has just been passed. The output variable MAXVAL is set equal to SMPOL1 (STEP 607). The READY lamp is turned off (STEP 609), and a Return from Subroutine RTS is executed (STEP 610).

If STEP 595 finds the SAIDIT bit set, the routine that called the A/D subroutine has already reported (said it) the maximum of a ventilation or compression to the student. The calling routine is only monitoring the sensor to determine when it falls back to the threshold value, indicating completion of the current ventilation or compression. Therefore, the calling routine only wants the instantaneous sensor value ADVAL of STEP 594. STEP 608 clears the SAIDIT bit to 0, and the subroutine jumps to ending STEPS 609, 610.

12. Hand Position Check Subroutine

Figure 22A:
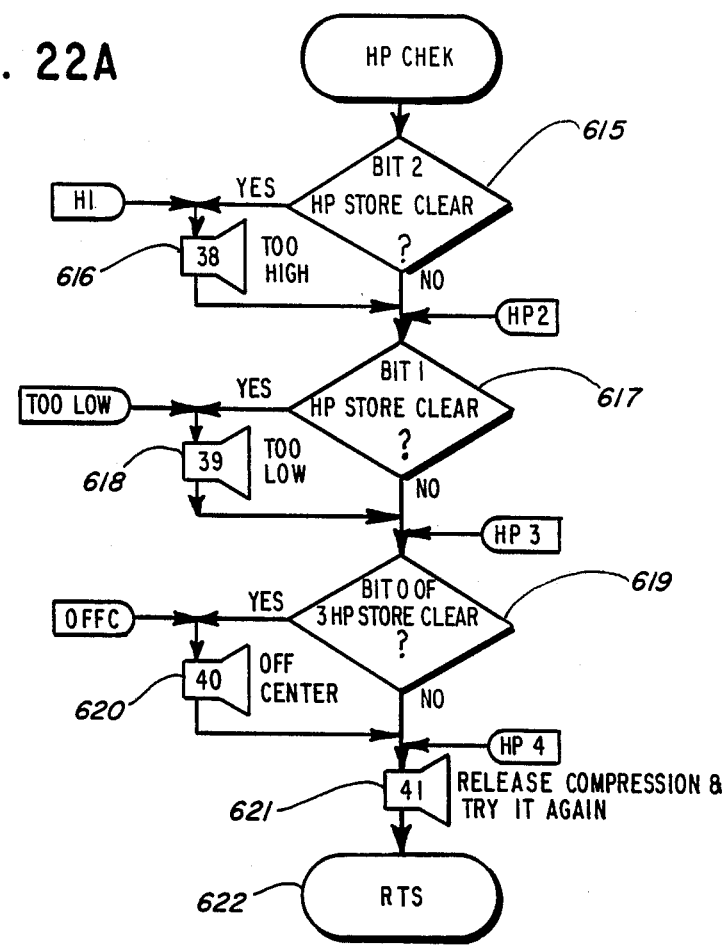
FIG. 22A is a flow chart for an embodiment of the Hand Position Check Subroutine incorporated in the Control Program of FIG. 11.
Figure 22B:
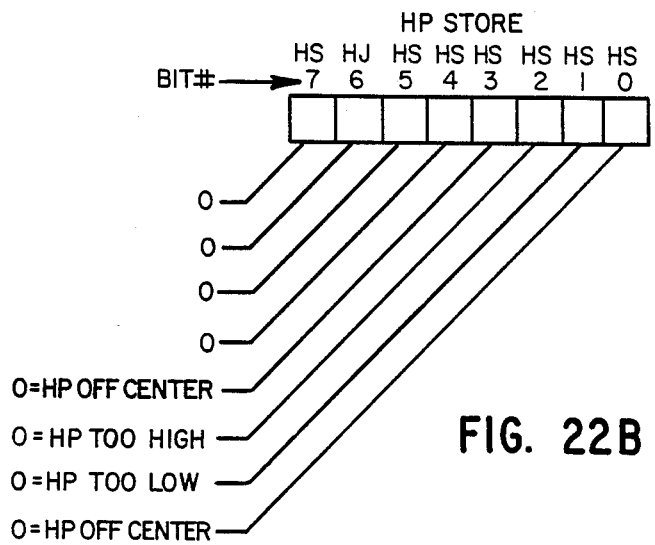
FIG. 22B is a map of the bits in a variable word HPSTORE used therein.

FIG. 22A shows a flow chart for an embodiment of the Hand Position Check Subroutine. This subroutine is called by the Hand Placement Routine, Single Chest Compression Routine, or the Chest Compression Rhythm Routine whenever they detect that the student's hand position is incorrect. FIG. 22B shows the bits of variable HPSTORE as set by the A/D Conversion subroutine from the hand position switches S3, S6, S9, S12. For a correct hand position HPSTORE is hex 0F. A "0" in any of the four least significant bits of HPSTORE indicates a corresponding open hand position switch because of incorrect hand position. If the calling routine determines that HPSTORE is not hex 0F, it promptly calls the Hand Position Check subroutine to voice a message telling the student what is wrong with his hand position.

If STEP 615 detects that bit 2 of HPSTORE is 0, STEP 616 voices Message 38: "Too high." Next, when STEP 617 detects that bit 1 of HPSTORE is 0, STEP 618 voices Message 39: "Too low." Finally, if STEP 619 detects that bit 0 or 3 of HPSTORE is 0, STEP 620 voices Message 40: "Off center." STEP 621 concludes the subroutine with Message 41: "Release compression! Try it again!" A Return A Return from Subroutine is then executed at STEP 622.

13. Scoring Subroutines a. SCORC1 Subroutine

Figure 23:
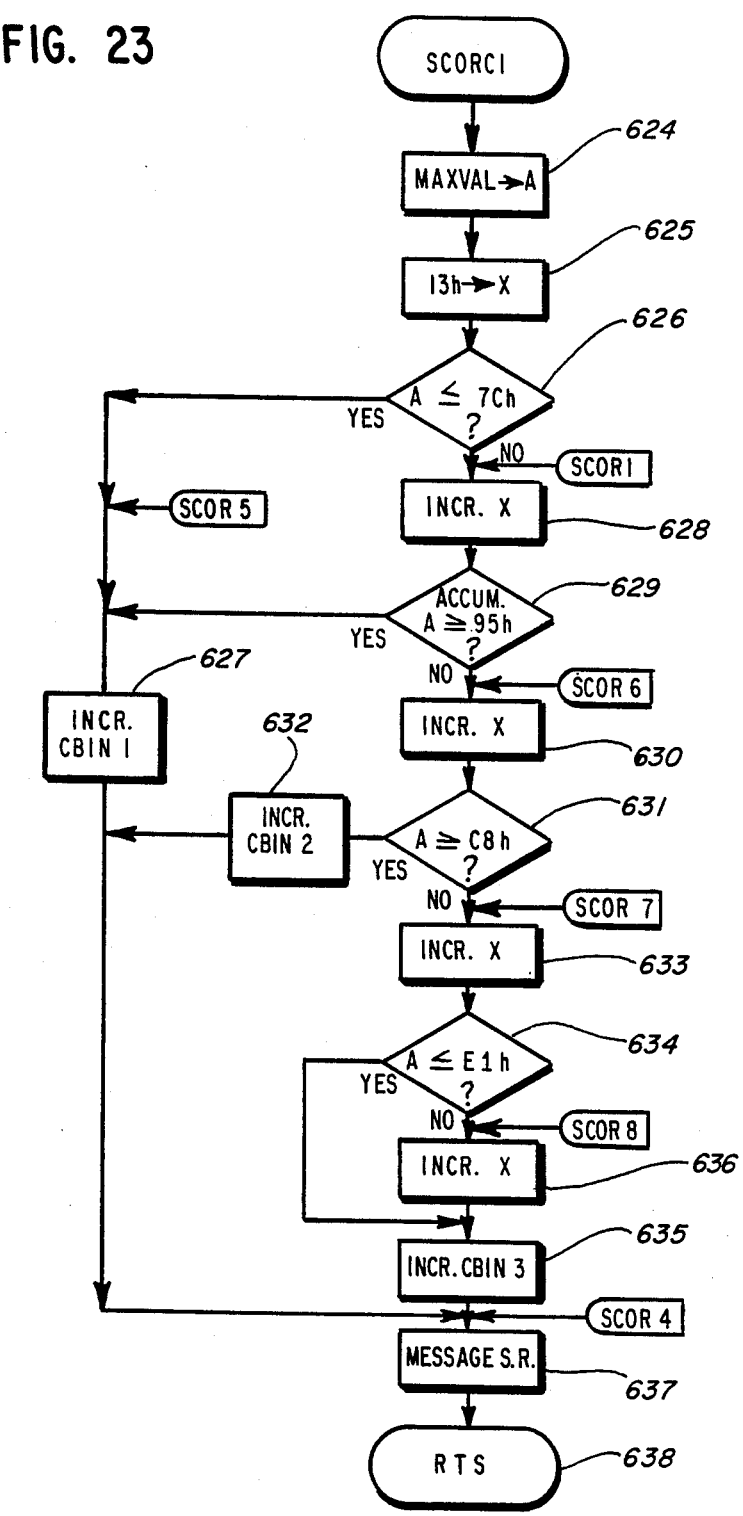
FIG. 23 is a flow chart for an embodiment of the scoring subroutine SCORC1 incorporated in the Control Program of FIG. 11.

FIG. 23 shows a flow chart of an embodiment of the SCORC1 subroutine. The Ventilation and Chest Compression Rhythm teaching routines call the SCORC1 subroutine to promptly voice a brief coaching comment on the maximum value of each ventilation or chest compression in a series as it occurs. This maximum is passed to the SCORC1 subroutine as the variable MAXVAL. To voice a coaching comment, the SCORC1 subroutine puts the appropriate Message number in register X of the microcomputer and calls the Message subroutine. SCORC1 also uses counter variables CBIN1, CBIN2, and CBIN3 to keep a running tally of how many ventilations or compressions were too shallow, acceptable, or too great.

An appropriate coaching comment is made promptly after a maximum of the ventilation or compression has been determined and stored in a variable MAXVAL by the A/D Conversion subroutine. The comment must be brief because of the short time between the maximums of successive ventilations or compressions. For example, the acceptable chest compression rhythm may be as fast as 100 compressions per minute, which leaves only 600 ms between successive compression maximums. Therefore, the preselected coaching words, see Table 3 above, can each be voiced in about one third of a second (333 ms).

Table 3 above shows the relationship between the input MAXVAL and the messages voiced and counter variables incremented by the SCORC1 subroutine. The subroutine begins by loading the value of MAXVAL in the microcomputer's accumulator register A (STEP 624), and loading the number hex 13 (decimal 19) in another register, the X register (STEP 625).

If STEP 626 determines that the value (MAXVAL) in register A is less than or equal to hex 7C, the student's effort is a very shallow one in Range B and counter variable CBIN1 is incremented (STEP 627). A jump is made to STEP 637, which calls the Message Subroutine to voice the message whose number is in register X, in this case Message 19: "MORE!"

If STEP 626 determines that register A is not less than or equal to hex 7C, register X is incremented to decimal 20 (STEP 628). If STEP 629 next determines that register A is less than or equal to hex 95, the effort is a shallow one in Range C and counter variable CBIN1 is incremented at STEP 627. Then STEP 637 calls the Message Subroutine to voice the message whose number is in register X, Message 20: "MORE".

If STEP 629 determines that register A is not less than or equal to hex 95, register X is again incremented, to decimal 21 (STEP 630). If register A is less than or equal to hex C8 (STEP 631), the effort is an acceptable one in Range D and counter variable CBIN2 is incremented (STEP 632). Then STEP 637 calls the Message Subroutine to voice the message whose number is in register X, Message 21: "GREAT".

If A is not less than or equal to hex C8 at STEP 631, register X is again incremented, to decimal 22 (STEP 633). Then if register A is less than or equal to hex E1 (STEP 634), the effort is a too deep one belonging in Range E and counter variable CBIN3 is incremented (STEP 635). Then STEP 637 calls the Message Subroutine to voice the message whose number is in register X, Message 22: "LESS".

If STEP 634 determines that A is not less than or equal to hex E1, register X is again incremented, to decimal 23 (STEP 636). The effort is very much too deep and belongs in Range F. Counter variable CBIN3 is incremented (STEP 635). Then STEP 637 calls the Message Subroutine to voice the message whose number is in register X, Message 23: "LESS!".

After the appropriate message is voiced at STEP 637, a Return from Subroutine is executed at STEP 638.

b. SCORC2 Subroutine

Figure 24:
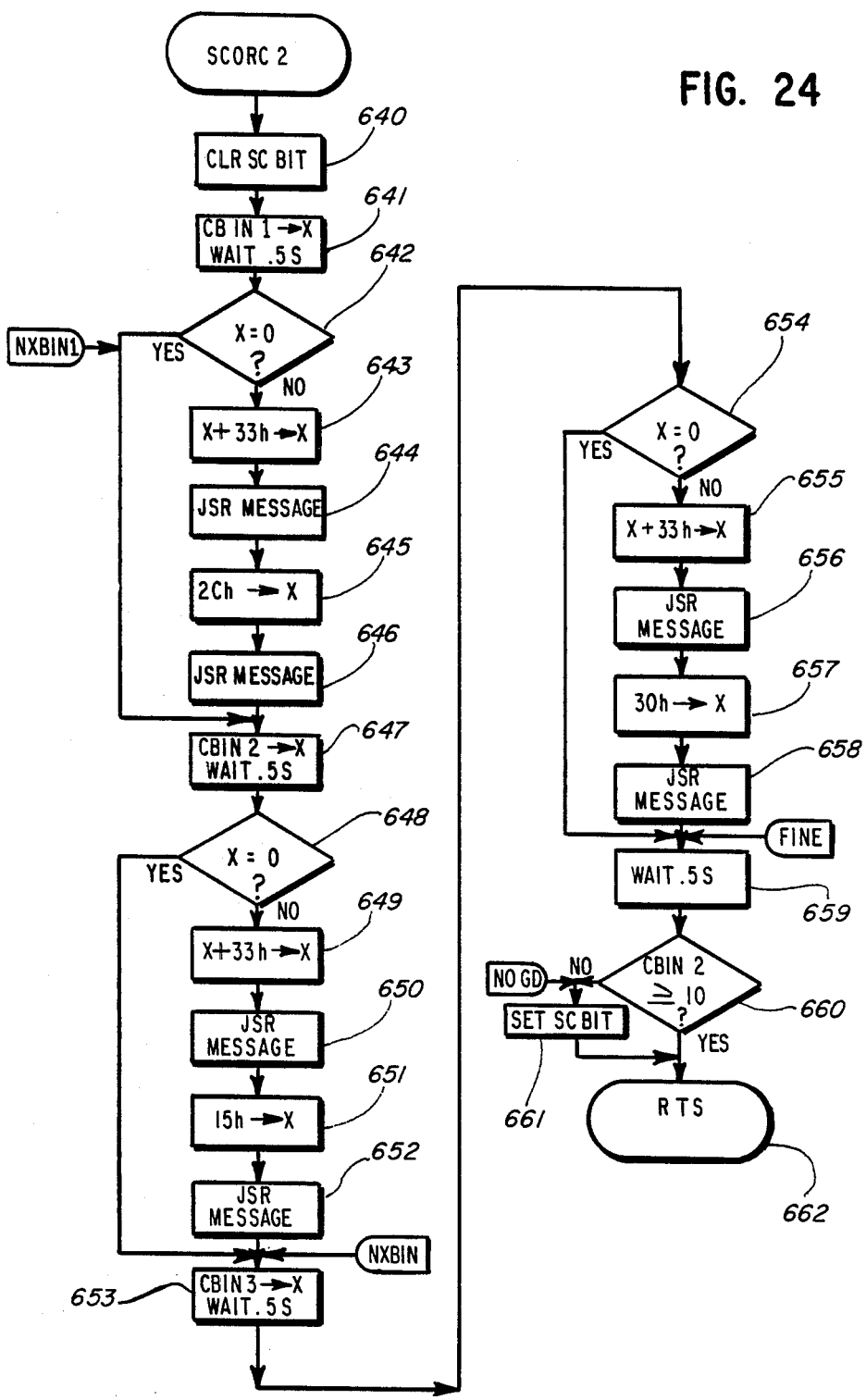
FIG. 24 is a flow chart for an embodiment of the scoring subroutine SCORC2 incorporated in the Control Program of FIG. 11.

FIG. 24 shows a flow chart of an embodiment of the scoring routine SCORC2 for use with the Chest Compression Rhythm (CCR) teaching routine of FIG. 17. After the CCR routine uses the SCORC1 subroutine to brief coaching comment on each chest compression as it occurs, it uses the SCORC2 subroutine to voice a summary and judgment of the student's performance of the whole series of 15 chest compressions.

When the subroutine is called, the number of shallow, acceptable, and too deep compressions are respectively stored in counter variables CBIN1, CBIN2, and CBIN3. If there have not been at least 10 acceptable compressions in the series of fifteen, the subroutine sets a bit called SCBIT. When control returns from the SCORC2 subroutine to the CCR routine, if the SCBIT is set the student will be told "Give fifteen chest compressions again" (see FIG. 17, STEPS 505–507).

The SCORC2 subroutine begins by clearing SCBIT (STEP 640) and reading the value of CBIN1, the number of too-shallow compressions, into register X. After a brief half-second wait, if STEP 642 finds that register X is 0, the subroutine skips to STEP 647. But if register X is not zero, a message for the number of shallow compressions must be voiced by the Message subroutine.

As described above, the Message subroutine is a general utility that voices the prestored message whose number is stored in register X. For example,

| REG. X | MESSAGE | REG. X | MESSAGE |
|---|---|---|---|
| 21. | Great | 58. | Seven were . . . |
| 44. | Too Shallow | 59. | Eight were . . . |
| 48. | Too deep. | 60. | Nine were |
|  | . . . | 61. | Ten were . . . |
| 52. | One was . . . | 62. | Eleven were . . . |
| 53. | Two were . . . | 63. | Twelve were . . . |
| 54. | Three were . . . | 64. | Thirteen were . . . |
| 55. | Four were . . . | 65. | Fourteen were . . . |
| 56. | Five were . . . | 66. | Fifteen were . . . |
| 57. | Six were . . . |  |  |

Suppose register X contains (from CBIN1) the number of too-shallow compressions (a number 1–15). By increasing register X by decimal 51 (hex 33), the Message routine can voice the corresponding message (messages 52–66). For example, suppose X equals 6, the number of shallow compressions. Increasing X by 51 makes register X=57. If the Message subroutine is called with register X=57, numerical Message 57 will be voiced: "Six were . . . "

Therefore, at STEP 643 register X is increased by hex 33 (decimal 51), and then the Message subroutine is called to voice the message whose number is stored in register X. To complete the summary message, at STEP 645 register X is loaded with hex 2C (decimal 44), and the Message subroutine is called again to voice Message 44: "too shallow."

Next, STEP 647 reads the value of CBIN2, the number of acceptable compressions, into register X, and pauses for half a second. If STEP 648 finds that register X is 0, the subroutine skips to STEP 653. But if register X is not zero, STEP 649 prepares for voicing the appropriate message by increasing register X by hex 33 (decimal 51), and then the Message subroutine is called (STEP 650). The summary message is completed by loading a hex 15 (decimal 21) into X and again calling the Message subroutine to voice Message 21: "great".

Next, STEP 653 reads the value of CBIN3, the number of too-deep compressions, into register X and pauses for half a second. If STEP 654 finds that register X is 0, the subroutine skips to STEP 659. But if register X is not zero, STEP 655 prepares for voicing the appropriate message by increasing register X by hex 33 (decimal 51), and then the Message subroutine is called (STEP 656). The summary message is completed by loading a hex 30 (decimal 48) into X and again calling the Message subroutine to voice Message 48: "Too deep."

After another half-second pause (STEP 659), STEP 660 determines if CBIN2 indicates that there have been at least 10 acceptable compressions in the series of fifteen. If there have, a Return from Subroutine (RTS) is executed (STEP 662). If not, the SCBIT is set to 1 (STEP 661) before executing the RTS.

c. SCORC3 Subroutine

Figure 25:
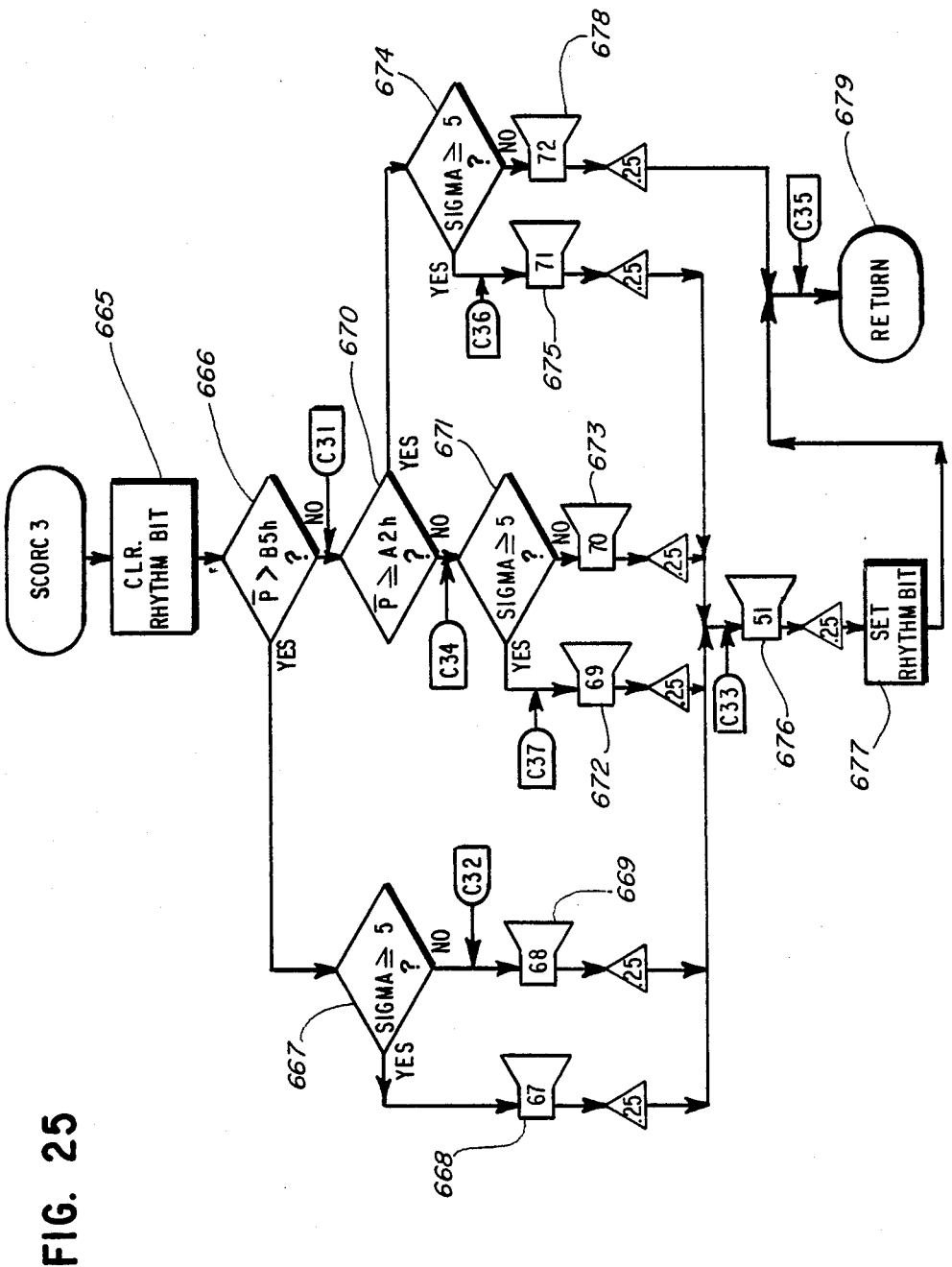
FIG. 25 is a flow chart for an embodiment of the scoring subroutine SCORC3 incorporated in the Control Program of FIG. 11.

FIG. 25 shows a flow chart of an embodiment of the scoring routine SCORC3 for use with the Chest Compression Rhythm (CCR) teaching routine of FIG. 17. When the series of fifteen chest compressions is completed, the CCR routine uses the SCORC3 subroutine to voice a judgment of the speed and regularity of the student's rhythm in performing the compressions.

When the subroutine is called, the average period $\bar{P}$ and the estimate SIGMA in terms of Timer Data Register TDR readings respectively determined at STEPS 500 and 501 of the CCR routine are available in RAM.

If the student's chest compression rhythm is the wrong speed or irregular, the subroutine sets a bit called RHYTHM. When control returns from the SCORC3 subroutine to the CCR routine, if the RHYTHM bit is set the student will be told "Give fifteen chest compressions again." (see FIG. 17, STEPS 508, 509, 507).

Table 6 above shows how the average period of the student's compressions can be interpreted from the average of the Timer Data Register TDR readings. After the RHYTHM bit is cleared (STEP 665), STEP 666 determines if $\bar{P}$ is greater than hex B5, which is equivalent to asking if the average compression period is less than 600 ms. If it is, the student's rhythm is too fast. STEP 667 then determines if SIGMA is equal to or greater than 5.

Since the TDR readings relate to timer clock pulses spaced 8 ms apart, this corresponds to an estimate of irregularity equal to or greater than 40 ms. If SIGMA is that large, STEP 668 voices Message 67, "Rhythm is too fast and irregular," and proceeds to STEP 676. If SIGMA is not equal to or greater than 5, STEP 669 just voices Message 68, "Rhythm is too fast," and proceeds to STEP 676.

If STEP 666 determines that $\bar{P}$ is not greater than hex B5, the rhythm is not too fast. STEP 670 then determines if $\bar{P}$ is greater than or equal to hex A2, which is equivalent to asking if the average compression period is less than or equal to 752 ms. If it isn't, the rhythm is too slow. STEP 671 then determines if SIGMA is equal to or greater than 5 (equivalent to 40). If SIGMA is that large, STEP 672 voices Message 69, "Rhythm is too slow and irregular," and proceeds to STEP 676. If SIGMA is not equal to or greater than 5, STEP 673 just voices Message 70, "Rhythm is too slow," and proceeds to STEP 676.

If STEP 670 determines that $\bar{P}$ is greater than or equal to hex A2, the compression period is in the acceptable range 600–752 ms. STEP 674 then determines if SIGMA is equal to or greater than 5 (equivalent to 40). If SIGMA is that large, STEP 675 voices Message 71: "Rhythm is irregular," and proceeds to STEP 676.

If at STEP 674 SIGMA is not equal to or greater than 5, both speed and regularity are acceptable. STEP 673 voices Message 72, "Excellent rhythm," and a Return from Subroutine is executed (STEP 679).

If the rhythm has the wrong speed or is irregular, the student needs help in establishing his beat. STEP 676 voices Message 51: "Set the cadence switch for a cadence." The RHYTHM bit is set to 1 (STEP 677) before executing the Return from Subroutine (STEP 679).

The many advantages of this inexpensive manikin system are now apparent. The components are easily made and assembled, and operate under flexible programmable control; the purchased electronic parts are readily available commercial components. The synthesized voice coaching makes excellent use of the sensor data to realistically simulate the timing, judgment, and encouraging advice of human coaching. It can be easily operated by the student with little or no preparation. Finally, there is no heavy, bulky, or complicated apparatus that must be transported, interconnected or managed by the user.

While the principles of the invention have been described above in connection with specific apparatus and applications, it is to be understood that this description is only an example and is not intended as a limitation on the scope of the invention.

APPENDIX I

Messages by Message Number

1. Welcome to Coach Andy (TM).
2. Ventilation. Open the airway by gently tilting the head way back.
3. Press down on the manikin's forehead with the palm of one hand.
4. With your other hand, lift either under the neck, near the base of the head, or with the fingertips, under the bony part of the jaw near the chin.
5. (none)
6. Pinch off the manikin's nostrils.
7. Open your mouth wide, take a deep breath, and make a tight seal with the manikin's mouth and blow. Try a single ventilation.
8. I will tell you how you did.
9. More air.
10. Be sure that you're taking a deep breath and keeping a tight seal with the manikin's nostrils.
11. Blow harder.
12. Try it again.
13. Please ask the instructor for help.
14. Close, but blow harder.
15. Excellent
16. Perfect. Now try giving two slow breaths.
17. Good, but blow less forcefully.
18. Blow into the manikin's mouth with complete refilling of your lungs after each breath.
19. More!
20. More.
21. Great.
22. Less.
23. Less!
24. Try giving two breaths again.
25. Excellent ventilation. If you feel confident, practice checking the carotid pulse. If you don't, try giving two breaths again.
26. Carotid pulse. The carotid pulse is located on either side of the Adam's Apple.
27. Gently, try to sense it with the index and middle fingers of one hand.
28. Maintain the head tilt with the palm of your other hand.
29. If you have difficulty checking it, please ask the instructor for help.
30. Hand position. Feel for the border of the manikin's ribs with the index and middle fingers of the hand closest to the manikin's waist.
31. Move them upward along the ribcage until you reach the ribcage notch.
32. Place the heel of your other hand just above the two fingers. Then place the first hand on top of it.
33. Keep your fingers off the manikin's ribs.
34. Push down. I will check your hand position.
35. Fine, remove and reset your hands. Try it again.
36. Good, if you feel confident, you should now practice a single chest compression. If you don't, try it again.
37. Your hand position is not quite right.
38. Too high.
39. Too low.
40. Off center.
41. Release compression! Try it again!
42. Single chest compression. Take the correct hand position, your elbows locked and your shoulders directly over the sternum.

43. The chest should be compressed smoothly one and one half to two inches. Try a single chest compression.
44. Too shallow.
45. Too shallow! Be sure that you're pressing straight down, your elbows locked and your shoulders directly over the sternum.
46. Close, but too shallow.
47. Close but too deep.
48. Too deep.
49. Great. Now practice chest compression rhythm or try it again.
50. Chest compression rhythm. Give fifteen chest compressions smoothly, no bouncing, using a one and two and three and four ... to fifteen cadence. Come all the way up between compressions.
51. Set the cadence switch for a cadence.
52. One was ...
53. Two were ...
54. Three were ...
55. Four were ...
56. Five were ...
57. Six were ...
58. Seven were ...
59. Eight were ...
60. Nine were ...
61. Ten were ...
62. Eleven were ...
63. Twelve were ...
64. Thirteen were ...
65. Fourteen were ...
66. Fifteen were ...
67. Rhythm is too fast and irregular.
68. Rhythm is too fast.
69. Rhythm is too slow and irregular.
70. Rhythm is too slow.
71. Rhythm is irregular.
72. Excellent rhythm.
73. Come all the way up between compressions.
74. Give fifteen chest compressions again.
75. Not quite right.
76. If you feel confident, practice clearing the airway. If you don't, give fifteen chest compressions again.
77. Replace battery.
78. Now practice the correct hand position.
79. Clearing the airway. Kneel astride the manikin's thighs.
80. Place the heel of one hand slightly above the navel. Place the other hand on top of it.
81. Press into the abdomen with quick upward thrusts. Each thrust should be distinct and delivered with the intent of clearing the airway. Do it ten times.
82. When you feel confident, practice ventilating the manikin.

APPENDIX A

```
AVOCET SYSTEMS 6805 CROSS-ASSEMBLER -   VERSION 1.08M

SOURCE FILE NAME: ANDY.ASM      © 1987 MICHAEL INGENITO

00000                   NAME    ANDY
                ;
                ;
                ;       THIS CODE IS WRITTEN FOR THE HD637B05VOP (HITACHI) CMOS
                ;       MICROCOMPUTER
                ;
                ;       modified 9/8/86
                ;
                ;       COACH ANDY
0000            PORTA   EQU     $00
0001            PORTB   EQU     $01
0002            PORTC   EQU     $02
0003            PORTD   EQU     $03
0004            ADDR    EQU     $04
0005            BDDR    EQU     $05
0006            CDDR    EQU     $06
0007            DDDR    EQU     $07
0008            TDR     EQU     $08
0009            TCR     EQU     $09
000A            MR      EQU     $0A
0010            SCICR   EQU     $10
0011            SCISR   EQU     $11
0012            SCIDR   EQU     $12
                ;
                ;       RAM
                ;
0040                    ORG     $040
0040            RAMBIT  DS      1
0041            RUNBIT  DS      1
0042            ALLBIT  DS      1
0043            LASTMS  DS      1
0050                    ORG     $050
0050            WDAR    DS      1
0051            SUH     DS      1
```

```
0052            SLH     DS      1
0053            BUH     DS      1
0054            BLH     DS      1
0055            SAM     DS      1
0056            NUMWRD  DS      1
0057            WRDOFF  DS      1
0058            SSAW    DS      1
0059            SILREG  DS      1
005A            FXWRD   DS      1
005B            EPRES   DS      1
005C            WRDTAB  DS      1
005D            WAITC   DS      1
005E            FOURC   DS      1
0060                    ORG     $60
0060            LAMP    DS      1
0061            FORMIN  DS      1
0062            SWOLD   DS      1
0063            HPSTOR  DS      1
0064            FIRST   DS      1
0065            TH1     DS      1
0066            MAXVAL  DS      1
0067            SMPNEW  DS      1
0068            BADC1   DS      1
0069            BADC    DS      1
006A            GOODC   DS      1
006B            ABLE    DS      1
006C            BAKER   DS      1
006D            CHUCK   DS      1
006E            DOG     DS      1
006F            MAXC    DS      1
0070            CBIN1   DS      1
0071            CBIN2   DS      1
0072            CBIN3   DS      1
0073            PERCTR  DS      1
0074            MINTOT  DS      1
0075            SMPOLD  DS      1
0076            SMPOL1  DS      1
0077            SMPOL2  DS      1
0078            XBAR    DS      1
0079            SIGMA   DS      1
007A            PERIOD  DS      $F
0089            CYCLE   DS      1
008A            SENSIT  DS      1
008B            ADVAL   DS      1
008C            MINCTR  DS      1
008D            SAMPLE  DS      1
008E            CANSTR  DS      1
008F            LICAND  DS      1
0090            PLIER   DS      1
0091            ANSMSB  DS      1
0092            ANSLSB  DS      1
0093            TEMP1   DS      1
0094            TOTLSB  DS      1
0095            TOTMSB  DS      1
0096            NEWNUM  DS      1
0097            SORMSB  DS      1
0098            SORLSB  DS      1
0099            DNDMSB  DS      1
009A            DNDLSB  DS      1
009B            TEMP2   DS      1
009C            QUOTNT  DS      1
                ;
                ;
                ;
                ;       INITIALIZATION
                ;
1000                    ORG     $1000   ;START OF ROM($1000 FOR 6305)XXXXXXXXXXXX
                XXXX
1000 A64F       INIT    LDA     #$4F    ;NO TIMING INT. DIV. BY 2-15
1002 B709               STA     TCR
1004 3F00               CLR     PORTA   ;NO FALSE PWR DN
1006 A660               LDA     #$60
```

```
1008 B70A              STA    MR      ;D6 AS PORT & LEVEL,EDGE TRIG.
100A A6FF              LDA    #$FF
100C B704              STA    ADDR    ;SET I/O
100E B706              STA    CDDR
1010 A6FE              LDA    #$FE
1012 B705              STA    BDDR
1014 3F07              CLR    DDDR
1016
                ;
                ;      CLEAR RAM
                ;
1016 3F40              CLR    RAMBIT
1018 3F41              CLR    RUNBIT
101A 3F42              CLR    ALLBIT
101C AD18              BSR    CLRAM0
101E 1800              BSET   4,PORTA
1020 1900              BCLR   4,PORTA   ;RESET SPCH SYN.
                ;
                ;      CLEAR OUTPUTS
                ;
1022 A698              LDA    #$98
1024 B701              STA    PORTB   ;B SIDE OF MUX IS EN.
1026 A650              LDA    #$50
1028 B700              STA    PORTA   ;CLR LATCH
102A A601              LDA    #$1
102C CD110A            JSR    WAIT    ;WAIT 16 MS.
102F 2F01              BIH    ST
1031 8E                STOP
1032 A660       ST     LDA    #$60
1034 B700              STA    PORTA   ;POWER DOWN
                ;
                ;      CLEAR RAM S.R.
                ;
1036 AE60       CLRAM0 LDX    #$60
1038 7F         CLEAR  CLR    0,X
1039 5C                INCX
103A A3FA              CPX    #$FA
103C 26FA              BNE    CLEAR
103E 81                RTS
                ;
                ;      END OF CLEAR RAM S.R.
                ;
                ;
                ;      INTERRUPT SEQUENCE
                ;
103F 1800       INT    BSET   4,PORTA ;RESET SPCH SYN.
1041 1900              BCLR   4,PORTA ;STOP SOUND
1043 A601              LDA    #$1     ;WAIT 16MS FOR DBNCE
1045 CD110A            JSR    WAIT    ;OF SW. DN.
1048 1D01              BCLR   6,PORTB ;ENABLE 'B'SIDE OF MUX
104A B603              LDA    PORTD
104C A40F              AND    #$F
104E B762              STA    SWOLD   ;ONLY NEED D3,D2,D1,D0
1050 2E01              BIL    RUN1
1052 80                RTI
1053 2EFE       RUN1   BIL    RUN1
1055 A620              LDA    #$20    ;WAIT 512MS-DO NOT
1057 CD110A            JSR    WAIT    ;WISH INSTANTANEOUS RESPONSE.
105A 0E410E            BRSET  7,RUNBIT,RUN3
105D 1E41              BSET   7,RUNBIT
105F AE01              LDX    #$01
1061 CD1122            JSR    MESAGE  ;MESS. #1 "WELCOME" ON POWER UP
1064 A654              LDA    #$54
1066 CD1744            JSR    LAMPS   ;ENABLE LAMPS TO BLINK
1069 2000              BRA    RUN3
106B 4F         RUN3   CLRA
106C B162              CMP    SWOLD
106E 2604              BNE    RUN4A               ;IGNORE PAUSE IF IN REPEAT
1070 094061            BRCLR  4,RAMBIT,RUN4
1073 80                RTI
1074 4C         RUN4A  INCA
```

```
1075 B162            CMP     SWOLD
1077 2623            BNE     NUBGIN
1079 094001          BRCLR   4,RAMBIT,RUN6

107C 80              RTI                     ;IGNORE 2ND REPEAT
107D A656     RUN6   LDA     #$56
107F CD1744          JSR     LAMPS           ;TURN ON REPEAT LAMP
1082 1840            BSET    4,RAMBIT        ;PLAOLD BIT
1084 9A              CLI
1085 BE43            LDX     LASTMS
1087 CD1122          JSR     MESAGE          ;REPEAT LAST MESSAGE
108A 1A40            BSET    5,RAMBIT        ;RETURN FROM MESS.BIT
108C 1940            BCLR    4,RAMBIT        ;PLAOLD BIT
108E A601            LDA     #$1
1090 B75D            STA     WAITC           ;FOR QUICK RET. TO PROGRAM
1092 3F59            CLR     SILREG          ;DITTO
1094 1142            BCLR    0,ALLBIT        ;DITTO
1096 A650            LDA     #$50            ;TURN OFF REPEAT LAMP
1098 CD1744          JSR     LAMPS
109B 80              RTI
109C 9C       NUBGIN RSP                     ;NO GOING BACK
109D 3F40            CLR     RAMBIT          ;CLR FLAGS
109F 3F42            CLR     ALLBIT          ;DITTO
10A1 1B01            BCLR    5,PORTB         ;STOP C.P. TRANSDUCER
10A3 A650            LDA     #$50
10A5 CD1744          JSR     LAMPS           ;STOP BLINK & TURN OFF
                                              WAIT AND REPEAT LAMPS
10A8 A602            LDA     #$02
10AA B162            CMP     SWOLD
10AC 2603            BNE     NOTHT
10AE CC1668          JMP     HT
10B1 4C       NOTHT  INCA
10B2 B162            CMP     SWOLD
10B4 2603            BNE     NOTCCR
10B6 CC150A          JMP     CCR
10B9 4C       NOTCCR INCA
10BA B162            CMP     SWOLD
10BC 2603            BNE     NOTSCC
10BE CC143D          JMP     SCC
10C1 4C       NOTSCC INCA

10C2 B162            CMP     SWOLD
10C4 2603            BNE     NOTHP
10C6 CC13C3          JMP     HP
10C9 4C       NOTHP  INCA
10CA B162            CMP     SWOLD
10CC 2603            BNE     NOTCP
10CE CC1390          JMP     CP
10D1 CC12A0   NOTCP  JMP     VENT

10D4 074005   RUN4   BRCLR   3,RAMBIT,RUN7   ;HC BIT
10D7 1740            BCLR    3,RAMBIT        ;DITTO
10D9 1240            BSET    1,RAMBIT        ;RTIBIT
10DB 80              RTI
10DC 1640     RUN7   BSET    3,RAMBIT

;     FOUR ROUTINE
;
; THIS ROUTINE IS USED WHEN THE PAUSE/RESUME
; BUTTON IS PUSHED. IF NO SEQUENCE BUTTON IS PUSHED
; WITHIN FOUR MINUTES THE MACHINE TURNS OFF.
;
10DE 9A       FOUR   CLI
10DF A6FF            LDA     #$FF
10E1 B761            STA     FORMIN
10E3 A607     SOMEMO LDA     #$7             ;NO OF P/R LAMP
10E5 AD1C            BSR     ON              ;PART OF LAMP S.R.
10E7 A620            LDA     #$20
10E9 AD1F            BSR     WAIT            ;FOR .5 SEC
10EB B660            LDA     LAMP            ;LAMP HAS # OF PROGRAM
10ED                                         ;LAMP THAT WAS ON
```

```
10ED AD12              BSR     LAMPON      ;TURN ON PROGRAM LAMP
10EF A620              LDA     #$20        ;FOR .5 SEC.
10F1 AD17              BSR     WAIT
10F3 034003            BRCLR   1,RAMBIT,TENMO ;RTI BIT, IF SET
10F6 1340              BCLR    1,RAMBIT
10F8 80                RTI                 ;RET. TO PROGRAM
10F9 3A61      TENMO   DEC     FORMIN
10FB 26E6              BNE     SOMEMO
10FD 1A00      PWROFF  BSET    5,PORTA     ;PWR. DN
10FF 1C00              BSET    6,PORTA
               ;
               ;       END OF INTERRUPT ROUTINE
               ;
               ;       LAMPON S.R. - TO TURN ON A PROGRAM LAMP
               ;       ENTER WITH A HOLDING LAMP #
               ;
               ;
1101 B760      LAMPON  STA     LAMP        ;NEED THIS FOR P/R FUNCTION
1103 B700      ON      STA     PORTA       ;A2-A0 ARE 4514 INPUTS
1105 1A00              BSET    5,PORTA     ;LAMPSTROBE
1107 1B00              BCLR    5,PORTA
1109 81                RTS
               ;
               ;
               ;       WAIT 16 MS SUB-ROUTINE
               ;       ENTER WITH A HOLDING THE NO. OF 16
               ;       MILLISECOND SILENCES.
               ;
110A B75D      WAIT    STA     WAITC       ;COUNTER
110C A64F              LDA     #$4F
110E B709              STA     TCR         ;SET UP TIMER
1110 A6FF      WAITMO  LDA     #$FF        ;AVOIDS DECREMENTING
1112 B15D              CMP     WAITC       ;THRU ZERO THAT
1114 270B              BEQ     GOBAK       ;CAN OCCUR
1116 B708              STA     TDR         ;SET UP TIMER
1118 1F09              BCLR    7,TCR
111A 0F09FD    ZZWAIT  BRCLR   7,TCR,ZZWAIT ;WAIT HERE
111D                                        ;UNTIL TIMER UP
111D 3A5D      ONWAIT  DEC     WAITC
111F 26EF              BNE     WAITMO
1121 81        GOBAK   RTS
               ;
               ;       MESAGE SUB-ROUTINE
               ;
               ;  VOCALIZES THE MESSAGE (# IS IN X ON ENTRY)
               ;
               ;
1122 A6FF      MESAGE  LDA     #$FF
1124 B706              STA     CDDR        ;PORTC MUST BE OUTPUT PORT
1126 1C40              BSET    6,RAMBIT    ;MESAGE BIT
1128 094011            BRCLR   4,RAMBIT,PLAOLD ;PLAOLD BIT
112B 5A        MESSA   DECX                ;MESS. NOS. START FROM 0
112C 58                LSLX                ;MULTI. X BY 2 AS 2I TAB
                                           ;BYTES/MESS.
112D D61812            LDA     I,X         ;PICK UP FIRST I BYTE
1130 44                LSRA                ;FIRST OF MESS. TAB. BITS
1131 240D              BCC     NOTM
1133 44                LSRA                ;ITS M DISCARD NEXT BIT
1134 1641              BSET    3,RUNBIT    ;M TABLE FLAG
1136 1541              BCLR    2,RUNBIT    ;L TABLE FLAG
1138 1941              BCLR    4,RUNBIT    ;N TABLE FLAG
113A 2015              BRA     MESSC
113C BF43      PLAOLD  STX     LASTMS
113E 20EB              BRA     MESSA
1140 44        NOTM    LSRA                ;SECOND MESS. TAB. BIT
1141 2408              BCC     LTAB        ;L TABLE WORD
1143 1841              BSET    4,RUNBIT    ;N TABLE FLAG
1145 1541              BCLR    2,RUNBIT    ;L TABLE FLAG
1147 1741              BCLR    3,RUNBIT    ;M TABLE FLAG
1149 2006              BRA     MESSC
114B 1441      LTAB    BSET    2,RUNBIT    ;M TAB
114D 1741              BCLR    3,RUNBIT    ;N TAB
```

```
114F 1941             BCLR    4,RUNBIT        ;P TAB
                ;
                ;
                ;
1151 B756    MESSC STA       NUMWRD   ;REST OF BITS = NO. OF WRDS IN MESS.
                ;
1153 5C              INCX
1154 D61812          LDA     I,X      ;PICK UP NEXT I BYTE
1157 B757            STA     WRDOFF   ;OFFSET FROM TOP OF MESS.
1159                                  ;TABLE TO FIRST WRD
1159 BE57    NEXWRD LDX      WRDOFF
115B 04410D          BRSET   2,RUNBIT,LTABLE
115E 064105          BRSET   3,RUNBIT,MTABLE
1161 D61AA5          LDA     N,X      ;N TABLE MESSAGE
1164 2008            BRA     HEAH
1166 D619B3  MTABLE LDA      M,X      ;M TABLE MESSAGE
1169 2003            BRA     HEAH
116B D618B6  LTABLE LDA      L,X      ;L TABLE MESSAGE
116E A1F8    HEAH   CMP      #$F8     ;WRD # - F8
1170 2430           BCC      SILBYT   ;BRANCH TO SILBYT IF WRD # IS
1172                                  ;EQUAL OR GREATER THAN $F8
1172 034229         BRCLR    1,ALLBIT,REGLAR ;SPECIAL SILENCE AFTER
1175                                  ;WRD. FLAG
                ;
1175 1342           BCLR     1,ALLBIT
1177 AD17    SPK    BSR      LD2LSB   ;S.R. TO LOAD 2LSB'S
1179                                  ;TO WRD TAB
1179 A4FC           AND      #$FC     ;WORD NO. IS NOW
117B B75A           STA      FXWRD    ;MULT BY 4
117D A604           LDA      #$04
117F B75E           STA      FOURC    ;4 BYTES/WORD
1181 A651           LDA      #$051    ;RAM ADD THAT HOLDS
                ;                     1ST BYTE OF WRD DATA
1183 B750           STA      WDAR     ;WORD DATA ADD REG.
1185 BE5A           LDX      FXWRD    ;OFFSET TO GET WRD.
                ;
1187 B65C    MODATA LDA      WRDTAB
1189 264A           BNE      NOTSSS
118B D61B92         LDA      S,X
118E 205E           BRA      READY
                ;
                ; LD 2LSB SUB-ROUTINE
                ; ENTER WITH A HOLDING A MESSAGE TABLE BYTE
                ; KNOWN TO BE A SPOKEN WORD.
                ;
1190 97      LD2LSB TAX               ;NOW A&X HOLD BYTE
1191 A403           AND      #$03     ;ONLY 2LSB'S LEFT IN A
1193 B75C           STA      WRDTAB
1195 9F             TXA               ;MESS. TAB BYTE TO A
1196 81             RTS
                ;
                ; LD SREG SUB-ROUTINE - THIS IS THE SAME
                ; AS ABOVE BUT 2LSB'S ARE STORED IN SIL REG
                ;
                ;
1197 97      LDSREG TAX
1198 A403           AND      #$3
119A B759           STA      SILREG
119C 9F             TXA
119D 81             RTS
                ;
                ;
119E ADF7    REGLAR BSR      LDSREG   ;2 LSBS TO SILREG
11A0 20D5           BRA      SPK
                ; AT THIS POINT THE MESSAGE TABLE BYTE
                ; IN A IS KNOWN TO BE A SILENCE WORD
                ; F8 = OMS, F9 = 32MS, FA = 64MS
                ; FB = 128 MS FC = 384MS, FD = 2 SEC,
                ; FE = 4 SEC, FF = 6 SEC.
                ;
11A2 1242    SILBYT BSET     1,ALLBIT          ;SPEC SIL. AFTER WRD FLAG.
```

```
11A4 A1FD            CMP     #$FD              ;A - FD
11A6 2417            BCC     LONG              ;SECONDS OF SILENCE
11A8 A0F8            SUB     #$F8              ;0 TO 4 LEFT
11AA A103            CMP     #$3
11AC 2405            BCC     SILO              ;= 4 OR 3
11AE B759    SILA    STA     SILREG
11B0 CC1288          JMP     HOP
11B3 A103    SILO    CMP     #$3
11B5 2705            BEQ     SILB              ; = 3
11B7 48              LSLA                      ; = 4, MULT BY 2 AND ADD 4
11B8 AB04            ADD     #$4
11BA 20F2            BRA     SILA              ; = TO GET 8 X 16 MS
11BC 4C      SILB    INCA
11BD 20EF            BRA     SILA
11BF A0FC    LONG    SUB     #$FC              ; = 1, 2, 3
11C1 A101            CMP     #$1
11C3 2708            BEQ     SILC
11C5 A102            CMP     #$2
11C7 2608            BNE     SILD
11C9 A678    SILE    LDA     #$78              ;4 SEC. OF SIL.
11CB 20E1            BRA     SILA
11CD A63C    SILC    LDA     #$3C              ;2 SEC. OF SIL.
11CF 20DD            BRA     SILA
11D1 1042    SILD    BSET    0,ALLBIT
11D3 20F4            BRA     SILE
11D5 A601    NOTSSS  LDA     #$01
11D7 B15C            CMP     WRDTAB            ;01 - WRDTAB
11D9 2605            BNE     NOTTEE
11DB D61C6E          LDA     T,X
11DE 200E            BRA     READY
11E0 A602    NOTTEE  LDA     #$02
11E2 B15C            CMP     WRDTAB
11E4 2605            BNE     VWRD
11E6 D61D56          LDA     U,X
11E9 2003            BRA     READY
11EB D61E32  VWRD    LDA     V,X
11EE BE50    READY   LDX     WDAR              ;$051 1ST TIME
11F0 F7              STA     0,X               ;SUH ADD - 051 1ST TIME
11F1 3C5A            INC     FXWRD
11F3 BE5A            LDX     FXWRD             ;FOR NEXT ADD BYTE
11F5 3C50            INC     WDAR
11F7 3A5E            DEC     FOURC             ;4 ADD BYTES YET?
11F9 268C            BNE     MODATA            ;NO
11FB B653            LDA     BUH               ;YES
11FD A40F            AND     #$0F              ;GET EPROM WRD IS IN
11FF B75B            STA     EPRES
1201 B653            LDA     BUH               ;ONLY NEED 4 MSB
1203 44              LSRA
1204 44              LSRA
1205 44              LSRA
1206 44              LSRA
1207 B753            STA     BUH
1209 0A4051  ZZSPK   BRSET   5,RAMBIT,ALLOVR   ;RETURN BIT
120C 1F01            BCLR    7,PORTB           ;START READ OF A/D
120E 0C03FD  ZZSPK1  BRSET   6,PORTD,ZZSPK1    ;LV WHEN PORT C IS AVAIL
1211 4F              CLRA
1212 B706            STA     CDDR              ;CHANGE C TO INPUT PORT
1214 1600            BSET    3,PORTA           ;LATCH A/D
1216 1700            BCLR    3,PORTA
1218 1F01            BCLR    7,PORTB           ;READ IS DONE
121A 1401            BSET    2,PORTB           ;EN OUTPUTS OF INPUT PORT
121C B602            LDA     PORTC
121E B78D            STA     SAMPLE
1220 1501            BCLR    2,PORTB           ;3 STATE I/O PORT OUTPUTS
1222 A6FF            LDA     #$FF
1224 B706            STA     CDDR              ;PORTC BACT TO SPCH SYN
1226 B65B            LDA     EPRES
1228 B700            STA     PORTA
122A B652            LDA     SLH
122C B702            STA     PORTC             ;EPROM SELECTED
122E 1600            BSET    3,PORTA           ;LATCH SLH
1230 1700            BCLR    3,PORTA           ;SLH IS AT D00-D07
```

```
1232 B651            LDA     SUH
1234 B702            STA     PORTC           ;SUH IS AT C0 - C7
     ;                                       SPCH BYTE IS NOW ON
     ;                                       DATA BUS
1236 1E00            BSET    7,PORTA         ;STROBE SPCH SYN
1238 1F00            BCLR    7,PORTA         ;REMOVE RESET & DRIVES BUSY HI
123A 1701            BCLR    3,PORTB
123C 9D              NOP
123D 1601            BSET    3,PORTB
123F B68D            LDA     SAMPLE
1241 B165            CMP     TH1
1243 250F            BCS     MINCNT
1245 4F       ONMESS CLRA
1246 B154            CMP     BLH
1248 271A            BEQ     OU
124A 3A54     IN     DEC     BLH
124C A6FF            LDA     #$FF
124E B154            CMP     BLH             ;FF - BLH
1250 2718            BEQ     MINUS
1252 2042            BRA     MORBYT
1254 08BAEE   MINCNT BRSET   4,SENSIT,ONMESS ;DON'T COUNT IT IF SET
1257 188A            BSET    4,SENSIT        ;SET MIN BIT TO FLAG A TH1 CROSSO
              VER
1259 3C8C            INC     MINCTR          ;COUNT IT
125B 20E8            BRA     ONMESS
125D 1B40     ALLOVR BCLR    5,RAMBIT
125F 1800            BSET    4,PORTA
1261 1900            BCLR    4,PORTA
1263 81              RTS
1264 B153     OU     CMP     BUH
1266 2706            BEQ     OUT
1268 20E0            BRA     IN
126A 3A53     MINUS  DEC     BUH
126C 2028            BRA     MORBYT
126E 1800     OUT    BSET    4,PORTA         ;RESET SPCH SYN
1270 1900            BCLR    4,PORTA
1272 3859            LSL     SILREG          ;X 2
1274 B659            LDA     SILREG
1276 2710            BEQ     HOP             ;NO SILENCE
1278 A106            CMP     #$06
127A 2602            BNE     NOT160
127C A608            LDA     #$8
127E CD110A   NOT160 JSR     WAIT
1281 014204          BRCLR   0,ALLBIT,HOP
1284 1142            BCLR    0,ALLBIT
1286 20F6            BRA     NOT160
1288 3A56     HOP    DEC     NUMWRD
128A 2605            BNE     TINUE
128C 1342            BCLR    1,ALLBIT        ;SILENCE AFTER WRD
128E 1D40            BCLR    6,RAMBIT        ;IN MESAGE BIT ROUTINE
1290 81              RTS
     ;
     ;
     ;
1291 3C57     TINUE  INC     WRDOFF          ;MESSAGE TABLE OFFSET
1293 CC1159          JMP     NEXWRD
1296 3C52     MORBYT INC     SLH
1298 2602            BNE     CUM
129A 3C51            INC     SUH
129C 4F       CUM    CLRA
129D CC1209          JMP     ZZSPK
     ;
     ; END OF MESAGE S.R.
     ;
     ; VENTILATION ROUTINE
     ;
12A0 9A       VENT   CLI
12A1 CD1036          JSR     CLRAMO          ;CLR RAM
12A4 A632            LDA     #$32
12A6 B765            STA     TH1
12A8 A603            LDA     #$03            ;SV LAMP # IS 3
12AA CD1101          JSR     LAMPON          ;TURN ON SVLAMP
```

```
12AD AE02            LDX     #$02
12AF BF64            STX     FIRST
12B1 BE64    TALKV   LDX     FIRST
12B3 CD1122          JSR     MESAGE       ;MESS. NOS. 2 THRU 8
12B6 3C64            INC     FIRST
12B8 B664            LDA     FIRST
12BA A109            CMP     #$09
12BC 26F3            BNE     TALKV
12BE 1742    SVAGIN  BCLR    3,ALLBIT     ;A/D BIT
12C0 CD16C1          JSR     AD1          ;GET A VENTILATION SAMPLE
12C3 B666            LDA     MAXVAL
12C5 A17D            CMP     #$7D         ;1.25 LITERS

12C7 243B            BCC     V1
12C9 A602            LDA     #$2
12CB B168            CMP     BADC1        ;THIRD TIME "TOO SHALLOW"?
12CD 260E            BNE     V2           ;NO
12CF 3F68            CLR     BADC1        ;YES - SUGGEST PROBLEM
12D1 AE09            LDX     #$09
12D3 CD1122          JSR     MESAGE       ;MESSAGE NO. 9
12D6 AE0A            LDX     #$0A
12D8 CD1122          JSR     MESAGE       ;MESSAGE NO. 10
12DB 2007            BRA     V3
12DD 3C68    V2      INC     BADC1
12DF AE0B            LDX     #$B
12E1 CD1122          JSR     MESAGE       ;MESS #11
12E4 3C69    V3      INC     BADC
12E6 3F6A            CLR     GOODC
12E8 A605            LDA     #$5
12EA B169            CMP     BADC         ;5 ERRORS TOTAL
12EC 2721            BEQ     V6           ;YES
12EE AE0C    V4      LDX     #$0C         ;NO
12F0 CD1122          JSR     MESAGE       ;MESS #12
12F3 AD03            BSR     MOVIT
12F5 CC12BE          JMP     SVAGIN
             ;
             ;       MOVIT SR
             ;
12F8 1C8A    MOVIT   BSET    6,SENSIT
12FA CD16C1          JSR     AD1
12FD B68B            LDA     ADVAL
12FF B165            CMP     TH1
1301 24F5            BCC     MOVIT
1303 81              RTS
             ;
             ;       END OF MOVIT SR
             ;
             ;
1304 A196    V1      CMP     #$96         ;1.5 LITERS
1306 2412            BCC     V5           ;YES
1308 AE0E            LDX     #$E          ;NO
130A CD1122          JSR     MESAGE       ;MESS 14
130D 20D5            BRA     V3
130F 3F68    V6      CLR     BADC1
1311 3F69            CLR     BADC
1313 AE0D            LDX     #$D
1315 CD1122          JSR     MESAGE
1318 20D4            BRA     V4
131A A1C8    V5      CMP     #$C8         ;2.0 LITERS 131C 2411            BCC     V7           ;YES
131E 3C6A            INC     GOODC        ;NO
1320 3F69            CLR     BADC
1322 B66A            LDA     GOODC
1324 A102            CMP     #$02         ;VENT DONE WELL TWICE?
1326 270E            BEQ     V8           ;YES
1328 AE0F            LDX     #$0F         ;NO
132A CD1122          JSR     MESAGE       ;MESSAGE NO. 15
132D 20BF            BRA     V4
132F AE11    V7      LDX     #$11
1331 CD1122          JSR     MESAGE       ;MESSAGE #17
1334 20AE            BRA     V3
1336 AE10    V8      LDX     #$10
```

```
1338 CD1122            JSR    MESAGE
                  ;
                  ;
133B AE12            LDX    #$12
133D CD1122          JSR    MESAGE           ;MESS. #18
1340 CD16C1    V9    JSR    AD1              ;GET MAX VAL OF 1ST OF
                  ;                           TWO VENTILATIONS
                  ;
1343 A67C            LDA    #$7C             ;LOAD VENTILATION BRACKET VALUES
1345 B76B            STA    ABLE
1347 A695            LDA    #$95
1349 B76C            STA    BAKER
134B A6C8            LDA    #$C8
134D B76D            STA    CHUCK
134F A6E1            LDA    #$E1
1351 B76E            STA    DOG
1353 CD174B          JSR    SCORC1           ;COMMENT ON 2 VENTS.
1356 ADA0            BSR    MOVIT
1358 3C6F            INC    MAXC
135A A602            LDA    #$02
135C B16F            CMP    MAXC             ;2 VENTILATIONS COMPLETED?
135E 2702            BEQ    V10              ;YES
1360 20DE            BRA    V9               ;NO
1362 3F6F      V10   CLR    MAXC
1364 B171            CMP    CBIN2            ;BOTH ARE GOOD?
1366 2707            BEQ    V11              ;YES
1368 AE18            LDX    #$18             ;NO
136A CD1122          JSR    MESAGE           ;MESS. #24
136D 2019            BRA    V12              ;GIVE 2 BREATHS AGAIN
                  ;
                  ;
136F A605      V11   LDA    #$05             ;CP LAMP IS #5
1371 CD1101          JSR    LAMPON           ;TURN ON CP LAMP
1374 A654            LDA    #$54             ;CAUSE IT TO BLINK
1376 CD1744          JSR    LAMPS
1379 AE19            LDX    #$19
137B CD1122          JSR    MESAGE           ;MESS. #25
137E A650            LDA    #$50
1380 CD1744          JSR    LAMPS            ;UNBLINK CP LAMP
1383 A603            LDA    #$03
1385 CD1101          JSR    LAMPON           ;TURN VENT LAMP BACK ON
1388 3F70      V12   CLR    CBIN1
138A 3F71            CLR    CBIN2
138C 3F72            CLR    CBIN3
138E 20B0            BRA    V9
                  ;
                  ; END OF VENTILATION ROUTINE
                  ;
                  ; CAROTID PULSE ROUTINE
                  ;
1390 9A        CP    CLI
1391 A605            LDA    #$05
1393 CD1101          JSR    LAMPON           ; TURN ON CP LAMP.
1396 1A01            BSET   5,PORTB          ;ACTIVATE CP XDUCER
1398 AE1A            LDX    #$1A
139A BF64            STX    FIRST
139C BE64      TALKCP LDX   FIRST
139E CD1122          JSR    MESAGE           ;MESS. NOS. 26 THRU 29
13A1 3C64            INC    FIRST
13A3 B664            LDA    FIRST
13A5 A11E            CMP    #$1E
13A7 26F3            BNE    TALKCP
13A9 A6F0            LDA    #$F0
13AB CD110A          JSR    WAIT             ;WAIT 4 SECONDS
13AE 4F              CLRA                    ;TURN ON HPLAMP
13AF CD1101          JSR    LAMPON
13B2 A654            LDA    #$54
13B4 CD1744          JSR    LAMPS            ;CAUSE IT TO BLINK
13B7 AE4E            LDX    #$4E
13B9 CD1122          JSR    MESAGE           ;MESS. #78 SUGGEST H.P. EXERCISE
13BC A650            LDA    #$50
13BE CD1744          JSR    LAMPS            ;UNBLINK
```

```
13C1 20CD              BRA     CP
                ;
                ; END OF CAROTID PULSE ROUTINE
                ;
                ; HAND POSITION ROUTINE
                ;
13C3 9A         HP      CLI
13C4 CD1036             JSR     CLRAMO          ;CLR RAM
13C7 4F                 CLRA
13C8 CD1101             JSR     LAMPON          ;H.P. LAMP IS NO. 0
13CB AE1E               LDX     #$1E
13CD BF64               STX     FIRST
13CF BE64       TALKHP  LDX     FIRST
13D1 CD1122             JSR     MESAGE          ;MESS. NOS. 30 THRU 34
13D4 3C64               INC     FIRST
13D6 B664               LDA     FIRST
13D8 A123               CMP     #$23
13DA 26F3               BNE     TALKHP
13DC A619       AGINHP  LDA     #$19            ;THRESHOLD VALUE TO
13DE B765               STA     TH1             ;AVOID FALSE STARTS
13E0 1642               BSET    3,ALLBIT        ;ADC BIT
13E2 1E8A               BSET    7,SENSIT        ;IN HP ROUTINE
13E4 CD16C1             JSR     AD1             ;ROUTINE WILL RETURN
                ;                                WITH H.P. DATA IN
                ;                                H.P. STOR
                ;
13E7 B663               LDA     HPSTOR          ;H.P. = F MEANS GOOD
13E9 A10F               CMP     #$F
13EB 262E               BNE     BAD
13ED 3F69               CLR     BADC
13EF 3C6A               INC     GOODC
13F1 B66A               LDA     GOODC
13F3 A102               CMP     #$02
13F5 2707               BEQ     GOOD
13F7 AE23               LDX     #$23
13F9 CD1122             JSR     MESAGE          ;MESS #35
13FC 20DE               BRA     AGINHP
13FE CD1036     GOOD    JSR     CLRAMO
1401 A601               LDA     #$01
1403 CD1101             JSR     LAMPON          ;TURN ON SCC LAMP
1406 A654               LDA     #$54
1408 CD1744             JSR     LAMPS           ;BLINK IT
140B AE24               LDX     #$24
140D CD1122             JSR     MESAGE          ;MESS. #36
1410 A650               LDA     #$50
1412 CD1744             JSR     LAMPS           ;UNBLINK IT
1415 4F                 CLRA
1416 CD1101             JSR     LAMPON          ;HP LAMP BACK ON
1419 20C1               BRA     AGINHP
141B 3F6A       BAD     CLR     GOODC
141D 3C69               INC     BADC
141F B669               LDA     BADC
1421 A105               CMP     #$05            ;TOTAL OF 5 BAD TRIES ?
1423 2513               BCS     ON1             ;NO
1425 3F69               CLR     BADC            ;YES
1427 AE25               LDX     #$25
1429 CD1122             JSR     MESAGE          ;MESS. #37
142C AE0D               LDX     #$0D
142E CD1122             JSR     MESAGE          ;MESS. #13
1431 AE0C               LDX     #$0C
1433 CD1122             JSR     MESAGE
1436 20A4               BRA     AGINHP
1438 CD169A     ON1     JSR     HPCHEK
143B 209F               BRA     AGINHP
                ;
                ; END OF H.P. ROUTINE
                ;
                ; SINGLE CHEST COMPRESSION ROUTINE
                ;
143D 9A         SCC     CLI                     ;CLR SEQ. RAM
143E CD1036             JSR     CLRAMO
1441 A632               LDA     #$32
```

```
1443 B765           STA    TH1
1445 A601           LDA    #$01
1447 CD1101         JSR    LAMPON          ;SCC LAMP # IS 01
144A AE2A           LDX    #$2A
144C CD1122         JSR    MESAGE          ;MESS. #42
144F AE2B           LDX    #$2B
1451 CD1122         JSR    MESAGE          ;MESS #43
1454 AE08           LDX    #$08
1456 CD1122         JSR    MESAGE          ;MESS. #8
1459 1642    RUNC1  BSET   3,ALLBIT        ;ADC BIT
145B CD16C1         JSR    AD1
145E B663           LDA    HPSTOR
1460 A10F           CMP    #$F
1462 270A           BEQ    UP              ;H.P. IS OK
1464 AE25           LDX    #$25
1466 CD1122         JSR    MESAGE
1469 CD169A         JSR    HPCHEK          ;H.P. IS N.G. COMMENT & TRY AGAIN
146C 20EB           BRA    RUNC1
146E B666    UP     LDA    MAXVAL
1470 A17D           CMP    #$7D
1472 2418           BCC    UP1             ;MAXVAL IS GREATER THAN 1.25 IN

1474 A603           LDA    #$03
1476 B168           CMP    BADC1
1478 2609           BNE    UP6
147A 3F68           CLR    BADC1
147C AE2D           LDX    #$2D
147E CD1122         JSR    MESAGE          ;MESS. #45
1481 2072           BRA    CLOSER
1483 3C68    UP6    INC    BADC1
1485 AE2C           LDX    #$2C
1487 CD1122         JSR    MESAGE          ;MESS. #44
148A 2069           BRA    CLOSER
148C A196    UP1    CMP    #$96            ;1.5 IN.
148E 2407           BCC    UP2
1490 AE2E           LDX    #$2E
1492 CD1122         JSR    MESAGE          ;MESS. #46
1495 205E           BRA    CLOSER
                    ;
                    ;
1497 A1C9    UP2    CMP    #$C9            ;2.0 IN.
1499 2451           BCC    UP3
149B 3F69           CLR    BADC
149D 3C6A           INC    GOODC
149F AE0F           LDX    #$0F
14A1 CD1122         JSR    MESAGE          ;MESS. #15
14A4 B66A           LDA    GOODC
14A6 A103           CMP    #$03            ;GOODC - 3
14A8 2707           BEQ    BYBY
14AA AE0C    UP5    LDX    #$C
14AC CD1122         JSR    MESAGE
14AF 201F           BRA    UP7
14B1 3F6A    BYBY   CLR    GOODC
14B3 3F69           CLR    BADC
14B5 3F68           CLR    BADC1
14B7 A602           LDA    #$02
14B9 CD1101         JSR    LAMPON          ;TURN ON CCR LAMP
14BC A654           LDA    #$54
14BE CD1744         JSR    LAMPS           ;CAUSE IT TO BLINK
14C1 AE31           LDX    #$31
14C3 CD1122         JSR    MESAGE
14C6 A650           LDA    #$50
14C8 CD1744         JSR    LAMPS           ;UNBLINK IT
14CB A601           LDA    #$01            ;TURN ON SCC LAMP
14CD CD1101         JSR    LAMPON
14D0 1C8A    UP7    BSET   6,SENSIT        ;SAIDIT BIT
14D2 CD16C1         JSR    AD1
14D5 B68B           LDA    ADVAL
14D7 B165           CMP    TH1             ;MAXVAL - TH1
14D9 2403           BCC    LETGO
14DB CC1459         JMP    RUNC1
14DE AE29    LETGO  LDX    #$29
```

```
14E0 CD1122            JSR     MESAGE
14E3 20EB              BRA     UP7
14E5 AE30     UP4      LDX     #$30
14E7 CD1122            JSR     MESAGE          ;MESS. #48
14EA 2009              BRA     CLOSER
14EC A1F0     UP3      CMP     #$F0            ;MAXVAL - F0
14EE 24F5              BCC     UP4
14F0 AE2F              LDX     #$2F
14F2 CD1122            JSR     MESAGE          ;MESS. #47
14F5 3F6A     CLOSER   CLR     GOODC
14F7 3C69              INC     BADC
14F9 A605              LDA     #$05
14FB B169              CMP     BADC            ;5 - BADC
14FD 26AB              BNE     UP5
14FF 3F69              CLR     BADC
1501 3F68              CLR     BADC1
1503 AE0D              LDX     #$0D
1505 CD1122            JSR     MESAGE          ;MESS #13
1508 20A0              BRA     UP5
              ;
              ; END OF SCC ROUTINE
              ;
              ; CHEST COMPRESSION RHYTHM ROUTINE
              ;
150A 9A       CCR      CLI
150B A602              LDA     #$02            ;TURN ON CCR LAMP
150D CD1101            JSR     LAMPON
1510 AE32              LDX     #$32
1512 CD1122            JSR     MESAGE          ;MESS. #50
1515 AE08              LDX     #$08
1517 CD1122            JSR     MESAGE          ;MESS. #8
151A CD1036   CCRA     JSR     CLRAMO          ;CLEAR RAM
151D A632              LDA     #$32
151F B765              STA     TH1             ;COMPRESSION THRESHOLD DETECT
1521 A67C              LDA     #$7C
1523 B76B              STA     ABLE
1525 A695              LDA     #$95
1527 B76C              STA     BAKER
1529 A6C8              LDA     #$C8
152B B76D              STA     CHUCK
152D A6E1              LDA     #$E1
152F B76E              STA     DOG
1531 1642              BSET    3,ALLBIT        ;ADCBIT
1533 1A8A              BSET    5,SENSIT        ;1ST CC BIT
1535 CD16C1   CCR1     JSR     AD1
1538 B663              LDA     HPSTOR
153A A10F              CMP     #$F
153C 2712              BEQ     CCR2            ;H.P. IS OK
153E 3F6F              CLR     MAXC
1540 AE25              LDX     #$25
1542 CD1122            JSR     MESAGE
1545 CD169A            JSR     HPCHEK          ;H.P. IS NG COMMENT AND TRY AGAIN
1548 20D0              BRA     CCRA
154A CC160A   CCR13    JMP     CCR3
154D CC1605   CCR14    JMP     CCRB
1550 A670     CCR2     LDA     #$70
1552 B709              STA     TCR
1554 0A8AF3            BRSET   5,SENSIT,CCR13
1557 B608              LDA     TDR
1559 BE6F              LDX     MAXC
155B 5A                DECX
155C E77A              STA     PERIOD,X
155E B796              STA     NEWNUM
1560 CD1613            JSR     ADDIT           ;SUM PERIODS IN TOTMSB,TOTLSB
1563 3F08     CCR4     CLR     TDR             ;START NEW COUNT
1565 CD174B            JSR     SCORC1          ;COMMENT ON COMPRESSION DEPTH
1568 1C8A     COMEUP   BSET    6,SENSIT        ;SAID IT BIT
156A CD16C1            JSR     AD1
156D B68B              LDA     ADVAL
156F A12D              CMP     #$2D
1571 2514              BCS     REST
1573 B608              LDA     TDR
```

```
1575 A1CF            CMP      #$CF
1577 2502            BCS      TIMEUP
1579 20ED            BRA      COMEUP
157B AE49     TIMEUP LDX      #$49
157D CD1122          JSR      MESAGE        ;MESS. # 73
1580 AE4A            LDX      #$4A
1582 CD1122          JSR      MESAGE        ;MESS. # 74
1585 2093            BRA      CCRA
1587 A60E     REST   LDA      #$0E
1589 B16F            CMP      MAXC          ;14 - MAXC
158B 26C0            BNE      CCR14
158D AD06            BSR      MEAN          ;15 CC ARE DONE. SUM IS IN TOTMSB
                & TOTLSB
              ;                             ;NOW COMPUTE AVG PERIOD
158F B69C            LDA      QUOTNT
1591 B778            STA      XBAR
1593 2013            BRA      AVGDEV
              ; COMPUTE THE MEAN SR
              ;
1595 B695     MEAN   LDA      TOTMSB        ;LOAD TOTALS
1597 B799            STA      DNDMSB
1599 B694            LDA      TOTLSB
159B B79A            STA      DNDLSB
159D 4F              CLRA                   ;LOAD DIVISOR
159E B797            STA      SORMSB
15A0 A60E            LDA      #$E
15A2 B798            STA      SORLSB
15A4 CD161E          JSR      DIV           ;ANSWER IS IN QUOTNT
15A7 81              RTS
              ;
              ;
15A8 3F96     AVGDEV CLR      NEWNUM
15AA 3F94            CLR      TOTLSB
15AC 3F95            CLR      TOTMSB
15AE 5F              CLRX                   ;COMPUTE SUM OF X-XBAR/14 (AVG DE
                VIATION)
15AF E67A     LOOP4  LDA      PERIOD,X      ;SAMPLE TO A
15B1 B078            SUB      XBAR
15B3 2401            BCC      POSTIV
15B5 40              NEGA                   ;POSITIVE # ONLY
15B6 E77A     POSTIV STA      PERIOD,X
15B8 B796            STA      NEWNUM        ;ADD IT TO PREV. TOTAL
15BA CD1613          JSR      ADDIT         ;SUM OF ABSOLUTE VAL. OF X-XBAR
              ;                             ;IS ADDED TO TOTMSB ,TOTLSB
15BD 5C              INCX
15BE A30E            CPX      #$E
15C0 26ED            BNE      LOOP4         ;14 X-XBAR ARE IN PERIOD,0 - PERI
                OD,13
15C2 ADD1            BSR      MEAN          ;COMPUTE AVG DEVIATION
15C4 B69C            LDA      QUOTNT
15C6 B779            STA      SIGMA
15C8 3F6F            CLR      MAXC
15CA CD177C          JSR      SCORC2        ;GIVE REPORT ON CC DEPTHS
15CD A640            LDA      #$40
15CF CD110A          JSR      WAIT
15D2 CD17C5          JSR      SCORC3        ;GIVE REPORT ON CC RHYTHM
15D5 A640            LDA      #$40
15D7 CD110A          JSR      WAIT
15DA 048A1F          BRSET    2,SENSIT,CCR5 ;SC BIT
15DD 028A2F          BRSET    1,SENSIT,CCR11 ;RHYTHM BIT
15E0 A604            LDA      #$4
15E2 CD1101          JSR      LAMPON        ;HT LAMP
15E5 A654            LDA      #$54
15E7 CD1744          JSR      LAMPS         ;BLINK IT
15EA AE4C            LDX      #$4C
15EC CD1122          JSR      MESAGE        ;MESS. #76
15EF A650            LDA      #$50
15F1 CD1744          JSR      LAMPS         ;STOP BLINK
15F4 A602            LDA      #$02
15F6 CD1101          JSR      LAMPON        ;TURN CCR LAMP BACK ON
15F9 CC151A   CCR7   JMP      CCRA          ;START AGAIN
15FC 158A     CCR5   BCLR     2,SENSIT
```

```
15FE AE4A     CCR8    LDX     #$4A
1600 CD1122           JSR     MESAGE          ;MESS. #74
1603 20F4             BRA     CCR7
1605 3C6F     CCR9    INC     MAXC
1607 CC1535           JMP     CCR1
160A 1B8A     CCR3    BCLR    5,SENSIT        ;1ST CC BIT
160C CC1563           JMP     CCR4
160F 138A     CCR11   BCLR    1,SENSIT        ;RHYTHM BIT
1611 20EB             BRA     CCR8
              ;
              ; END OF CCR SEQUENCE
              ;
              ;
              ;
              ; ADD 8 BIT NUMBERS
              ;
              ;
1613 B694     ADDIT   LDA     TOTLSB
1615 BB96             ADD     NEWNUM
1617 B794             STA     TOTLSB
1619 2402             BCC     FIN
161B 3C95             INC     TOTMSB
161D 81       FIN     RTS
              ;
              ;
              ; DIVIDE 16 BIT X 16 BIT
              ;
              ;
161E A602     DIV     LDA     #$2
1620 B79B             STA     TEMP2           ;SHIFT CTR
1622 B697             LDA     SORMSB          ;MSBYTE OF DIVSOR
1624 BE98             LDX     SORLSB          ;LSBYTE OF DIVSOR
1626 2608             BNE     NOZERO          ;CHECK FOR DIV BY 0
1628 4D               TSTA
1629 2606             BNE     DIVO1
162B A6FF             LDA     #$FF
162D B79C             STA     QUOTNT
162F 81               RTS                     ;RET WITH FF IF DIV BY 0
1630 4D       NOZERO  TSTA                    ;SHIFT ENTIRE DIVSOR LEFT
                                              ;TILL SIGN BIT = 1
1631 2B06     DIVO1   BMI     OUTD            ;SIGN BIT = 1
1633 3C9B     LOOP3   INC     TEMP2           ;INC SHIFT COUNT
1635 58               LSLX
1636 49               ROLA
1637 2AFA             BPL     LOOP3           ;KEEP SHIFTING
1639 B797     OUTD    STA     SORMSB          ;RESTORE DIVSOR
163B BF98             STX     SORLSB          ;
163D 5F               CLRX                    ;CLEAR PLACE FOR QUOTIENT
              ;
              ; MAIN LOOP
              ;
163E B69A     LOOP    LDA     DNDLSB          ;DIVDND -DIVSOR = NEW DIVDND
1640 B098             SUB     SORLSB
1642 B79A             STA     DNDLSB
1644 B699             LDA     DNDMSB
1646 B297             SBC     SORMSB
1648 2409             BCC     ZOT
164A B69A             LDA     DNDLSB
164C BB98             ADD     SORLSB
164E B79A             STA     DNDLSB
1650 58               LSLX
1651 2004             BRA     OVER
1653 B799     ZOT     STA     DNDMSB
1655 99               SEC
1656 59               ROLX
1657 49       OVER    ROLA
1658 3497             LSR     SORMSB
165A 3698             ROR     SORLSB
165C 3A9B             DEC     TEMP2
165E 26DE             BNE     LOOP
1660 44               LSRA
1661 56               RORX
```

```
1662 9F              TXA
1663 A900            ADC     #$0
1665 B79C            STA     QUOTNT
1667 81              RTS
                ;
                ;
                ;
                ; HEIMLICK THRUST ROUTINE
                ;
                ;
1668 9A         HT      CLI
1669 A604               LDA     #$04
166B CD1101             JSR     LAMPON          ;TURN ON HT LAMP
166E AE4F               LDX     #$4F
1670 BF64               STX     FIRST
1672 BE64       TALKHT  LDX     FIRST
1674 CD1122             JSR     MESAGE          ;VOICE MESSAGES
1677 3C64               INC     FIRST
1679 B664               LDA     FIRST           ;79 THRU 81
167B A152               CMP     #$52
167D 26F3               BNE     TALKHT
167F A6F0               LDA     #$F0
1681 CD110A             JSR     WAIT            ;WAIT 4 SECS.
1684 A603               LDA     #$03            ;BLINK VENT LAMP
1686 CD1101             JSR     LAMPON
1689 A654               LDA     #$54
168B CD1744             JSR     LAMPS
168E AE52               LDX     #$52
1690 CD1122             JSR     MESAGE          ;MESS. #82
1693 A650               LDA     #$50
1695 CD1744             JSR     LAMPS           ;UNBLINK VENT. LAMP
1698 20CE               BRA     HT
                ;
                ;
                ;
                ; HAND POSITION CHECK SUB-ROUTINE
                ; (ENTER WITH H.P. DATA IN H.P. STOR)
                ;
169A 056316     HPCHEK  BRCLR   2,HPSTOR,HI
169D 03630C     HP2     BRCLR   1,HPSTOR,TOOLOW
16A0 016317     HP3     BRCLR   0,HPSTOR,OFFC
16A3 076314             BRCLR   3,HPSTOR,OFFC
16A6 AE29       HP4     LDX     #$29
16A8 CD1122             JSR     MESAGE          ;MESS. #41
16AB 81                 RTS
16AC AE27       TOOLOW  LDX     #$27
16AE CD1122             JSR     MESAGE          ;MESS. #39
16B1 20ED               BRA     HP3
16B3 AE26       HI      LDX     #$26
16B5 CD1122             JSR     MESAGE          ;MESS. #38
16B8 20E3               BRA     HP2
16BA AE28       OFFC    LDX     #$28
16BC CD1122             JSR     MESAGE          ;MES. #40
16BF 20E5               BRA     HP4
                ;
                ; END OF HPCHECK SUB-ROUTINE
                ;
                ; THIS ROUTINE GETS THE MAXIMUM VALUE OF A CHEST
                ; COMPRESSION DEPTH ,HAND POSITION DATA OR THE MAXIMUM
                ; VENTILATION.
                ;
                ; A TO D SUB-ROUTINE
                ;
16C1 3F76       AD1     CLR     SMPOL1          ;CLR RAM
16C3 3F77               CLR     SMPOL2
16C5 A655               LDA     #$55
16C7 CD1744             JSR     LAMPS           ;TURN ON WAIT LAMP
16CA 1701       RUNC2   BCLR    3,PORTB         ;START A/D CONVER.
16CC 9D                 NOP                     ;DRIVE A/D INTR HI
16CD 9D                 NOP
16CE 9D                 NOP
```

```
16CF 1601            BSET    3,PORTB
16D1 0803FD   CONV   BRSET   4,PORTD,CONV    ;WAIT HERE TILL A/D INTR
16D4                                         ;GOES LOW AT END OF CONV.
16D4 074204          BRCLR   3,ALLBIT,ADV2
16D7 1F01            BCLR    7,PORTB         ;START READ OF A/D CC
16D9 2002            BRA     READO
16DB 1901     ADV2   BCLR    4,PORTB         ;START READ A/D VENT
16DD 1600     READO  BSET    3,PORTA         ;LATCH AD DATA INTO IN PORT
16DF 9D              NOP
16E0 9D              NOP
16E1 9D              NOP
16E2 1700            BCLR    3,PORTA
16E4 1E01            BSET    7,PORTB         ;REMOVE READ A/D
16E6 1801            BSET    4,PORTB
16E8 4F              CLRA
16E9 B706            STA     CDDR            ;PORTC BECOMES INPUT PORT
16EB 1401            BSET    2,PORTB         ;OUTPUT A/D DATA FROM EXTER.
16ED 9D              NOP                     ;I/O LATCHES TO I/O OUTPUTS
16EE B602            LDA     PORTC
16F0 1501            BCLR    2,PORTB         ;3 STATE I/O OUTPUTS
16F2 B767            STA     SMPNEW
16F4 B78B            STA     ADVAL           ;FOR USE ON WAY DOWN
16F6 A6FF            LDA     #$FF
16F8 B706            STA     CDDR            ;PORTC BACK TO OUTPUT PORT
16FA 0C8A08          BRSET   6,SENSIT,JUSTAD ;FOR RELEASE OF CC
16FD B665            LDA     TH1
16FF B167            CMP     SMPNEW          ;TH1 - SAMPLE
1701 2506            BCS     RUNC3
1703 20C5            BRA     RUNC2
1705 1D8A     JUSTAD BCLR    6,SENSIT        ;SAIDIT BIT
1707 2033            BRA     TELLIT
              ;
              ;
1709 1442     RUNC3  BSET    2,ALLBIT        ;TH1BIT
170B 1C01            BSET    6,PORTB         ;EN A (HP) SIDE OF MUX
170D B603            LDA     PORTD           ;HP SW DATA IS A3-A0
              ;                              INPUT HP SW DATA
170F 1D01            BCLR    6,PORTB         ;EN B (MEMBRANE SW) SIDE OF MUX
1711 A40F            AND     #$0F            ;ZERO A7-A3
1713 B763            STA     HPSTOR          ;HAND POSITION SW DATA
1715 0E8A1C          BRSET   7,SENSIT,GOTIT
1718 B667            LDA     SMPNEW
171A AB05            ADD     #$5
171C B176            CMP     SMPOL1          ;SMPNEW - SMPOLD
171E 2518            BCS     RUNC5           ;SMPNEW NOT GREATER
1720 B676            LDA     SMPOL1
1722 B177            CMP     SMPOL2          ;SMPOL1 - SMPOL2
1724 2406            BCC     BIGGER
1726 B677            LDA     SMPOL2
1728 B776            STA     SMPOL1
172A 209E            BRA     RUNC2
172C B777     BIGGER STA     SMPOL2
172E B667            LDA     SMPNEW
1730 B776            STA     SMPOL1
1732 2096            BRA     RUNC2
1734 1F8A     GOTIT  BCLR    7,SENSIT        ;HP ROUTINE BIT
1736 2004            BRA     TELLIT
1738 B676     RUNC5  LDA     SMPOL1
173A B766            STA     MAXVAL
173C 1542     TELLIT BCLR    2,ALLBIT
173E A650            LDA     #$50            ;CLR WAIT BIT
1740 CD1744          JSR     LAMPS           ;TURN OFF WAIT LAMP
1743 81              RTS
              ; END OF AD1 S.R. ON RETURN MAX. VALUE
              ; OF COMPRESSION IS IN MAXUAL AND HAND
              ; POSITION DATA IS IN HP STOR AND ACCUM.
              ;
              ;
              ; LAMPS SUB ROUTINE
              ;
1744 B700     LAMPS  STA     PORTA           ;RAISE APPRO. BITS
```

```
 1746 1D00              BCLR    6,PORTA          ;DROP STROBE
 1748 1900              BCLR    4,PORTA
 174A 81                RTS
                    ;
                    ; SCORC1 SUB-ROUTINE
                    ;
                    ;THIS ROUTINE GIVES VOICE COACHING DURING EACH CHEST COMPRESSION
                    ;# OF TOO DEEP,TOO SHALLOW,&GOOD ONES ARE TALLIED
                    ;
                    ;
 174B B666        SCORC1  LDA    MAXVAL
 174D AE13                LDX    #$13            ;INITIALIZE X TO
                    ;                             MESS. NO. 19
 174F B16B                CMP    ABLE
 1751 240D                BCC    SCOR1
 1753 3C70        SCOR5   INC    CBIN1
                    ;
                    ;
                    ;
 1755 1701        SCOR4   BCLR   3,PORTB          ;START A/D CONV
 1757 9D                  NOP
 1758 1601                BSET   3,PORTB
 175A 198A                BCLR   4,SENSIT         ;FLAGS A NEW MAX TO MES. SR
 175C CD1122              JSR    MESAGE           ;COMMENT ON DEPTH
                    ;                             OF CC
 175F 81                  RTS
 1760 5C          SCOR1   INCX                    ;INDEX TO NEXT HIGHER MESS.
 1761 B16C                CMP    BAKER            ;A - 150
 1763 2402                BCC    SCOR6            ;MAXVAL IS HIGHER
 1765 20EC                BRA    SCOR5            ;TALLY IN SAME BIN
 1767 5C          SCOR6   INCX
 1768 B16D                CMP    CHUCK
 176A 2404                BCC    SCOR7
 176C 3C71                INC    CBIN2
 176E 20E5                BRA    SCOR4
 1770 5C          SCOR7   INCX                    ;INDEX TO NEXT HIGHER MESS.
 1771 B16E                CMP    DOG
 1773 2404                BCC    SCOR8
 1775 3C72        SCOR2   INC    CBIN3
 1777 20DC                BRA    SCOR4
 1779 5C          SCOR8   INCX                    ;INDEX TO NEXT HIGHER MESS.
 177A 20F9                BRA    SCOR2            ;SAME BIN
                    ;
                    ; END OF SCORC1 SUB-ROUTINE
                    ;
                    ; SCORC2 SUB-ROUTINE
                    ;
                    ; VOCALALIZATION OF OVERALL PERFORMANCE WITH RESPECT TO
                    ; DEPTH OF CHEST COMPRESSIONS
                    ;
 177C 158A        SCORC2  BCLR   2,SENSIT         ;SC BIT
 177E A620                LDA    #$20
 1780 CD110A              JSR    WAIT             ;PAUSE BEFOR MESAGE
 1783 BE70                LDX    CBIN1
 1785 270C                BEQ    NXBIN1
 1787 AD34                BSR    NUMBER
 1789 AE2C                LDX    #$2C
 178B CD1122              JSR    MESAGE           ;"TOO SHALLOW"
 178E A620                LDA    #$20
 1790 CD110A              JSR    WAIT             ;PAUSE BEFOR MESAGE
 1793 BE71        NXBIN1  LDX    CBIN2
 1795 270C                BEQ    NXBIN2
 1797 AD24                BSR    NUMBER
 1799 AE15                LDX    #$15             ;"GREAT"
 179B CD1122              JSR    MESAGE
 179E A620                LDA    #$20
 17A0 CD110A              JSR    WAIT             ;PAUSE BEFOR MESAGE
 17A3 BE72        NXBIN2  LDX    CBIN3
 17A5 270C                BEQ    FINE
 17A7 AD14                BSR    NUMBER
 17A9 AE30                LDX    #$30
```

```
17AB CD1122           JSR      MESAGE         ;"TOO DEEP"
17AE A620             LDA      #$20
17B0 CD110A           JSR      WAIT           ;PAUSE BEFOR MESAGE
17B3 A609     FINE    LDA      #$9
17B5 B171             CMP      CBIN2
17B7 2401             BCC      NOGD
17B9 81               RTS
17BA 148A     NOGD    BSET     2,SENSIT       ;FLAG FOR NOT GOOD ENOUGH
17BC 81               RTS
              ;
              ; NUMBER SUB-ROUTINE
              ;
              ;
17BD 9F       NUMBER  TXA                     ;BIN VAL TO A
17BE AB33             ADD      #$33           ;ADD 51
17C0 97               TAX
17C1 CD1122           JSR      MESAGE         ;MESS. #52 - 66
17C4 81               RTS
              ;
              ; END OF SCORC2 SUB-ROUTINE
              ;
              ; SCORC3 SUB-ROUTINE
              ;
              ;THIS ROUTINE VOCALIZES AN ASSESMENT OF THE TIMING
              ;OF THE CC.
              ;
17C5 138A     SCORC3  BCLR     1,SENSIT       ;CC RHYTHM BIT
17C7 B678             LDA      XBAR           ;MEAN PERIOD
17C9 A1B5             CMP      #$B5
17CB 2513             BCS      C31
17CD B679             LDA      SIGMA
17CF A105             CMP      #$05
17D1 252A             BCS      C32
17D3 AE43             LDX      #$43
17D5 CD1122           JSR      MESAGE         ;MESS. #67
17D8 AE33     C33     LDX      #$33
17DA CD1122           JSR      MESAGE         ;MESS #51
17DD 128A             BSET     1,SENSIT       ;RHYTHM BIT
17DF 81       C35     RTS
17E0 A1A2     C31     CMP      #$A2
17E2 250C             BCS      C34
17E4 B679             LDA      SIGMA
17E6 A105             CMP      #$05
17E8 241A             BCC      C36
17EA AE48             LDX      #$48
17EC CD1122           JSR      MESAGE         ;MESS. #72
17EF 81               RTS
17F0 B679     C34     LDA      SIGMA
17F2 A105             CMP      #$05
17F4 2415             BCC      C37
17F6 AE46             LDX      #$46
17F8 CD1122           JSR      MESAGE         ;MESS. #70
17FB 20DB             BRA      C33
17FD AE44     C32     LDX      #$44
17FF CD1122           JSR      MESAGE         ;MESS #68
1802 20D4             BRA      C33
1804 AE47     C36     LDX      #$47
1806 CD1122           JSR      MESAGE         ;MESS. #71
1809 20CD             BRA      C33
180B AE45     C37     LDX      #$45
180D CD1122           JSR      MESAGE         ;MESS. #69
1810 20C6             BRA      C33
              ;
              ; END OF SCORC3 SUB-ROUTINE
              ;
              ;** START OF TABLES **
              ;Index Table
1812 0C       I       DB       $C             ; Msg#  0
1813 00               DB       $0
1814 38               DB       $38            ; Msg#  1
1815 03               DB       $3
1816 38               DB       $38            ; Msg#  2
```

```
1817 11      DB    $11
1818 60      DB    $60     ; Msg#  3
1819 1F      DB    $1F
181A 08      DB    $8      ; Msg#  4
181B 37      DB    $37
181C 14      DB    $14     ; Msg#  5
181D 39      DB    $39
181E 50      DB    $50     ; Msg#  6
181F 3E      DB    $3E
1820 10      DB    $10     ; Msg#  7
1821 52      DB    $52
1822 08      DB    $8      ; Msg#  8
1823 56      DB    $56
1824 3C      DB    $3C     ; Msg#  9
1825 58      DB    $58
1826 0C      DB    $C      ; Msg# 10
1827 67      DB    $67
1828 0C      DB    $C      ; Msg# 11
1829 6A      DB    $6A
182A 18      DB    $18     ; Msg# 12
182B 6D      DB    $6D
182C 18      DB    $18     ; Msg# 13
182D 73      DB    $73
182E 08      DB    $8      ; Msg# 14
182F 79      DB    $79
1830 2C      DB    $2C     ; Msg# 15
1831 7B      DB    $7B
1832 18      DB    $18     ; Msg# 16
1833 86      DB    $86
1834 48      DB    $48     ; Msg# 17
1835 8C      DB    $8C
1836 04      DB    $4      ; Msg# 18
1837 9E      DB    $9E
1838 04      DB    $4      ; Msg# 19
1839 9F      DB    $9F
183A 04      DB    $4      ; Msg# 20
183B A0      DB    $A0
183C 04      DB    $4      ; Msg# 21
183D A1      DB    $A1
183E 04      DB    $4      ; Msg# 22
183F A2      DB    $A2
1840 14      DB    $14     ; Msg# 23
1841 A3      DB    $A3
1842 90      DB    $90     ; Msg# 24
1843 A8      DB    $A8
1844 34      DB    $34     ; Msg# 25
1845 CC      DB    $CC
1846 38      DB    $38     ; Msg# 26
1847 D9      DB    $D9
1848 20      DB    $20     ; Msg# 27
1849 E7      DB    $E7
184A 38      DB    $38     ; Msg# 28
184B EF      DB    $EF
184C 79      DB    $79     ; Msg# 29
184D 00      DB    $0
184E 21      DB    $21     ; Msg# 30
184F 1E      DB    $1E
1850 5D      DB    $5D     ; Msg# 31
1851 26      DB    $26
1852 2D      DB    $2D     ; Msg# 32
1853 3D      DB    $3D
1854 29      DB    $29     ; Msg# 33
1855 48      DB    $48
1856 31      DB    $31     ; Msg# 34
1857 52      DB    $52
1858 79      DB    $79     ; Msg# 35
1859 5E      DB    $5E
185A 29      DB    $29     ; Msg# 36
185B 7C      DB    $7C
185C 11      DB    $11     ; Msg# 37
185D 86      DB    $86
185E 11      DB    $11     ; Msg# 38
```

```
185F  8A         DB    $8A
1860  0D         DB    $D      ; Msg# 39
1861  8E         DB    $8E
1862  29         DB    $29     ; Msg# 40
1863  91         DB    $91
1864  4D         DB    $4D     ; Msg# 41
1865  9B         DB    $9B
1866  49         DB    $49     ; Msg# 42
1867  AE         DB    $AE
1868  11         DB    $11     ; Msg# 43
1869  C0         DB    $C0
186A  55         DB    $55     ; Msg# 44
186B  C4         DB    $C4
186C  19         DB    $19     ; Msg# 45
186D  D9         DB    $D9
186E  11         DB    $11     ; Msg# 46
186F  DF         DB    $DF
1870  09         DB    $9      ; Msg# 47
1871  E3         DB    $E3
1872  35         DB    $35     ; Msg# 48
1873  E5         DB    $E5
1874  AA         DB    $AA     ; Msg# 49
1875  00         DB    $0
1876  1A         DB    $1A     ; Msg# 50
1877  2A         DB    $2A
1878  0A         DB    $A      ; Msg# 51
1879  30         DB    $30
187A  12         DB    $12     ; Msg# 52
187B  32         DB    $32
187C  0E         DB    $E      ; Msg# 53
187D  36         DB    $36
187E  0E         DB    $E      ; Msg# 54
187F  39         DB    $39
1880  0E         DB    $E      ; Msg# 55
1881  3C         DB    $3C
1882  0E         DB    $E      ; Msg# 56
1883  3F         DB    $3F
1884  0E         DB    $E      ; Msg# 57
1885  42         DB    $42
1886  0E         DB    $E      ; Msg# 58
1887  45         DB    $45
1888  0E         DB    $E      ; Msg# 59
1889  48         DB    $48
188A  0E         DB    $E      ; Msg# 60
188B  4B         DB    $4B
188C  0E         DB    $E      ; Msg# 61
188D  4E         DB    $4E
188E  0E         DB    $E      ; Msg# 62
188F  51         DB    $51
1890  16         DB    $16     ; Msg# 63
1891  54         DB    $54
1892  16         DB    $16     ; Msg# 64
1893  59         DB    $59
1894  12         DB    $12     ; Msg# 65
1895  5E         DB    $5E
1896  1A         DB    $1A     ; Msg# 66
1897  62         DB    $62
1898  0E         DB    $E      ; Msg# 67
1899  68         DB    $68
189A  1A         DB    $1A     ; Msg# 68
189B  6B         DB    $6B
189C  0E         DB    $E      ; Msg# 69
189D  71         DB    $71
189E  0E         DB    $E      ; Msg# 70
189F  74         DB    $74
18A0  0E         DB    $E      ; Msg# 71
18A1  77         DB    $77
18A2  16         DB    $16     ; Msg# 72
18A3  7A         DB    $7A
18A4  2E         DB    $2E     ; Msg# 73
18A5  7F         DB    $7F
18A6  1A         DB    $1A     ; Msg# 74
18A7  8A         DB    $8A
```

```
18A8 6A              DB      $6A     ; Msg# 75
18A9 90              DB      $90
18AA 12              DB      $12     ; Msg# 76
18AB AA              DB      $AA
18AC 2A              DB      $2A     ; Msg# 77
18AD AE              DB      $AE
18AE 1E              DB      $1E     ; Msg# 78
18AF B8              DB      $B8
18B0 3A              DB      $3A     ; Msg# 79
18B1 BF              DB      $BF
18B2 5A              DB      $5A     ; Msg# 80
18B3 CD              DB      $CD
18B4 2A              DB      $2A     ; Msg# 81
18B5 E3              DB      $E3
                  ;  L Table
18B6 D2           L  DB      $D2     ;Msg#   0, WEL
18B7 FD              DB      $FD     ;          COME_TO_COACH_ANDY
18B8 27              DB      $27
18B9 FD              DB      $FD     ;Msg#   1, VENTILATION
18BA DB              DB      $DB
18BB 84              DB      $84     ;          OPEN_THE_AIRWAY
18BC F8              DB      $F8     ;          BY
18BD 13              DB      $13
18BE 32              DB      $32     ;          GENTLY
18BF C0              DB      $C0     ;          TILT1
18C0 F9              DB      $F9     ;          ING
18C1 40              DB      $40
18C2 F9              DB      $F9     ;          THE3
18C3 A6              DB      $A6
18C4 73              DB      $73     ;          HEAD
18C5 FE              DB      $FE     ;          WAY_BACK
18C6 CE              DB      $CE
18C7 75              DB      $75     ;Msg#   2, PRESS1
18C8 F9              DB      $F9     ;          DOWN
18C9 3F              DB      $3F
18CA F9              DB      $F9     ;          ON
18CB 78              DB      $78
18CC FA              DB      $FA     ;          THE_MANIKINS
18CD A9              DB      $A9
18CE 2E              DB      $2E     ;          FOREHEAD
18CF DD              DB      $DD     ;          WITH_THE
18D0 8C              DB      $8C     ;          PALM
18D1 74              DB      $74     ;          OF
18D2 69              DB      $69     ;          ONE2
18D3 FC              DB      $FC     ;          HAND
18D4 6B              DB      $6B
18D5 D5              DB      $D5     ;Msg#   3, WITH1
18D6 E5              DB      $E5     ;          YOUR_OTHER
18D7 6B              DB      $6B     ;          HAND
18D8 55              DB      $55     ;          LIFT
18D9 F8              DB      $F8     ;          EITHER
18DA 47              DB      $47
18DB CC              DB      $CC     ;          UNDER_THE
18DC 93              DB      $93     ;          NECK
18DD F9              DB      $F9     ;          NEAR_THE
18DE 4A              DB      $4A
18DF FC              DB      $FC     ;          BASE_OF_THE_HEAD
18E0 07              DB      $7
18E1 FA              DB      $FA     ;          OR
18E2 6D              DB      $6D
18E3 F8              DB      $F8     ;          WITH_THE
18E4 DD              DB      $DD
18E5 53              DB      $53     ;          FINGERTIPS
18E6 CC              DB      $CC     ;          UNDER_THE
18E7 29              DB      $29     ;          BONY_PART
18E8 9B              DB      $9B     ;          OF_THE_JAW
18E9 F8              DB      $F8     ;          NEAR_THE
18EA 4A              DB      $4A
18EB FE              DB      $FE     ;          CHIN
18EC 1F              DB      $1F
18ED FC              DB      $FC     ;Msg#   4, !
18EE 02              DB      $2
```

```
18EF  6A        DB    $6A    ;Msg#  5, PINCH_OFF
18F0  A9        DB    $A9    ;          THE_MANIKINS
18F1  68        DB    $68    ;          NOSTRIL
18F2  FD        DB    $FD    ;          S
18F3  89        DB    $89
18F4  62        DB    $62    ;Msg#  6, OPEN_YOUR_MOUTH
18F5  DF        DB    $DF    ;          WIDE
18F6  9A        DB    $9A    ;          TAKE_A
18F7  33        DB    $33    ;          DEEP
18F8  88        DB    $88    ;          P
18F9  FB        DB    $FB    ;          BREATH
18FA  08        DB    $8
18FB  19        DB    $19    ;          AND_MAKE_A
18FC  B2        DB    $B2    ;          TIGHT_SEAL
18FD  D1        DB    $D1    ;          WITH
18FE  A9        DB    $A9    ;          THE_MANIKINS
18FF  46        DB    $46    ;          MOUTH
1900  04        DB    $4     ;          ANND
1901  FC        DB    $FC    ;          BLOW1
1902  0F        DB    $F
1903  C2        DB    $C2    ;          TRY_A
1904  FA        DB    $FA    ;          SINGLE
1905  95        DB    $95
1906  FC        DB    $FC    ;          VENTILATION
1907  DB        DB    $DB
1908  F9        DB    $F9    ;Msg#  7, I_WILL
1909  4C        DB    $4C
190A  F8        DB    $F8    ;          TELL_YOU_HOW_YOU_DID
190B  C3        DB    $C3
190C  FC        DB    $FC    ;Msg#  8, MORE_AIR
190D  8F        DB    $8F
190E  21        DB    $21    ;Msg#  9, BE_SURE_THAT
190F  E1        DB    $E1    ;          YOURE
1910  9E        DB    $9E    ;          TAKING_A
1911  33        DB    $33    ;          DEEP
1912  F9        DB    $F9    ;          P
1913  88        DB    $88
1914  FA        DB    $FA    ;          BREATH
1915  08        DB    $8
1916  15        DB    $15    ;          AND_KEEPING_A
1917  B2        DB    $B2    ;          TIGHT_SEAL
1918  D1        DB    $D1    ;          WITH
1919  A9        DB    $A9    ;          THE_MANIKINS
191A  68        DB    $68    ;          NOSTRIL
191B  FC        DB    $FC    ;          S
191C  89        DB    $89
191D  0A        DB    $A     ;Msg# 10, BLOW2
191E  FC        DB    $FC    ;          HARDER
191F  6F        DB    $6F
1920  C4        DB    $C4    ;Msg# 11, TRY_IT
1921  F8        DB    $F8    ;          AGAIN
1922  03        DB    $3
1923  71        DB    $71    ;Msg# 12, PLEASE_ASK
1924  F9        DB    $F9    ;          THE
1925  B0        DB    $B0
1926  3A        DB    $3A    ;          INSTRUCTOR
1927  FC        DB    $FC    ;          FOR_HELP
1928  5F        DB    $5F
1929  FC        DB    $FC    ;Msg# 13, CLOSE
192A  23        DB    $23
192B  0E        DB    $E     ;          BUT
192C  0A        DB    $A     ;          BLOW2
192D  FC        DB    $FC    ;          HARDER
192E  6F        DB    $6F
192F  FC        DB    $FC    ;Msg# 14, EXCELLENT
1930  41        DB    $41
1931  FC        DB    $FC    ;Msg# 15, PERFECT
1932  A3        DB    $A3
1933  F9        DB    $F9    ;          NOW
1934  6C        DB    $6C
1935  FA        DB    $FA    ;          TRY_GIVING
1936  B9        DB    $B9
```

```
1937 C8            DB      $C8     ;       TWO
1938 8E            DB      $8E     ;       SLOW
1939 08            DB      $8      ;       BREATH
193A FD            DB      $FD     ;       S
193B 89            DB      $89
193C 67            DB      $67     ;Msg# 16, GOOD
193D F9            DB      $F9     ;       BUT
193E 0E            DB      $E
193F 25            DB      $25     ;       BLOW_LESS
1940 FC            DB      $FC     ;       FORCEFULLY
1941 57            DB      $57
1942 F8            DB      $F8     ;Msg# 17, BLOW2
1943 0A            DB      $A
1944 44            DB      $44     ;       INTO
1945 A9            DB      $A9     ;       THE_MANIKINS
1946 FB            DB      $FB     ;       MOUTH
1947 46            DB      $46
1948 D7            DB      $D7     ;       TWICE
1949 D5            DB      $D5     ;       WITH1
194A 1A            DB      $1A     ;       COMPLETE
194B 7E            DB      $7E     ;       RE
194C F8            DB      $F8     ;       FILLING_OF_YOUR_LUNG
194D 4B            DB      $4B
194E FA            DB      $FA     ;       S
194F 89            DB      $89
1950 FA            DB      $FA     ;       AFTER_EACH
1951 09            DB      $9
1952 FB            DB      $FB     ;       BREATH
1953 08            DB      $8
1954 60            DB      $60     ;Msg# 18, MORE!
1955 5C            DB      $5C     ;Msg# 19, MORE
1956 30            DB      $30     ;Msg# 20, GREAT
1957 54            DB      $54     ;Msg# 21, LESS
1958 58            DB      $58     ;Msg# 22, LESS!
1959 B9            DB      $B9     ;Msg# 23, TRY_GIVING
195A C8            DB      $C8     ;       TWO
195B 08            DB      $8      ;       BREATH
195C 89            DB      $89     ;       S
195D 03            DB      $3      ;       AGAIN
195E FC            DB      $FC     ;Msg# 24, !
195F 02            DB      $2
1960 41            DB      $41     ;       EXCELLENT
1961 FC            DB      $FC     ;       VENTILATION
1962 DB            DB      $DB
1963 38            DB      $38     ;       IF
1964 D0            DB      $D0     ;       YOU1
1965 1C            DB      $1C     ;       FEEL
1966 FC            DB      $FC     ;       CONFIDENT
1967 2B            DB      $2B
1968 F9            DB      $F9     ;       PRACTICE
1969 72            DB      $72
196A F8            DB      $F8     ;       CHECK
196B 31            DB      $31
196C F9            DB      $F9     ;       ING
196D 40            DB      $40
196E FA            DB      $FA     ;       THE
196F B0            DB      $B0
1970 2D            DB      $2D     ;       CAROTID
1971 FC            DB      $FC     ;       PULSE
1972 AB            DB      $AB
1973 FC            DB      $FC     ;       !
1974 02            DB      $2
1975 38            DB      $38     ;       IF
1976 D0            DB      $D0     ;       YOU1
1977 FC            DB      $FC     ;       DONT
1978 3B            DB      $3B
1979 FC            DB      $FC     ;       !
197A 02            DB      $2
197B FA            DB      $FA     ;       TRY_GIVING
197C B9            DB      $B9
197D C8            DB      $C8     ;       TWO
197E 08            DB      $8      ;       BREATH
```

```
197F FB              DB      $FB     ;           S
1980 89              DB      $89
1981 03              DB      $3      ;           AGAIN
1982 2D              DB      $2D     ;Msg# 25,   CAROTID
1983 FD              DB      $FD     ;           PULSE
1984 AB              DB      $AB
1985 A6              DB      $A6     ;           THE3
1986 2D              DB      $2D     ;           CAROTID
1987 F9              DB      $F9     ;           PULSE
1988 AB              DB      $AB
1989 F9              DB      $F9     ;           IS
198A 48              DB      $48
198B 59              DB      $59     ;           LOCATED_ON_EITHER
198C 91              DB      $91     ;           SIDE_OF
198D FD              DB      $FD     ;           THE_ADAMS_APPLE
198E C7              DB      $C7
198F 32              DB      $32     ;Msg# 26,   GENTLY
1990 FA              DB      $FA     ;           TRY_TO
1991 BD              DB      $BD
1992 98              DB      $98     ;           SENSE
1993 FA              DB      $FA     ;           IT
1994 83              DB      $83
1995 DD              DB      $DD     ;           WITH_THE
1996 3C              DB      $3C     ;           INDEX_AND_MIDDLE
1997 24              DB      $24     ;           FINGER1
1998 89              DB      $89     ;           S
1999 74              DB      $74     ;           OF
199A 69              DB      $69     ;           ONE2
199B FD              DB      $FD     ;           HAND
199C 6B              DB      $6B
199D 5D              DB      $5D     ;Msg# 27,   MAINTAIN_THE_HEAD
199E B6              DB      $B6     ;           TILT2
199F DD              DB      $DD     ;           WITH_THE
19A0 8C              DB      $8C     ;           PALM
19A1 74              DB      $74     ;           OF
19A2 E5              DB      $E5     ;           YOUR_OTHER
19A3 FF              DB      $FF     ;           HAND
19A4 6B              DB      $6B
19A5 FA              DB      $FA     ;Msg# 28,   IF_YOU_HAVE_DIFFICULTY
19A6 4D              DB      $4D
19A7 F8              DB      $F8     ;           CHECK
19A8 31              DB      $31
19A9 40              DB      $40     ;           ING
19AA FC              DB      $FC     ;           IT
19AB 83              DB      $83
19AC FB              DB      $FB     ;           PLEASE_ASK
19AD 71              DB      $71
19AE F9              DB      $F9     ;           THE3
19AF A6              DB      $A6
19B0 3A              DB      $3A     ;           INSTRUCTOR
19B1 FF              DB      $FF     ;           FOR_HELP
19B2 5F              DB      $5F
                ;   M Table
19B3 F8         M    DB      $F8     ;Msg# 29,   !
19B4 02              DB      $2
19B5 FA              DB      $FA     ;           HAND1
19B6 34              DB      $34
19B7 FD              DB      $FD     ;           POSITION
19B8 A7              DB      $A7
19B9 FA              DB      $FA     ;           FEEL
19BA 1C              DB      $1C
19BB F8              DB      $F8     ;           FOR_THE_BORDER_OF
19BC 63              DB      $63
19BD A9              DB      $A9     ;           THE_MANIKINS
19BE 94              DB      $94     ;           RIB
19BF FC              DB      $FC     ;           S
19C0 89              DB      $89
19C1 DD              DB      $DD     ;           WITH_THE
19C2 3C              DB      $3C     ;           INDEX_AND_MIDDLE
19C3 24              DB      $24     ;           FINGER1
19C4 FB              DB      $FB     ;           S
19C5 89              DB      $89
```

| | | | | |
|---|---|---|---|---|
| 19C6 65 | DB | $65 | ; | OF_THE |
| 19C7 FB | DB | $FB | ; | HAND1 |
| 19C8 34 | DB | $34 | | |
| 19C9 FB | DB | $FB | ; | CLOSEST |
| 19CA 10 | DB | $10 | | |
| 19CB F8 | DB | $F8 | ; | TO |
| 19CC CF | DB | $CF | | |
| 19CD F8 | DB | $F8 | ; | THE_MANIKINS |
| 19CE A9 | DB | $A9 | | |
| 19CF FE | DB | $FE | ; | WAIST |
| 19D0 CA | DB | $CA | | |
| 19D1 64 | DB | $64 | ;Msg# 30, | MOVE_THEM_UPWARD |
| 19D2 FC | DB | $FC | ; | ALONG_THE_RIBCAGE |
| 19D3 0D | DB | $D | | |
| 19D4 C5 | DB | $C5 | ; | UNTIL_YOU_REACH |
| 19D5 F9 | DB | $F9 | ; | THE_RIBCAGE |
| 19D6 86 | DB | $86 | | |
| 19D7 FE | DB | $FE | ; | NOTCH |
| 19D8 97 | DB | $97 | | |
| 19D9 F9 | DB | $F9 | ;Msg# 31, | PLACE |
| 19DA 6E | DB | $6E | | |
| 19DB B4 | DB | $B4 | ; | THE_HEEL_OF |
| 19DC F8 | DB | $F8 | ; | YOUR_OTHER |
| 19DD E5 | DB | $E5 | | |
| 19DE FC | DB | $FC | ; | HAND1 |
| 19DF 34 | DB | $34 | | |
| 19E0 FA | DB | $FA | ; | JUST |
| 19E1 50 | DB | $50 | | |
| 19E2 FA | DB | $FA | ; | ABOVE_THE_TWO |
| 19E3 05 | DB | $5 | | |
| 19E4 28 | DB | $28 | ; | FINGER2 |
| 19E5 FD | DB | $FD | ; | S |
| 19E6 89 | DB | $89 | | |
| 19E7 A1 | DB | $A1 | ; | THEN |
| 19E8 6E | DB | $6E | ; | PLACE |
| 19E9 A6 | DB | $A6 | ; | THE3 |
| 19EA FA | DB | $FA | ; | FIRST |
| 19EB 2C | DB | $2C | | |
| 19EC F9 | DB | $F9 | ; | HAND1 |
| 19ED 34 | DB | $34 | | |
| 19EE FD | DB | $FD | ; | ON_TOP_OF_IT |
| 19EF 9F | DB | $9F | | |
| 19F0 51 | DB | $51 | ;Msg# 32, | KEEP |
| 19F1 F9 | DB | $F9 | ; | YOUR |
| 19F2 D8 | DB | $D8 | | |
| 19F3 28 | DB | $28 | ; | FINGER2 |
| 19F4 89 | DB | $89 | ; | S |
| 19F5 56 | DB | $56 | ; | OFF |
| 19F6 F8 | DB | $F8 | ; | THE_MANIKINS |
| 19F7 A9 | DB | $A9 | | |
| 19F8 94 | DB | $94 | ; | RIB |
| 19F9 FD | DB | $FD | ; | S |
| 19FA 89 | DB | $89 | | |
| 19FB 7D | DB | $7D | ;Msg# 33, | PUSH |
| 19FC FC | DB | $FC | ; | DOWN |
| 19FD 3F | DB | $3F | | |
| 19FE 4C | DB | $4C | ; | I_WILL |
| 19FF 31 | DB | $31 | ; | CHECK |
| 1A00 D8 | DB | $D8 | ; | YOUR |
| 1A01 FA | DB | $FA | ; | HAND1 |
| 1A02 34 | DB | $34 | | |
| 1A03 F8 | DB | $F8 | ; | POSITION |
| 1A04 A7 | DB | $A7 | | |
| 1A05 FD | DB | $FD | ;Msg# 34, | FINE |
| 1A06 4F | DB | $4F | | |
| 1A07 81 | DB | $81 | ; | REMOVE_AND |
| 1A08 90 | DB | $90 | ; | RESET_YOUR |
| 1A09 34 | DB | $34 | ; | HAND1 |
| 1A0A FC | DB | $FC | ; | S |
| 1A0B 89 | DB | $89 | | |
| 1A0C FC | DB | $FC | ; | ! |
| 1A0D 02 | DB | $2 | | |
| 1A0E C4 | DB | $C4 | ; | TRY_IT |

```
1A0F F8      DB    $F8    ;           AGAIN
1A10 03      DB    $3
1A11 FC      DB    $FC    ;Msg# 35,   GOOD
1A12 67      DB    $67
1A13 38      DB    $38    ;           IF
1A14 D0      DB    $D0    ;           YOU1
1A15 1C      DB    $1C    ;           FEEL
1A16 FC      DB    $FC    ;           CONFIDENT
1A17 2B      DB    $2B
1A18 D4      DB    $D4    ;           YOU2
1A19 A0      DB    $A0    ;           SHOULD
1A1A 6C      DB    $6C    ;           NOW
1A1B FB      DB    $FB    ;           PRACTICE
1A1C 72      DB    $72
1A1D 01      DB    $1     ;           A
1A1E FA      DB    $FA    ;           SINGLE
1A1F 95      DB    $95
1A20 F9      DB    $F9    ;           CHEST
1A21 0C      DB    $C
1A22 FC      DB    $FC    ;           COMPRESSION
1A23 14      DB    $14
1A24 FC      DB    $FC    ;           !
1A25 02      DB    $2
1A26 38      DB    $38    ;           IF
1A27 D0      DB    $D0    ;           YOU1
1A28 FC      DB    $FC    ;           DONT
1A29 3B      DB    $3B
1A2A FC      DB    $FC    ;           !
1A2B 02      DB    $2
1A2C C4      DB    $C4    ;           TRY_IT
1A2D F8      DB    $F8    ;           AGAIN
1A2E 03      DB    $3
1A2F D8      DB    $D8    ;Msg# 36,   YOUR
1A30 34      DB    $34    ;           HAND1
1A31 F9      DB    $F9    ;           POSITION
1A32 A7      DB    $A7
1A33 F9      DB    $F9    ;           IS
1A34 48      DB    $48
1A35 4E      DB    $4E    ;           NOT
1A36 7A      DB    $7A    ;           QUITE
1A37 FC      DB    $FC    ;           RIGHT
1A38 B3      DB    $B3
1A39 F9      DB    $F9    ;Msg# 37,   TOO
1A3A BE      DB    $BE
1A3B FC      DB    $FC    ;           HIGH
1A3C 77      DB    $77
1A3D F9      DB    $F9    ;Msg# 38,   TOO
1A3E BE      DB    $BE
1A3F FC      DB    $FC    ;           LOW
1A40 87      DB    $87
1A41 56      DB    $56    ;Msg# 39,   OFF
1A42 FC      DB    $FC    ;           CENTER
1A43 1B      DB    $1B
1A44 82      DB    $82    ;Msg# 40,   RELEASE
1A45 FC      DB    $FC    ;           COMPRESSION
1A46 14      DB    $14
1A47 FC      DB    $FC    ;           !
1A48 02      DB    $2
1A49 C4      DB    $C4    ;           TRY_IT
1A4A FC      DB    $FC    ;           AGAIN
1A4B 03      DB    $3
1A4C FC      DB    $FC    ;           !
1A4D 02      DB    $2
1A4E 95      DB    $95    ;Msg# 41,   SINGLE
1A4F 0C      DB    $C     ;           CHEST
1A50 FD      DB    $FD    ;           COMPRESSION
1A51 14      DB    $14
1A52 96      DB    $96    ;           TAKE
1A53 A6      DB    $A6    ;           THE3
1A54 FA      DB    $FA    ;           CORRECT
1A55 2F      DB    $2F
1A56 F9      DB    $F9    ;           HAND1
1A57 34      DB    $34
```

```
1A58 FC       DB    $FC    ;           POSITION
1A59 A7       DB    $A7
1A5A D8       DB    $D8    ;           YOUR
1A5B 2A       DB    $2A    ;           ELBOWS_LOCKED
1A5C 00       DB    $0     ;           AND_YOUR_SHOULDER
1A5D 89       DB    $89    ;           S
1A5E 22       DB    $22    ;           DIRECTLY_OVER_THE
1A5F FE       DB    $FE    ;           STERNUM
1A60 BF       DB    $BF
1A61 A6       DB    $A6    ;Msg# 42,   THE3
1A62 35       DB    $35    ;           CHEST_SHOULD_BE
1A63 1E       DB    $1E    ;           COMPRESSED
1A64 BB       DB    $BB    ;           SMOOTHLY
1A65 5A       DB    $5A    ;           ONE_AND_ONE_HALF
1A66 FA       DB    $FA    ;           TO
1A67 CF       DB    $CF
1A68 FA       DB    $FA    ;           TWO
1A69 C8       DB    $C8
1A6A FC       DB    $FC    ;           INCHES
1A6B 7B       DB    $7B
1A6C FC       DB    $FC    ;           !
1A6D 02       DB    $2
1A6E C2       DB    $C2    ;           TRY_A
1A6F 95       DB    $95    ;           SINGLE
1A70 0C       DB    $C     ;           CHEST
1A71 FC       DB    $FC    ;           COMPRESSION
1A72 14       DB    $14
1A73 F9       DB    $F9    ;Msg# 43,   TOO
1A74 BE       DB    $BE
1A75 FC       DB    $FC    ;           SHALLOW
1A76 B7       DB    $B7
1A77 F9       DB    $F9    ;Msg# 44,   TOO
1A78 BE       DB    $BE
1A79 FC       DB    $FC    ;           SHALLOW
1A7A B7       DB    $B7
1A7B FC       DB    $FC    ;           !
1A7C 02       DB    $2
1A7D 21       DB    $21    ;           BE_SURE_THAT
1A7E E1       DB    $E1    ;           YOURE
1A7F F8       DB    $F8    ;           PRESS1
1A80 75       DB    $75
1A81 FA       DB    $FA    ;           ING
1A82 40       DB    $40
1A83 92       DB    $92    ;           STRAIGHT
1A84 3F       DB    $3F    ;           DOWN
1A85 D8       DB    $D8    ;           YOUR
1A86 2A       DB    $2A    ;           ELBOWS_LOCKED
1A87 00       DB    $0     ;           AND_YOUR_SHOULDER
1A88 89       DB    $89    ;           S
1A89 22       DB    $22    ;           DIRECTLY_OVER_THE
1A8A FC       DB    $FC    ;           STERNUM
1A8B BF       DB    $BF
1A8C 23       DB    $23    ;Msg# 45,   CLOSE
1A8D 0E       DB    $E     ;           BUT
1A8E F9       DB    $F9    ;           TOO
1A8F BE       DB    $BE
1A90 FC       DB    $FC    ;           SHALLOW
1A91 B7       DB    $B7
1A92 23       DB    $23    ;Msg# 46,   CLOSE
1A93 0E       DB    $E     ;           BUT
1A94 FC       DB    $FC    ;           TOO_DEEP
1A95 D3       DB    $D3
1A96 FC       DB    $FC    ;Msg# 47,   TOO_DEEP
1A97 D3       DB    $D3
1A98 FB       DB    $FB    ;Msg# 48,   GREAT
1A99 30       DB    $30
1A9A F9       DB    $F9    ;           NOW
1A9B 6C       DB    $6C
1A9C 72       DB    $72    ;           PRACTICE
1A9D 0C       DB    $C     ;           CHEST
1A9E 14       DB    $14    ;           COMPRESSION
1A9F FC       DB    $FC    ;           RHYTHM
```

```
1AA0 AF            DB      $AF
1AA1 66            DB      $66     ;           OR1
1AA2 C4            DB      $C4     ;           TRY_IT
1AA3 F8            DB      $F8     ;           AGAIN
1AA4 03            DB      $3
                ; N Table
1AA5 0C    · N     DB      $C      ;Msg# 49,   CHEST
1AA6 14            DB      $14     ;           COMPRESSION
1AA7 FD            DB      $FD     ;           RHYTHM
1AA8 AF            DB      $AF
1AA9 36            DB      $36     ;           GIVE
1AAA 20            DB      $20     ;           FIF
1AAB AC            DB      $AC     ;           TEEN
1AAC 0C            DB      $C      ;           CHEST
1AAD 14            DB      $14     ;           COMPRESSION
1AAE FA            DB      $FA     ;           S
1AAF 89            DB      $89
1AB0 FC            DB      $FC     ;           SMOOTHLY
1AB1 BB            DB      $BB
1AB2 70            DB      $70     ;           NO_BOUNCE
1AB3 FB            DB      $FB     ;           ING
1AB4 40            DB      $40
1AB5 C9            DB      $C9     ;           USING_A
1AB6 80            DB      $80     ;           ONE1
1AB7 04            DB      $4      ;           ANND
1AB8 F9            DB      $F9     ;           TWO
1AB9 C8            DB      $C8
1ABA F9            DB      $F9     ;           ANND
1ABB 04            DB      $4
1ABC AD            DB      $AD     ;           THREE
1ABD F9            DB      $F9     ;           ANND
1ABE 04            DB      $4
1ABF FB            DB      $FB     ;           FOUR
1AC0 49            DB      $49
1AC1 FA            DB      $FA     ;           TO
1AC2 CF            DB      $CF
1AC3 20            DB      $20     ;           FIF
1AC4 FA            DB      $FA     ;           TEEN
1AC5 AC            DB      $AC
1AC6 FC            DB      $FC     ;           CADENCE
1AC7 17            DB      $17
1AC8 FC            DB      $FC     ;           !
1AC9 02            DB      $2
1ACA 16            DB      $16     ;           COME_ALL_THE_WAY_UP
1ACB 1D            DB      $1D     ;           BETWEEN
1ACC 14            DB      $14     ;           COMPRESSION
1ACD FC            DB      $FC     ;           S
1ACE 89            DB      $89
1ACF 9C            DB      $9C     ;Msg# 50,   SET_THE
1AD0 17            DB      $17     ;           CADENCE
1AD1 F9            DB      $F9     ;           SWITCH
1AD2 A8            DB      $A8
1AD3 FC            DB      $FC     ;           FOR_A_CADENCE
1AD4 5B            DB      $5B
1AD5 F8            DB      $F8     ;Msg# 51,   ONE_WAS
1AD6 5E            DB      $5E
1AD7 F9            DB      $F9     ;Msg# 52,   TWO
1AD8 C8            DB      $C8
1AD9 F8            DB      $F8     ;           WERE
1ADA D6            DB      $D6
1ADB AD            DB      $AD     ;Msg# 53,   THREE
1ADC F8            DB      $F8     ;           WERE
1ADD D6            DB      $D6
1ADE 49            DB      $49     ;Msg# 54,   FOUR
1ADF F8            DB      $F8     ;           WERE
1AE0 D6            DB      $D6
1AE1 45            DB      $45     ;Msg# 55,   FIVE
1AE2 F8            DB      $F8     ;           WERE
1AE3 D6            DB      $D6
1AE4 99            DB      $99     ;Msg# 56,   SIX
1AE5 F8            DB      $F8     ;           WERE
1AE6 D6            DB      $D6
```

```
1AE7 8D         DB      $8D     ;Msg# 57, SEVEN
1AE8 F8         DB      $F8     ;         WERE
1AE9 D6         DB      $D6
1AEA 39         DB      $39     ;Msg# 58, EIGHT
1AEB F8         DB      $F8     ;         WERE
1AEC D6         DB      $D6
1AED 61         DB      $61     ;Msg# 59, NINE
1AEE F8         DB      $F8     ;         WERE
1AEF D6         DB      $D6
1AF0 9D         DB      $9D     ;Msg# 60, TEN
1AF1 F8         DB      $F8     ;         WERE
1AF2 D6         DB      $D6
1AF3 3D         DB      $3D     ;Msg# 61, ELEVEN
1AF4 F8         DB      $F8     ;         WERE
1AF5 D6         DB      $D6
1AF6 C1         DB      $C1     ;Msg# 62, TWELVE
1AF7 F8         DB      $F8     ;         WERE
1AF8 D6         DB      $D6
1AF9 B8         DB      $B8     ;Msg# 63, THIR
1AFA F9         DB      $F9     ;         TEEN
1AFB AC         DB      $AC
1AFC F8         DB      $F8     ;         WERE
1AFD D6         DB      $D6
1AFE 49         DB      $49     ;Msg# 64, FOUR
1AFF F9         DB      $F9     ;         TEEN
1B00 AC         DB      $AC
1B01 F8         DB      $F8     ;         WERE
1B02 D6         DB      $D6
1B03 20         DB      $20     ;Msg# 65, FIF
1B04 AC         DB      $AC     ;         TEEN
1B05 F8         DB      $F8     ;         WERE
1B06 D6         DB      $D6
1B07 85         DB      $85     ;Msg# 66, RHYTHM_IS
1B08 B1         DB      $B1     ;         TOO_FAST
1B09 FA         DB      $FA     ;         AND
1B0A 11         DB      $11
1B0B FC         DB      $FC     ;         IRREGULAR
1B0C 7F         DB      $7F
1B0D 85         DB      $85     ;Msg# 67, RHYTHM_IS
1B0E FC         DB      $FC     ;         TOO_FAST
1B0F B1         DB      $B1
1B10 85         DB      $85     ;Msg# 68, RHYTHM_IS
1B11 B5         DB      $B5     ;         TOO_SLOW
1B12 FA         DB      $FA     ;         AND
1B13 11         DB      $11
1B14 FC         DB      $FC     ;         IRREGULAR
1B15 7F         DB      $7F
1B16 85         DB      $85     ;Msg# 69, RHYTHM_IS
1B17 FC         DB      $FC     ;         TOO_SLOW
1B18 B5         DB      $B5
1B19 85         DB      $85     ;Msg# 70, RHYTHM_IS
1B1A FC         DB      $FC     ;         IRREGULAR
1B1B 7F         DB      $7F
1B1C 41         DB      $41     ;Msg# 71, EXCELLENT
1B1D FC         DB      $FC     ;         RHYTHM
1B1E AF         DB      $AF
1B1F 16         DB      $16     ;Msg# 72, COME_ALL_THE_WAY_UP
1B20 1D         DB      $1D     ;         BETWEEN
1B21 14         DB      $14     ;         COMPRESSION
1B22 FC         DB      $FC     ;         S
1B23 89         DB      $89
1B24 FC         DB      $FC     ;Msg# 73, !
1B25 02         DB      $2
1B26 36         DB      $36     ;         GIVE
1B27 20         DB      $20     ;         FIF
1B28 AC         DB      $AC     ;         TEEN
1B29 0C         DB      $C      ;         CHEST
1B2A 14         DB      $14     ;         COMPRESSION
1B2B FA         DB      $FA     ;         S
1B2C 89         DB      $89
1B2D F8         DB      $F8     ;         AGAIN
1B2E 03         DB      $3
```

```
1B2F  4E        DB      $4E     ;Msg# 74, NOT
1B30  7A        DB      $7A     ;         QUITE
1B31  FC        DB      $FC     ;         RIGHT
1B32  B3        DB      $B3
1B33  FC        DB      $FC     ;         !
1B34  02        DB      $2
1B35  38        DB      $38     ;Msg# 75, IF
1B36  D0        DB      $D0     ;         YOU1
1B37  1C        DB      $1C     ;         FEEL
1B38  FC        DB      $FC     ;         CONFIDENT
1B39  2B        DB      $2B
1B3A  FB        DB      $FB     ;         PRACTICE
1B3B  72        DB      $72
1B3C  FC        DB      $FC     ;         CLEARING_THE_AIRWAY
1B3D  12        DB      $12
1B3E  FC        DB      $FC     ;         !
1B3F  02        DB      $2
1B40  38        DB      $38     ;         IF
1B41  D0        DB      $D0     ;         YOU1
1B42  FC        DB      $FC     ;         DONT
1B43  3B        DB      $3B
1B44  FC        DB      $FC     ;         !
1B45  02        DB      $2
1B46  36        DB      $36     ;         GIVE
1B47  20        DB      $20     ;         FIF
1B48  AC        DB      $AC     ;         TEEN
1B49  0C        DB      $C      ;         CHEST
1B4A  14        DB      $14     ;         COMPRESSION
1B4B  FA        DB      $FA     ;         S
1B4C  89        DB      $89
1B4D  F8        DB      $F8     ;         AGAIN
1B4E  03        DB      $3
1B4F  7E        DB      $7E     ;Msg# 76, RE
1B50  6E        DB      $6E     ;         PLACE
1B51  FD        DB      $FD     ;         BATTERY
1B52  0B        DB      $B
1B53  6C        DB      $6C     ;Msg# 77, NOW
1B54  FB        DB      $FB     ;         PRACTICE
1B55  72        DB      $72
1B56  F9        DB      $F9     ;         THE3
1B57  A6        DB      $A6
1B58  FA        DB      $FA     ;         CORRECT
1B59  2F        DB      $2F
1B5A  34        DB      $34     ;         HAND1
1B5B  FE        DB      $FE     ;         POSITION
1B5C  A7        DB      $A7
1B5D  FD        DB      $FD     ;Msg# 78, CLEARING_THE_AIRWAY
1B5E  12        DB      $12
1B5F  42        DB      $42     ;         KNEEL_ASTRIDE
1B60  FB        DB      $FB     ;         THE_MANIKINS
1B61  A9        DB      $A9
1B62  FE        DB      $FE     ;         THIGHS
1B63  AE        DB      $AE
1B64  F9        DB      $F9     ;Msg# 79, PLACE
1B65  6E        DB      $6E
1B66  B4        DB      $B4     ;         THE_HEEL_OF
1B67  7C        DB      $7C     ;         ONE
1B68  FB        DB      $FB     ;         HAND1
1B69  34        DB      $34
1B6A  8A        DB      $8A     ;         SLIGHTLY_ABOVE
1B6B  FD        DB      $FD     ;         THE_NAVEL
1B6C  AA        DB      $AA
1B6D  6E        DB      $6E     ;         PLACE
1B6E  E5        DB      $E5     ;         YOUR_OTHER
1B6F  34        DB      $34     ;         HAND1
1B70  FE        DB      $FE     ;         ON_TOP_OF_IT
1B71  9F        DB      $9F
1B72  79        DB      $79     ;Msg# 80, PRESS2
1B73  FB        DB      $FB     ;         INTO_THE_ABDOMEN
1B74  3E        DB      $3E
1B75  D9        DB      $D9     ;         WITH3
1B76  76        DB      $76     ;         QUICK
1B77  C6        DB      $C6     ;         UPWARD
```

```
1B78 BC           DB      $BC     ;          THRUST1
1B79 FD           DB      $FD     ;          S
1B7A 89           DB      $89
1B7B 26           DB      $26     ;          EACH
1B7C CB           DB      $CB     ;          THRUST2
1B7D A4           DB      $A4     ;          SHOULD_BE
1B7E 37           DB      $37     ;          DISTINCT
1B7F 06           DB      $6      ;          AND_DELIVERED_WITH
1B80 FA           DB      $FA     ;          THE_INTENT
1B81 A5           DB      $A5
1B82 52           DB      $52     ;          OF1
1B83 FD           DB      $FD     ;          CLEARING_THE_AIRWAY
1B84 12           DB      $12
1B85 43           DB      $43     ;          DO_IT
1B86 FF           DB      $FF     ;          TEN_TIMES
1B87 A2           DB      $A2
1B88 DA           DB      $DA     ;Msg# 81,  WHEN_YOU
1B89 1C           DB      $1C     ;          FEEL
1B8A FC           DB      $FC     ;          CONFIDENT
1B8B 2B           DB      $2B
1B8C FB           DB      $FB     ;          PRACTICE
1B8D 72           DB      $72
1B8E CD           DB      $CD     ;          VENTILATING
1B8F B0           DB      $B0     ;          THE
1B90 FE           DB      $FE     ;          MANIKIN
1B91 8B           DB      $8B
                  ;S word table
1B92 00         S DB      $0      ;AND_YOUR_SHOULDER
1B93 00           DB      $0
1B94 A4           DB      $A4
1B95 85           DB      $85
1B96 92           DB      $92     ;ANND
1B97 DA           DB      $DA
1B98 52           DB      $52
1B99 EE           DB      $EE
1B9A EF           DB      $EF     ;BREATH
1B9B D3           DB      $D3
1B9C 40           DB      $40
1B9D 69           DB      $69
1B9E 31           DB      $31     ;CHEST
1B9F A0           DB      $A0
1BA0 40           DB      $40
1BA1 40           DB      $40
1BA2 A4           DB      $A4     ;CLOSEST
1BA3 AE           DB      $AE
1BA4 41           DB      $41
1BA5 C2           DB      $C2
1BA6 35           DB      $35     ;COMPRESSION
1BA7 E0           DB      $E0
1BA8 80           DB      $80
1BA9 40           DB      $40
1BAA DF           DB      $DF     ;FAST
1BAB 5D           DB      $5D
1BAC 40           DB      $40
1BAD BE           DB      $BE
1BAE 15           DB      $15     ;FEEL
1BAF 90           DB      $90
1BB0 30           DB      $30
1BB1 10           DB      $10
1BB2 84           DB      $84     ;FIF
1BB3 01           DB      $1
1BB4 32           DB      $32
1BB5 40           DB      $40
1BB6 4B           DB      $4B     ;FINGER1
1BB7 4C           DB      $4C
1BB8 43           DB      $43
1BB9 81           DB      $81
1BBA 8E           DB      $8E     ;FINGER2
1BBB C1           DB      $C1
1BBC 53           DB      $53
1BBD 40           DB      $40
1BBE D7           DB      $D7     ;FIRST
1BBF 76           DB      $76
```

```
1BC0  31        DB    $31
1BC1  41        DB    $41
1BC2  B7        DB    $B7        ;GREAT
1BC3  06        DB    $6
1BC4  62        DB    $62
1BC5  C8        DB    $C8
1BC6  51        DB    $51        ;HAND1
1BC7  CD        DB    $CD
1BC8  53        DB    $53
1BC9  01        DB    $1
1BCA  11        DB    $11        ;IF
1BCB  50        DB    $50
1BCC  20        DB    $20
1BCD  40        DB    $40
1BCE  56        DB    $56        ;INDEX_AND_MIDDLE
1BCF  CE        DB    $CE
1BD0  D3        DB    $D3
1BD1  40        DB    $40
1BD2  62        DB    $62        ;ING
1BD3  BC        DB    $BC
1BD4  11        DB    $11
1BD5  FF        DB    $FF
1BD6  75        DB    $75        ;INTO
1BD7  41        DB    $41
1BD8  34        DB    $34
1BD9  20        DB    $20
1BDA  01        DB    $1         ;IS
1BDB  49        DB    $49
1BDC  20        DB    $20
1BDD  88        DB    $88
1BDE  AB        DB    $AB        ;I_WILL
1BDF  B7        DB    $B7
1BE0  40        DB    $40
1BE1  5F        DB    $5F
1BE2  D5        DB    $D5        ;JUST
1BE3  76        DB    $76
1BE4  21        DB    $21
1BE5  00        DB    $0
1BE6  EE        DB    $EE        ;LESS
1BE7  EE        DB    $EE
1BE8  62        DB    $62
1BE9  81        DB    $81
1BEA  E8        DB    $E8        ;LESS!
1BEB  AE        DB    $AE
1BEC  62        DB    $62
1BED  40        DB    $40
1BEE  E3        DB    $E3        ;MORE
1BEF  3E        DB    $3E
1BF0  52        DB    $52
1BF1  70        DB    $70
1BF2  DD        DB    $DD        ;MORE!
1BF3  0E        DB    $E
1BF4  62        DB    $62
1BF5  30        DB    $30
1BF6  B0        DB    $B0        ;MOVE_THEM_UPWARD
1BF7  F0        DB    $F0
1BF8  E1        DB    $E1
1BF9  47        DB    $47
1BFA  37        DB    $37        ;NOSTRIL
1BFB  E1        DB    $E1
1BFC  74        DB    $74
1BFD  C0        DB    $C0
1BFE  25        DB    $25        ;NOW
1BFF  9E        DB    $9E
1C00  40        DB    $40
1C01  C0        DB    $C0
1C02  78        DB    $78        ;NO_BOUNCE
1C03  24        DB    $24
1C04  72        DB    $72
1C05  DC        DB    $DC
1C06  16        DB    $16        ;OF
1C07  53        DB    $53
1C08  22        DB    $22
```

```
1C09 31         DB      $31
1C0A FD         DB      $FD     ;ON
1C0B 77         DB      $77
1C0C 21         DB      $21
1C0D 40         DB      $40
1C0E C2         DB      $C2     ;ONE
1C0F 7B         DB      $7B
1C10 44         DB      $44
1C11 40         DB      $40
1C12 94         DB      $94     ;ONE1
1C13 98         DB      $98
1C14 61         DB      $61
1C15 30         DB      $30
1C16 98         DB      $98     ;OPEN_THE_AIRWAY
1C17 C8         DB      $C8
1C18 F2         DB      $F2
1C19 82         DB      $82
1C1A 22         DB      $22     ;P
1C1B D7         DB      $D7
1C1C 01         DB      $1
1C1D 40         DB      $40
1C1E 12         DB      $12     ;PALM
1C1F 82         DB      $82
1C20 32         DB      $32
1C21 D1         DB      $D1
1C22 47         DB      $47     ;RESET_YOUR
1C23 B7         DB      $B7
1C24 80         DB      $80
1C25 03         DB      $3
1C26 43         DB      $43     ;RIB
1C27 4C         DB      $4C
1C28 53         DB      $53
1C29 00         DB      $0
1C2A FC         DB      $FC     ;SENSE
1C2B 6C         DB      $6C
1C2C 33         DB      $33
1C2D 94         DB      $94
1C2E 94         DB      $94     ;SET_THE
1C2F 01         DB      $1
1C30 43         DB      $43
1C31 80         DB      $80
1C32 22         DB      $22     ;SHOULD
1C33 A0         DB      $A0
1C34 20         DB      $20
1C35 FE         DB      $FE
1C36 57         DB      $57     ;SHOULD_BE
1C37 4B         DB      $4B
1C38 55         DB      $55
1C39 B7         DB      $B7
1C3A 9E         DB      $9E     ;SWITCH
1C3B 99         DB      $99
1C3C 43         DB      $43
1C3D 82         DB      $82
1C3E 87         DB      $87     ;TEEN
1C3F 41         DB      $41
1C40 52         DB      $52
1C41 40         DB      $40
1C42 D6         DB      $D6     ;THE
1C43 D6         DB      $D6
1C44 10         DB      $10
1C45 40         DB      $40
1C46 CE         DB      $CE     ;THE_HEEL_OF
1C47 77         DB      $77
1C48 61         DB      $61
1C49 FF         DB      $FF
1C4A 16         DB      $16     ;THIR
1C4B 5F         DB      $5F
1C4C 23         DB      $23
1C4D 6E         DB      $6E
1C4E 48         DB      $48     ;THRUST1
1C4F D7         DB      $D7
1C50 55         DB      $55
1C51 BE         DB      $BE
```

```
1C52 B2           DB    $B2      ;TILT1
1C53 CA           DB    $CA
1C54 42           DB    $42
1C55 3C           DB    $3C
1C56 65           DB    $65      ;TRY_IT
1C57 EA           DB    $EA
1C58 40           DB    $40
1C59 5F           DB    $5F
1C5A AE           DB    $AE      ;TWO
1C5B 59           DB    $59
1C5C 33           DB    $33
1C5D 80           DB    $80
1C5E 25           DB    $25      ;UNDER_THE
1C5F 43           DB    $43
1C60 62           DB    $62
1C61 42           DB    $42
1C62 13           DB    $13      ;YOU1
1C63 90           DB    $90
1C64 20           DB    $20
1C65 00           DB    $0
1C66 20           DB    $20      ;YOU2
1C67 A0           DB    $A0
1C68 20           DB    $20
1C69 00           DB    $0
1C6A 9A           DB    $9A      ;YOUR
1C6B C8           DB    $C8
1C6C 21           DB    $21
1C6D E7           DB    $E7
                ;T word table
1C6E 30        T  DB    $30      ;A
1C6F 20           DB    $20
1C70 10           DB    $10
1C71 80           DB    $80
1C72 87           DB    $87      ;ABOVE_THE_TWO
1C73 01           DB    $1
1C74 73           DB    $73
1C75 C0           DB    $C0
1C76 4E           DB    $4E      ;AFTER_EACH
1C77 45           DB    $45
1C78 71           DB    $71
1C79 91           DB    $91
1C7A BF           DB    $BF      ;ALONG_THE_RIBCAGE
1C7B 37           DB    $37
1C7C F1           DB    $F1
1C7D 40           DB    $40
1C7E EE           DB    $EE      ;AND
1C7F 93           DB    $93
1C80 10           DB    ,$10
1C81 40           DB    $40
1C82 0E           DB    $E       ;AND_KEEPING_A
1C83 D6           DB    $D6
1C84 91           DB    $91
1C85 00           DB    $0
1C86 23           DB    $23      ;AND_MAKE_A
1C87 17           DB    $17
1C88 51           DB    $51
1C89 7F           DB    $7F
1C8A F6           DB    $F6      ;BETWEEN
1C8B F7           DB    $F7
1C8C 61           DB    $61
1C8D 80           DB    $80
1C8E 6F           DB    $6F      ;BE_SURE_THAT
1C8F 99           DB    $99
1C90 81           DB    $81
1C91 43           DB    $43
1C92 39           DB    $39      ;BLOW_LESS
1C93 C2           DB    $C2
1C94 71           DB    $71
1C95 81           DB    $81
1C96 40           DB    $40      ;BONY_PART
1C97 E7           DB    $E7
1C98 92           DB    $92
```

| | | | |
|---|---|---|---|
| 1C99 41 | DB | $41 | |
| 1C9A 2F | DB | $2F | ;CAROTID |
| 1C9B 82 | DB | $82 | |
| 1C9C 61 | DB | $61 | |
| 1C9D 40 | DB | $40 | |
| 1C9E B0 | DB | $B0 | ;CHECK |
| 1C9F 16 | DB | $16 | |
| 1CA0 30 | DB | $30 | |
| 1CA1 C1 | DB | $C1 | |
| 1CA2 88 | DB | $88 | ;CHEST_SHOULD_BE |
| 1CA3 83 | DB | $83 | |
| 1CA4 A0 | DB | $A0 | |
| 1CA5 0E | DB | $E | |
| 1CA6 A8 | DB | $A8 | ;EIGHT |
| 1CA7 7B | DB | $7B | |
| 1CA8 34 | DB | $34 | |
| 1CA9 C0 | DB | $C0 | |
| 1CAA 0A | DB | $A | ;ELEVEN |
| 1CAB 01 | DB | $1 | |
| 1CAC 63 | DB | $63 | |
| 1CAD D0 | DB | $D0 | |
| 1CAE 03 | DB | $3 | ;EXCELLENT |
| 1CAF D1 | DB | $D1 | |
| 1CB0 60 | DB | $60 | |
| 1CB1 C0 | DB | $C0 | |
| 1CB2 B4 | DB | $B4 | ;FIVE |
| 1CB3 99 | DB | $99 | |
| 1CB4 53 | DB | $53 | |
| 1CB5 00 | DB | $0 | |
| 1CB6 7B | DB | $7B | ;FOUR |
| 1CB7 6E | DB | $6E | |
| 1CB8 43 | DB | $43 | |
| 1CB9 3F | DB | $3F | |
| 1CBA 55 | DB | $55 | ;IF_YOU_HAVE_DIFFICULTY |
| 1CBB D6 | DB | $D6 | |
| 1CBC C1 | DB | $C1 | |
| 1CBD E6 | DB | $E6 | |
| 1CBE E6 | DB | $E6 | ;KEEP |
| 1CBF 37 | DB | $37 | |
| 1CC0 21 | DB | $21 | |
| 1CC1 C0 | DB | $C0 | |
| 1CC2 1B | DB | $1B | ;LIFT |
| 1CC3 C4 | DB | $C4 | |
| 1CC4 42 | DB | $42 | |
| 1CC5 C0 | DB | $C0 | |
| 1CC6 4B | DB | $4B | ;LOCATED_ON_EITHER |
| 1CC7 C1 | DB | $C1 | |
| 1CC8 D4 | DB | $D4 | |
| 1CC9 78 | DB | $78 | |
| 1CCA C4 | DB | $C4 | ;MAINTAIN_THE_HEAD |
| 1CCB 9A | DB | $9A | |
| 1CCC E3 | DB | $E3 | |
| 1CCD 67 | DB | $67 | |
| 1CCE DC | DB | $DC | ;NINE |
| 1CCF 1C | DB | $1C | |
| 1CD0 43 | DB | $43 | |
| 1CD1 80 | DB | $80 | |
| 1CD2 4F | DB | $4F | ;OF_THE |
| 1CD3 CD | DB | $CD | |
| 1CD4 23 | DB | $23 | |
| 1CD5 00 | DB | $0 | |
| 1CD6 18 | DB | $18 | ;ONE2 |
| 1CD7 84 | DB | $84 | |
| 1CD8 32 | DB | $32 | |
| 1CD9 40 | DB | $40 | |
| 1CDA 34 | DB | $34 | ;OR |
| 1CDB 47 | DB | $47 | |
| 1CDC 22 | DB | $22 | |
| 1CDD E0 | DB | $E0 | |
| 1CDE 6F | DB | $6F | ;PLEASE_ASK |
| 1CDF CF | DB | $CF | |
| 1CE0 80 | DB | $80 | |

| | | | |
|---|---|---|---|
| 1CE1 C6 | DB | $C6 | |
| 1CE2 C4 | DB | $C4 | ;PRESS1 |
| 1CE3 F4 | DB | $F4 | |
| 1CE4 30 | DB | $30 | |
| 1CE5 F5 | DB | $F5 | |
| 1CE6 EC | DB | $EC | ;PRESS2 |
| 1CE7 7A | DB | $7A | |
| 1CE8 34 | DB | $34 | |
| 1CE9 BF | DB | $BF | |
| 1CEA 73 | DB | $73 | ;PUSH |
| 1CEB E3 | DB | $E3 | |
| 1CEC 42 | DB | $42 | |
| 1CED 41 | DB | $41 | |
| 1CEE 40 | DB | $40 | ;REMOVE_AND |
| 1CEF 6A | DB | $6A | |
| 1CF0 70 | DB | $70 | |
| 1CF1 4D | DB | $4D | |
| 1CF2 61 | DB | $61 | ;RHYTHM_IS |
| 1CF3 39 | DB | $39 | |
| 1CF4 74 | DB | $74 | |
| 1CF5 60 | DB | $60 | |
| 1CF6 CD | DB | $CD | ;S |
| 1CF7 E1 | DB | $E1 | |
| 1CF8 10 | DB | $10 | |
| 1CF9 FF | DB | $FF | |
| 1CFA BC | DB | $BC | ;SEVEN |
| 1CFB D9 | DB | $D9 | |
| 1CFC 53 | DB | $53 | |
| 1CFD 01 | DB | $1 | |
| 1CFE 59 | DB | $59 | ;SIDE_OF |
| 1CFF 39 | DB | $39 | |
| 1D00 44 | DB | $44 | |
| 1D01 00 | DB | $0 | |
| 1D02 24 | DB | $24 | ;SINGLE |
| 1D03 81 | DB | $81 | |
| 1D04 44 | DB | $44 | |
| 1D05 50 | DB | $50 | |
| 1D06 B9 | DB | $B9 | ;SIX |
| 1D07 99 | DB | $99 | |
| 1D08 33 | DB | $33 | |
| 1D09 40 | DB | $40 | |
| 1D0A 05 | DB | $5 | ;TEN |
| 1D0B C1 | DB | $C1 | |
| 1D0C 43 | DB | $43 | |
| 1D0D 40 | DB | $40 | |
| 1D0E 4F | DB | $4F | ;THEN |
| 1D0F BA | DB | $BA | |
| 1D10 30 | DB | $30 | |
| 1D11 40 | DB | $40 | |
| 1D12 14 | DB | $14 | ;THE_INTENT |
| 1D13 19 | DB | $19 | |
| 1D14 85 | DB | $85 | |
| 1D15 98 | DB | $98 | |
| 1D16 3A | DB | $3A | ;THE_MANIKINS |
| 1D17 CC | DB | $CC | |
| 1D18 83 | DB | $83 | |
| 1D19 80 | DB | $80 | |
| 1D1A B1 | DB | $B1 | ;THREE |
| 1D1B D9 | DB | $D9 | |
| 1D1C 23 | DB | $23 | |
| 1D1D C0 | DB | $C0 | |
| 1D1E 82 | DB | $82 | ;TOO_FAST |
| 1D1F B0 | DB | $B0 | |
| 1D20 84 | DB | $84 | |
| 1D21 4F | DB | $4F | |
| 1D22 8A | DB | $8A | ;TOO_SLOW |
| 1D23 FF | DB | $FF | |
| 1D24 74 | DB | $74 | |
| 1D25 B0 | DB | $B0 | |
| 1D26 78 | DB | $78 | ;TRY_GIVING |
| 1D27 61 | DB | $61 | |
| 1D28 74 | DB | $74 | |

```
1D29 9F            DB      $9F
1D2A F7            DB      $F7     ;TRY_TO
1D2B 04            DB      $4
1D2C 53            DB      $53
1D2D 68            DB      $68
1D2E 10            DB      $10     ;TWELVE
1D2F D1            DB      $D1
1D30 53            DB      $53
1D31 8E            DB      $8E
1D32 64            DB      $64     ;UNTIL_YOU_REACH
1D33 0E            DB      $E
1D34 A3            DB      $A3
1D35 8F            DB      $8F
1D36 8C            DB      $8C     ;USING_A
1D37 81            DB      $81
1D38 62            DB      $62
1D39 59            DB      $59
1D3A CF            DB      $CF     ;VENTILATING
1D3B E0            DB      $E0
1D3C 60            DB      $60
1D3D F6            DB      $F6
1D3E 00            DB      $0      ;WITH
1D3F 00            DB      $0
1D40 21            DB      $21
1D41 E7            DB      $E7
1D42 E0            DB      $E0     ;WITH1
1D43 9C            DB      $9C
1D44 23            DB      $23
1D45 E8            DB      $E8
1D46 FC            DB      $FC     ;WITH3
1D47 38            DB      $38
1D48 24            DB      $24
1D49 FF            DB      $FF
1D4A 48            DB      $48     ;WITH_THE
1D4B 4C            DB      $4C
1D4C 33            DB      $33
1D4D 00            DB      $0
1D4E 7B            DB      $7B     ;YOURE
1D4F DD            DB      $DD
1D50 31            DB      $31
1D51 C0            DB      $C0
1D52 80            DB      $80     ;YOUR_OTHER
1D53 00            DB      $0
1D54 73            DB      $73
1D55 01            DB      $1
                ;U word table
1D56 30         U   DB      $30     ;!
1D57 E8            DB      $E8
1D58 03            DB      $3
1D59 04            DB      $4
1D5A 0A            DB      $A      ;AND_DELIVERED_WITH
1D5B 01            DB      $1
1D5C A5            DB      $A5
1D5D 18            DB      $18
1D5E 71            DB      $71     ;BLOW2
1D5F 39            DB      $39
1D60 44            DB      $44
1D61 08            DB      $8
1D62 2D            DB      $2D     ;BUT
1D63 3B            DB      $3B
1D64 21            DB      $21
1D65 47            DB      $47
1D66 1C            DB      $1C     ;CLEARING_THE_AIRWAY
1D67 B1            DB      $B1
1D68 D5            DB      $D5
1D69 C0            DB      $C0
1D6A E8            DB      $E8     ;COME_ALL_THE_WAY_UP
1D6B F7            DB      $F7
1D6C E1            DB      $E1
1D6D 00            DB      $0
1D6E 48            DB      $48     ;COMPLETE
1D6F A4            DB      $A4
```

| | | | |
|---|---|---|---|
| 1D70 51 | DB | $51 | |
| 1D71 A1 | DB | $A1 | |
| 1D72 78 | DB | $78 | ;COMPRESSED |
| 1D73 95 | DB | $95 | |
| 1D74 70 | DB | $70 | |
| 1D75 00 | DB | $0 | |
| 1D76 0A | DB | $A | ;DIRECTLY_OVER_THE |
| 1D77 85 | DB | $85 | |
| 1D78 B4 | DB | $B4 | |
| 1D79 58 | DB | $58 | |
| 1D7A 4E | DB | $4E | ;EACH |
| 1D7B 95 | DB | $95 | |
| 1D7C 45 | DB | $45 | |
| 1D7D 17 | DB | $17 | |
| 1D7E 62 | DB | $62 | ;ELBOWS_LOCKED |
| 1D7F 24 | DB | $24 | |
| 1D80 D2 | DB | $D2 | |
| 1D81 00 | DB | $0 | |
| 1D82 0C | DB | $C | ;FOREHEAD |
| 1D83 C1 | DB | $C1 | |
| 1D84 52 | DB | $52 | |
| 1D85 C1 | DB | $C1 | |
| 1D86 AC | DB | $AC | ;GENTLY |
| 1D87 06 | DB | $6 | |
| 1D88 62 | DB | $62 | |
| 1D89 C4 | DB | $C4 | |
| 1D8A 80 | DB | $80 | ;GIVE |
| 1D8B 00 | DB | $0 | |
| 1D8C 42 | DB | $42 | |
| 1D8D 01 | DB | $1 | |
| 1D8E 80 | DB | $80 | ;INSTRUCTOR |
| 1D8F 00 | DB | $0 | |
| 1D90 80 | DB | $80 | |
| 1D91 83 | DB | $83 | |
| 1D92 F0 | DB | $F0 | ;INTO_THE_ABDOMEN |
| 1D93 39 | DB | $39 | |
| 1D94 B4 | DB | $B4 | |
| 1D95 FF | DB | $FF | |
| 1D96 AC | DB | $AC | ;KNEEL_ASTRIDE |
| 1D97 3B | DB | $3B | |
| 1D98 D4 | DB | $D4 | |
| 1D99 80 | DB | $80 | |
| 1D9A 28 | DB | $28 | ;MOUTH |
| 1D9B 96 | DB | $96 | |
| 1D9C 41 | DB | $41 | |
| 1D9D A5 | DB | $A5 | |
| 1D9E 30 | DB | $30 | ;NEAR_THE |
| 1D9F 06 | DB | $6 | |
| 1DA0 42 | DB | $42 | |
| 1DA1 41 | DB | $41 | |
| 1DA2 B3 | DB | $B3 | ;NOT |
| 1DA3 D7 | DB | $D7 | |
| 1DA4 30 | DB | $30 | |
| 1DA5 40 | DB | $40 | |
| 1DA6 5D | DB | $5D | ;OF1 |
| 1DA7 01 | DB | $1 | |
| 1DA8 15 | DB | $15 | |
| 1DA9 80 | DB | $80 | |
| 1DAA 9F | DB | $9F | ;OFF |
| 1DAB E6 | DB | $E6 | |
| 1DAC 44 | DB | $44 | |
| 1DAD 7F | DB | $7F | |
| 1DAE 99 | DB | $99 | ;ONE_AND_ONE_HALF |
| 1DAF 0B | DB | $B | |
| 1DB0 C0 | DB | $C0 | |
| 1DB1 98 | DB | $98 | |
| 1DB2 F5 | DB | $F5 | ;ONE_WAS |
| 1DB3 6F | DB | $6F | |
| 1DB4 A2 | DB | $A2 | |
| 1DB5 80 | DB | $80 | |
| 1DB6 17 | DB | $17 | ;OPEN_YOUR_MOUTH |
| 1DB7 D6 | DB | $D6 | |

```
1DB8 91        DB      $91
1DB9 41        DB      $41
1DBA 80        DB      $80     ;OR1
1DBB 00        DB      $0
1DBC 24        DB      $24
1DBD B0        DB      $B0
1DBE 31        DB      $31     ;PINCH_OFF
1DBF 21        DB      $21
1DC0 64        DB      $64
1DC1 C0        DB      $C0
1DC2 66        DB      $66     ;PLACE
1DC3 19        DB      $19
1DC4 31        DB      $31
1DC5 C0        DB      $C0
1DC6 2A        DB      $2A     ;PRACTICE
1DC7 5E        DB      $5E
1DC8 50        DB      $50
1DC9 C2        DB      $C2
1DCA 40        DB      $40     ;QUICK
1DCB 00        DB      $0
1DCC 35        DB      $35
1DCD 80        DB      $80
1DCE B7        DB      $B7     ;QUITE
1DCF 17        DB      $17
1DD0 30        DB      $30
1DD1 C0        DB      $C0
1DD2 85        DB      $85     ;RE
1DD3 31        DB      $31
1DD4 21        DB      $21
1DD5 FF        DB      $FF
1DD6 BE        DB      $BE     ;RELEASE
1DD7 F7        DB      $F7
1DD8 50        DB      $50
1DD9 FD        DB      $FD
1DDA C4        DB      $C4     ;THE_RIBCAGE
1DDB 00        DB      $0
1DDC A1        DB      $A1
1DDD 77        DB      $77
1DDE C6        DB      $C6     ;SLIGHTLY_ABOVE
1DDF BA        DB      $BA
1DE0 B4        DB      $B4
1DE1 01        DB      $1
1DE2 8C        DB      $8C     ;SLOW
1DE3 C0        DB      $C0
1DE4 54        DB      $54
1DE5 EF        DB      $EF
1DE6 77        DB      $77     ;STRAIGHT
1DE7 DC        DB      $DC
1DE8 41        DB      $41
1DE9 01        DB      $1
1DEA 5A        DB      $5A     ;TAKE
1DEB 9A        DB      $9A
1DEC 32        DB      $32
1DED 0A        DB      $A
1DEE FC        DB      $FC     ;TAKE_A
1DEF 3B        DB      $3B
1DF0 30        DB      $30
1DF1 C5        DB      $C5
1DF2 80        DB      $80     ;TAKING_A
1DF3 00        DB      $0
1DF4 51        DB      $51
1DF5 31        DB      $31
1DF6 2E        DB      $2E     ;TEN_TIMES
1DF7 51        DB      $51
1DF8 D5        DB      $D5
1DF9 00        DB      $0
1DFA 00        DB      $0      ;THE3
1DFB 00        DB      $0
1DFC 10        DB      $10
1DFD 49        DB      $49
1DFE E5        DB      $E5     ;THE_NAVEL
1DFF 7B        DB      $7B
```

```
1E00 64          DB      $64
1E01 FF          DB      $FF
1E02 B9          DB      $B9     ;THIGHS
1E03 BB          DB      $BB
1E04 84          DB      $84
1E05 C0          DB      $C0
1E06 F4          DB      $F4     ;TIGHT_SEAL
1E07 3C          DB      $3C
1E08 70          DB      $70
1E09 FF          DB      $FF
1E0A D3          DB      $D3     ;TILT2
1E0B 80          DB      $80
1E0C 23          DB      $23
1E0D 9C          DB      $9C
1E0E A5          DB      $A5     ;TO1
1E0F A3          DB      $A3
1E10 00          DB      $0
1E11 93          DB      $93
1E12 52          DB      $52     ;TOO
1E13 FA          DB      $FA
1E14 20          DB      $20
1E15 50          DB      $50
1E16 20          DB      $20     ;TRY_A
1E17 01          DB      $1
1E18 44          DB      $44
1E19 80          DB      $80
1E1A 43          DB      $43     ;UPWARD
1E1B 80          DB      $80
1E1C 55          DB      $55
1E1D 57          DB      $57
1E1E A9          DB      $A9     ;WAIST
1E1F 70          DB      $70
1E20 71          DB      $71
1E21 80          DB      $80
1E22 04          DB      $4      ;WAY_BACK
1E23 C1          DB      $C1
1E24 82          DB      $82
1E25 00          DB      $0
1E26 20          DB      $20     ;WEL
1E27 1C          DB      $1C
1E28 33          DB      $33
1E29 18          DB      $18
1E2A 00          DB      $0      ;WERE
1E2B 00          DB      $0
1E2C 53          DB      $53
1E2D C1          DB      $C1
1E2E 3B          DB      $3B     ;WHEN_YOU
1E2F 51          DB      $51
1E30 45          DB      $45
1E31 30          DB      $30
                 ;V word table
1E32 6A        V DB      $6A     ;AGAIN
1E33 49          DB      $49
1E34 50          DB      $50
1E35 86          DB      $86
1E36 E3          DB      $E3     ;BASE_OF_THE_HEAD
1E37 84          DB      $84
1E38 B3          DB      $B3
1E39 C0          DB      $C0
1E3A 69          DB      $69     ;BATTERY
1E3B D9          DB      $D9
1E3C 51          DB      $51
1E3D C0          DB      $C0
1E3E 02          DB      $2      ;BLOW1
1E3F E7          DB      $E7
1E40 41          DB      $41
1E41 C0          DB      $C0
1E42 A8          DB      $A8     ;BY
1E43 4A          DB      $4A
1E44 32          DB      $32
1E45 BC          DB      $BC
1E46 98          DB      $98     ;CADENCE
1E47 81          DB      $81
```

```
1E48 63        DB      $63
1E49 18        DB      $18
1E4A A4        DB      $A4     ;CENTER
1E4B 65        DB      $65
1E4C 44        DB      $44
1E4D 17        DB      $17
1E4E 4A        DB      $4A     ;CHIN
1E4F 28        DB      $28
1E50 62        DB      $62
1E51 32        DB      $32
1E52 5F        DB      $5F     ;CLOSE
1E53 89        DB      $89
1E54 60        DB      $60
1E55 61        DB      $61
1E56 23        DB      $23     ;COME_TO_COACH_ANDY
1E57 34        DB      $34
1E58 D3        DB      $D3
1E59 B8        DB      $B8
1E5A 18        DB      $18     ;CONFIDENT
1E5B A0        DB      $A0
1E5C 80        DB      $80
1E5D 00        DB      $0
1E5E 5D        DB      $5D     ;CORRECT
1E5F A4        DB      $A4
1E60 42        DB      $42
1E61 80        DB      $80
1E62 21        DB      $21     ;DEEP
1E63 17        DB      $17
1E64 11        DB      $11
1E65 C0        DB      $C0
1E66 00        DB      $0      ;DISTINCT
1E67 00        DB      $0
1E68 A5        DB      $A5
1E69 01        DB      $1
1E6A 3E        DB      $3E     ;DONT
1E6B 20        DB      $20
1E6C 20        DB      $20
1E6D 4A        DB      $4A
1E6E 15        DB      $15     ;DOWN
1E6F DD        DB      $DD
1E70 74        DB      $74
1E71 40        DB      $40
1E72 2A        DB      $2A     ;DO_IT
1E73 71        DB      $71
1E74 35        DB      $35
1E75 E0        DB      $E0
1E76 20        DB      $20     ;EITHER
1E77 84        DB      $84
1E78 42        DB      $42
1E79 BF        DB      $BF
1E7A 88        DB      $88     ;FILLING_OF_YOUR_LUNG
1E7B 30        DB      $30
1E7C C1        DB      $C1
1E7D 68        DB      $68
1E7E C3        DB      $C3     ;FINE
1E7F 4E        DB      $4E
1E80 62        DB      $62
1E81 40        DB      $40
1E82 37        DB      $37     ;FINGERTIPS
1E83 27        DB      $27
1E84 92        DB      $92
1E85 C0        DB      $C0
1E86 41        DB      $41     ;FORCEFULLY
1E87 43        DB      $43
1E88 71        DB      $71
1E89 61        DB      $61
1E8A A3        DB      $A3     ;FOR_A_CADENCE
1E8B 1B        DB      $1B
1E8C B3        DB      $B3
1E8D 3E        DB      $3E
1E8E 18        DB      $18     ;FOR_HELP
1E8F CD        DB      $CD
1E90 73        DB      $73
```

| | | | |
|---|---|---|---|
| 1E91 4F | DB | $4F | |
| 1E92 30 | DB | $30 | ;FOR_THE_BORDER_OF |
| 1E93 EC | DB | $EC | |
| 1E94 93 | DB | $93 | |
| 1E95 E0 | DB | $E0 | |
| 1E96 BD | DB | $BD | ;GOOD |
| 1E97 CE | DB | $CE | |
| 1E98 52 | DB | $52 | |
| 1E99 80 | DB | $80 | |
| 1E9A D6 | DB | $D6 | ;HAND |
| 1E9B 1C | DB | $1C | |
| 1E9C 63 | DB | $63 | |
| 1E9D 00 | DB | $0 | |
| 1E9E 50 | DB | $50 | ;HARDER |
| 1E9F 5A | DB | $5A | |
| 1EA0 42 | DB | $42 | |
| 1EA1 C0 | DB | $C0 | |
| 1EA2 00 | DB | $0 | ;HEAD |
| 1EA3 00 | DB | $0 | |
| 1EA4 42 | DB | $42 | |
| 1EA5 C1 | DB | $C1 | |
| 1EA6 55 | DB | $55 | ;HIGH |
| 1EA7 4A | DB | $4A | |
| 1EA8 50 | DB | $50 | |
| 1EA9 7F | DB | $7F | |
| 1EAA A6 | DB | $A6 | ;INCHES |
| 1EAB 36 | DB | $36 | |
| 1EAC 50 | DB | $50 | |
| 1EAD 81 | DB | $81 | |
| 1EAE 68 | DB | $68 | ;IRREGULAR |
| 1EAF 99 | DB | $99 | |
| 1EB0 84 | DB | $84 | |
| 1EB1 A0 | DB | $A0 | |
| 1EB2 1D | DB | $1D | ;IT |
| 1EB3 1E | DB | $1E | |
| 1EB4 24 | DB | $24 | |
| 1EB5 E2 | DB | $E2 | |
| 1EB6 5A | DB | $5A | ;LOW |
| 1EB7 C9 | DB | $C9 | |
| 1EB8 40 | DB | $40 | |
| 1EB9 C0 | DB | $C0 | |
| 1EBA D8 | DB | $D8 | ;MANIKIN |
| 1EBB 16 | DB | $16 | |
| 1EBC 70 | DB | $70 | |
| 1EBD 47 | DB | $47 | |
| 1EBE D1 | DB | $D1 | ;MORE_AIR |
| 1EBF 4E | DB | $4E | |
| 1EC0 B2 | DB | $B2 | |
| 1EC1 C0 | DB | $C0 | |
| 1EC2 2B | DB | $2B | ;NECK |
| 1EC3 85 | DB | $85 | |
| 1EC4 42 | DB | $42 | |
| 1EC5 81 | DB | $81 | |
| 1EC6 75 | DB | $75 | ;NOTCH |
| 1EC7 40 | DB | $40 | |
| 1EC8 63 | DB | $63 | |
| 1EC9 2C | DB | $2C | |
| 1ECA EF | DB | $EF | ;OF_THE_JAW |
| 1ECB 44 | DB | $44 | |
| 1ECC 73 | DB | $73 | |
| 1ECD C0 | DB | $C0 | |
| 1ECE DA | DB | $DA | ;ON_TOP_OF_IT |
| 1ECF B7 | DB | $B7 | |
| 1ED0 B1 | DB | $B1 | |
| 1ED1 80 | DB | $80 | |
| 1ED2 C9 | DB | $C9 | ;PERFECT |
| 1ED3 8E | DB | $8E | |
| 1ED4 72 | DB | $72 | |
| 1ED5 C0 | DB | $C0 | |
| 1ED6 0A | DB | $A | ;POSITION |
| 1ED7 91 | DB | $91 | |
| 1ED8 60 | DB | $60 | |
| 1ED9 BF | DB | $BF | |

```
1EDA 35             DB      $35     ;PULSE
1EDB C2             DB      $C2
1EDC 41             DB      $41
1EDD 00             DB      $0
1EDE C8             DB      $C8     ;RHYTHM
1EDF E9             DB      $E9
1EE0 40             DB      $40
1EE1 F8             DB      $F8
1EE2 BA             DB      $BA     ;RIGHT
1EE3 D7             DB      $D7
1EE4 40             DB      $40
1EE5 20             DB      $20
1EE6 9D             DB      $9D     ;SHALLOW
1EE7 AF             DB      $AF
1EE8 61             DB      $61
1EE9 FF             DB      $FF
1EEA 92             DB      $92     ;SMOOTHLY
1EEB 91             DB      $91
1EEC 60             DB      $60
1EED 7A             DB      $7A
1EEE 6F             DB      $6F     ;STERNUM
1EEF 24             DB      $24
1EF0 42             DB      $42
1EF1 C0             DB      $C0
1EF2 92             DB      $92     ;TELL_YOU_HOW_YOU_DID
1EF3 AE             DB      $AE
1EF4 D4             DB      $D4
1EF5 38             DB      $38
1EF6 40             DB      $40     ;THE_ADAMS_APPLE
1EF7 01             DB      $1
1EF8 B4             DB      $B4
1EF9 C0             DB      $C0
1EFA 52             DB      $52     ;THRUST2
1EFB AC             DB      $AC
1EFC 45             DB      $45
1EFD 9F             DB      $9F
1EFE 64             DB      $64     ;TO
1EFF BB             DB      $BB
1F00 11             DB      $11
1F01 5E             DB      $5E
1F02 D1             DB      $D1     ;TOO_DEEP
1F03 BB             DB      $BB
1F04 94             DB      $94
1F05 00             DB      $0
1F06 55             DB      $55     ;TWICE
1F07 1A             DB      $1A
1F08 52             DB      $52
1F09 80             DB      $80
1F0A 28             DB      $28     ;VENTILATION
1F0B D1             DB      $D1
1F0C 84             DB      $84
1F0D 50             DB      $50
1F0E E4             DB      $E4     ;WIDE
1F0F 1B             DB      $1B
1F10 60             DB      $60
1F11 38             DB      $38
                ;** END OF TABLES **
                ;
                ;** VECTORS **
1FF4                ORG     $1FF4   ;$1FF4 FOR 6305XXXXXXXXXXXX
1FF4 1000           DW      INIT
1FF6 1000           DW      INIT
1FF8 1000           DW      INIT
1FFA 103F           DW      INT     ;INSERT DW INIT LATERXXXXXX
1FFC 1000           DW      INIT
1FFE 1000           DW      INIT
0000                END
                            ---- SYMBOL TABLE ----

ABLE    006B        CONV    16D1        LTABLE  116B
        AD1     16C1        CP      1390        M       19B3
        ADDIT   1613        CUM     129C        MAXC    006F
        ADDR    0004        CYCLE   0089        MAXVAL  0066
```

| | | | | | |
|---|---|---|---|---|---|
| ADV2 | 16DB | DDDR | 0007 | MEAN | 1595 |
| ADVAL | 008B | DIV | 161E | MESAGE | 1122 |
| AGINHP | 13DC | DIV01 | 1631 | MESSA | 112B |
| ALLBIT | 0042 | DNDLSB | 009A | MESSC | 1151 |
| ALLOVR | 125D | DNDMSB | 0099 | MINCNT | 1254 |
| ANSLSB | 0092 | DOG | 006E | MINCTR | 008C |
| ANSMSB | 0091 | EPRES | 005B | MINTOT | 0074 |
| AVGDEV | 15A8 | FIN | 161D | MINUS | 126A |
| BAD | 141B | FINE | 17B3 | MODATA | 1187 |
| BADC | 0069 | FIRST | 0064 | MORBYT | 1296 |
| BADC1 | 0068 | FORMIN | 0061 | MOVIT | 12F8 |
| BAKER | 006C | FOUR | 10DE | MR | 000A |
| BDDR | 0005 | FOURC | 005E | MTABLE | 1166 |
| BIGGER | 172C | FXWRD | 005A | N | 1AA5 |
| BLH | 0054 | GOBAK | 1121 | NEWNUM | 0096 |
| BUH | 0053 | GOOD | 13FE | NEXWRD | 1159 |
| BYBY | 14B1 | GOODC | 006A | NOGD | 17BA |
| C31 | 17E0 | GOTIT | 1734 | NOT160 | 127E |
| C32 | 17FD | HEAH | 116E | NOTCCR | 10B9 |
| C33 | 17D8 | HI | 16B3 | NOTCP | 10D1 |
| C34 | 17F0 | HOP | 1288 | NOTHP | 10C9 |
| C35 | 17DF | HP | 13C3 | NOTHT | 10B1 |
| C36 | 1804 | HP2 | 169D | NOTM | 1140 |
| C37 | 180B | HP3 | 16A0 | NOTSCC | 10C1 |
| CANSTR | 008E | HP4 | 16A6 | NOTSSS | 11D5 |
| CBIN1 | 0070 | HPCHEK | 169A | NOTTEE | 11E0 |
| CBIN2 | 0071 | HPSTOR | 0063 | NOZERO | 1630 |
| CBIN3 | 0072 | HT | 1668 | NUBGIN | 109C |
| CCR | 150A | I | 1812 | NUMBER | 17BD |
| CCR1 | 1535 | IN | 124A | NUMWRD | 0056 |
| CCR11 | 160F | INIT | 1000 | NXBIN1 | 1793 |
| CCR13 | 154A | INT | 103F | NXBIN2 | 17A3 |
| CCR14 | 154D | JUSTAD | 1705 | OFFC | 16BA |
| CCR2 | 1550 | L | 18B6 | ON | 1103 |
| CCR3 | 160A | LAMP | 0060 | ON1 | 1438 |
| CCR4 | 1563 | LAMPON | 1101 | ONMESS | 1245 |
| CCR5 | 15FC | LAMPS | 1744 | ONWAIT | 111D |
| CCR7 | 15F9 | LASTMS | 0043 | OU | 1264 |
| CCR8 | 15FE | LD2LSB | 1190 | OUT | 126E |
| CCRA | 151A | LDSREG | 1197 | OUTD | 1639 |
| CCRB | 1605 | LETGO | 14DE | OVER | 1657 |
| CDDR | 0006 | LICAND | 008F | PERCTR | 0073 |
| CHUCK | 006D | LONG | 11BF | PERIOD | 007A |
| CLEAR | 1038 | LOOP | 163E | PLAOLD | 113C |
| CLOSER | 14F5 | LOOP3 | 1633 | PLIER | 0090 |
| CLRAMO | 1036 | LOOP4 | 15AF | PORTA | 0000 |
| COMEUP | 1568 | LTAB | 114B | PORTB | 0001 |
| PORTC | 0002 | SENSIT | 008A | TOOLOW | 16AC |
| PORTD | 0003 | SIGMA | 0079 | TOTLSB | 0094 |
| POSTIV | 15B6 | SILA | 11AE | TOTMSB | 0095 |
| PWROFF | 10FD | SILB | 11BC | U | 1D56 |
| QUOTNT | 009C | SILBYT | 11A2 | UP | 146E |
| RAMBIT | 0040 | SILC | 11CD | UP1 | 148C |
| READO | 16DD | SILD | 11D1 | UP2 | 1497 |
| READY | 11EE | SILE | 11C9 | UP3 | 14EC |
| REGLAR | 119E | SILO | 11B3 | UP4 | 14E5 |
| REST | 1587 | SILREG | 0059 | UP5 | 14AA |
| RUN1 | 1053 | SLH | 0052 | UP6 | 1483 |
| RUN3 | 106B | SMPNEW | 0067 | UP7 | 14D0 |
| RUN4 | 10D4 | SMPOL1 | 0076 | V | 1E32 |
| RUN4A | 1074 | SMPOL2 | 0077 | V1 | 1304 |
| RUN6 | 107D | SMPOLD | 0075 | V10 | 1362 |
| RUN7 | 10DC | SOMEMO | 10E3 | V11 | 136F |
| RUNBIT | 0041 | SORLSB | 0098 | V12 | 1388 |
| RUNC1 | 1459 | SORMSB | 0097 | V2 | 12DD |
| RUNC2 | 16CA | SPK | 1177 | V3 | 12E4 |
| RUNC3 | 1709 | SSAW | 0058 | V4 | 12EE |
| RUNC5 | 1738 | ST | 1032 | V5 | 131A |
| S | 1B92 | SUH | 0051 | V6 | 130F |
| SAM | 0055 | SVAGIN | 12BE | V7 | 132F |
| SAMPLE | 008D | SWOLD | 0062 | V8 | 1336 |
| SCC | 143D | T | 1C6E | V9 | 1340 |
| SCICR | 0010 | TALKCP | 139C | VENT | 12A0 |

| | | | | | |
|---|---|---|---|---|---|
| SCIDR | 0012 | TALKHP | 13CF | VWRD | 11EB |
| SCISR | 0011 | TALKHT | 1672 | WAIT | 110A |
| SCOR1 | 1760 | TALKV | 12B1 | WAITC | 005D |
| SCOR2 | 1775 | TCR | 0009 | WAITMO | 1110 |
| SCOR4 | 1755 | TDR | 0008 | WDAR | 0050 |
| SCOR5 | 1753 | TELLIT | 173C | WRDOFF | 0057 |
| SCOR6 | 1767 | TEMP1 | 0093 | WRDTAB | 005C |
| SCOR7 | 1770 | TEMP2 | 009B | XBAR | 0078 |
| SCOR8 | 1779 | TENMO | 10F9 | ZOT | 1653 |
| SCORC1 | 174B | TH1 | 0065 | ZZSPK | 1209 |
| SCORC2 | 177C | TIMEUP | 157B | ZZSPK1 | 120E |
| SCORC3 | 17C5 | TINUE | 1291 | ZZWAIT | 111A |

The invention claimed is:

1. In a manikin for use by a student practicing a procedure and having sensor means adapted to detect certain of the student's actions and to produce a feedback signal proportional to such actions, the improvement comprising:

scoring means, responsive to the sensor means, for promptly assigning a detected feedback signal to the appropriate one of a plurality of predetermined range scores (S1, S2, . . . SN); and real-time voice feedback means, responsive to the range score (S1, S2, . . . SN) assigned by the scoring means for promptly generating an appropriate simulated voice message (M1, M2, . . . MN) as aural feedback relating to the student's performance.

2. The improvement of claim 1 wherein the real-time voice feedback means is a coaching message of very brief duration.

3. The improvement of claim 2 wherein the coaching message is about ½ second or less.

4. The improvement of claim 1 wherein the manikin has:

an inlet, leading to an expandable air chamber adapted to represent the manikin's lungs, into which the student can blow air to practice artificial respiration, and the sensor means comprises a position-sensitive sensor operatively connected to the manikin's air chamber for detecting the relative volume of air in the chamber and producing a feedback signal representative of the amount of air blown in by the student.

5. The improvement of claim 4 wherein the position-sensitive sensor is a transducer adapted to produce a feedback signal sufficiently proportional to the volume of air in the manikin's air chamber to permit the feedback signal to be distinguished among the following ranges with respect to human lungs being artificially respirated:

critically too much air
too much air but not critically so
an acceptable amount of air
too little air but not critically so
critically too little air and the voice feedback means is adapted to generate a corresponding simulated voice message for each of these ranges.

6. The improvement of claim 4 wherein the position-sensitive sensor is a transducer adapted to produce a feedback signal sufficiently proportional to the volume of air in the manikin's air chamber to enable the feedback signal to be distinguished among the following ranges with respect to human lungs being artificially respirated:

critically too much air
too much air but not critically so
an acceptable amount of air
too little air but not critically so
critically too little air and further comprising display means, responsive to the feedback signal, for visually indicating into which of these ranges the feedback signal falls.

7. The improvement of claim 1 wherein:

the manikin has a resiliently compressible chest portion adapted to represent a sternum on which the student can press to compress the chest of the manikin for practice of external cardiac compression;

and the sensor means comprises a position-sensitive sensor operatively connected to the manikin's chest portion for detecting the position of the chest portion and producing a feedback signal representative of the amount by which the student compresses the chest portion.

8. The improvement of claim 7 wherein the position-sensitive sensor is a transducer adapted to produce a feedback signal sufficiently proportional to the distance the chest portion is compressed to enable the feedback signal to be distinguished among the following ranges with respect to external cardiac compression on a human chest:

critical overcompression
unacceptable but less than critical overcompression
acceptable compression
unacceptable but not critical undercompression
critical undercompression and the voice feedback means is adapted to generate an appropriate simulated voice message for each of these ranges.

9. The improvement of claim 7 wherein the position-sensitive sensor is a transducer adapted to produce a feedback signal sufficiently proportional to the distance the chest portion is compressed to enable the feedback signal to be distinguished among the following ranges with respect external cardiac compression on a human chest:

critical overcompression
unacceptable but less than critical overcompression
acceptable compression
unacceptable but not critical undercompression
critical undercompression and further comprising display means, responsive to the feedback signal, for visually indicating into which of these ranges the feedback signal falls.

10. The improvement of claim 1 wherein the particular simulated voice message generated by the real-time voice feedback means includes a word of praise or corrective advice, whichever is appropriate for the range score to which the message corresponds, whereby helpful human coaching is simulated.

11. The manikin of claim 1:
further comprising memory means for storing successive range scores corresponding to a sequence of successive attempts by the student, and computation means responsive to the stored range scores for computing a summary score for the sequence of attempts;
wherein the voice feedback means includes summary score reporting means, responsive to the summary score computed by the computation means, for generating a corresponding appropriate simulated voice message as aural feedback on performance of the sequence to the student.

12. The manikin of claim 11 wherein, for a sequence of successive attempts by the student, the computation means is adapted to calculate totals (T1, T2,... TN) of the number of times each range score (S1, S2,... SN respectively) is stored in the memory means, and to include such totals in the summary score for the sequence of attempts.

13. The improvement of claim 1:
including memory means for storing the feedback signals corresponding to a sequence of successive attempts by the student, and computation means responsive to the feedback signals stored in the memory means for computing a composite score for the sequence of attempts;
wherein the voice feedback means includes composite score reporting means, responsive to the composite score computed by the computation means, for generating an appropriate simulated voice message as aural feedback relating to the performance of the student.

14. The improvement of claim 13 wherein, for a sequence of successive attempts by the student, the computation means is adapted to average the feedback signals stored in the memory means, and to include the average in the composite score for the sequence of attempts.

15. The improvement of claim 13 wherein, for a sequence of successive attempts by the student, the computation means is adapted to compute the standard deviation of the feedback signals stored in the memory means, and to include the standard deviation in the composite score for the sequence of attempts.

16. The improvement of claim 13 wherein, for a sequence of successive attempts by the student, the computation means is adapted to compute both the average and standard deviation of the feedback signals stored in the memory means, and to include the average and standard deviation the computation means in the composite score for the sequence of attempts.

17. The improvement of claim 1 including:
abstracting means for calculating an attribute of the feedback signal,
memory means for storing the attributes corresponding to a sequence of successive attempts by the student, and
computation means, responsive to the attributes stored in the memory means, for computing a composite score for the sequence of attempts;
wherein the voice feedback means includes composite score reporting means, responsive to the composite score computed by the computation means, for generating a simulated voice message which is appropriate to the performance of the sequence as aural feedback to the student.

18. The improvement of claim 17 wherein, for a sequence of successive attempts by the student, the computation means is adapted to average the attributes stored in the memory means, which average the computation means includes in computing the composite score for the sequence of attempts.

19. The improvement of claim 17 wherein, for a sequence of successive attempts by the student, the computation means is adapted to compute the standard deviation of the attributes stored in the memory means, and to include said standard deviation in the composite score for the sequence of attempts.

20. The improvement of claim 17 wherein, for a sequence of successive attempts by the student, the computation means is adapted to compute both the average and standard deviation of the attributes stored in the memory means, and to include the average and standard deviation in the composite score for the sequence of attempts.

21. In a manikin for use by a student practicing a procedure applied to the human body and having sensor means adapted for detecting certain of the student's actions and producing a signal representative of each occurrence of such action, the improvement comprising:
scoring means, responsive to the sensor means, for promptly assigning the signal representing each action to the appropriate one of a plurality of predetermined range scores (S1, S2, ... SN);
memory means for storing successive range scores corresponding to a sequence of successive actions by the student;
computation means, responsive to the successive range scores stored in the memory means, for computing a composite score (C) for the sequence of actions; and
real-time visual display feedback means, responsive to the composite score (C) computed by the computation means, for generating a visual indication representing a message (MC) which is appropriate to the performance of the sequence by the student.

22. The manikin of claim 21 wherein the computation means is adapted to compute the average of the successive scores and to employ that average as the composite score (C) for the sequence of actions.

23. The manikin of claim 21 wherein the computation means is adapted to compute the standard deviation of the successive scores and to employ that standard deviation as the composite score (C) for the sequence of actions.

24. The manikin of claim 21 wherein the computation means is adapted to produce two composite scores, both the average (C1) and standard deviation (C2) of the successive scores, and the composite score reporting means is responsive to these two composite scores to generate an indicium representing a two-component message (MC1+MC2) as aural feedback regarding the student's performance of the sequence.

25. In a teaching system having a manikin for use by a student practicing cardiopulmonary resuscitation under the supervision of an instructor, the improvement comprising:
a remote control activator unit for the instructor having transmitter means for sending remote control signals to the manikin from a location remote from the manikin, including manual selection means on the transmitting unit for selecting an enable signal;

a receiver for receiving the remote control signal sent by the transmitter unit and determining if it is an enable signal;

and simulator means comprising a sound generator and responsive to detection of the enable signal by the receiver for generating a sound simulating breathing in the vicinity of said manikin.

26. The improvement of claim 25 wherein said remote control signal is wireless.

27. The improvement of claim 26 wherein the transmitter is an infrared transmitter and the receiver is a matching infrared receiver.

28. The improvement of claim 26 wherein the transmitter is an ultrasonic transmitter and the receiver is a matching ultrasonic receiver.

29. The improvement of claim 26 wherein the transmitter is a radio transmitter and the receiver is a matching radio receiver.

30. In a teaching system having a manikin for use by a student practicing cardiopulmonary resuscitation under the supervision of an instructor, the improvement comprising:

a remote control activator unit for the instructor having transmitter means for sending remote control signals to the manikin from a location remote from the manikin, including manual selection means on the transmitting unit for selecting an enable signal;

a receiver for receiving the remote control signal sent by the transmitter unit and determining if it is an enable signal;

and pulse simulator means mounted in a neck region of the manikin, responsive to a detection of the enable signal by the receiver for producing a simulated carotid pulse.

31. The improvement of claim 30 wherein said remote control signal is wireless.

32. The improvement of claim 31 wherein the transmitter is an infrared transmitter and the receiver is a matching infrared receiver.

33. The improvement of claim 31 wherein the transmitter is an ultrasonic transmitter and the receiver is a matching ultrasonic receiver.

34. The improvement of claim 31 wherein the transmitter is a radio transmitter and the receiver is a matching radio receiver.

35. A manikin system for use by a student practicing a procedure applied to the human body, including a manikin on which the student can practice, a speech memory having prerecorded coaching messages stored therein, a controller for selecting said prerecorded coaching messages, message reproducing means for voicing the messages selected by the controller for guiding the student, sensor means adapted for detecting certain of the student's actions on the manikin and producing an evaluation score, at least some of the messages being selected by the controller in accordance with the calculated evaluation score, memory means for storing an indicium of the last message voiced by the message reproducing means, manual selector means for generating a REPEAT signal, message repeater means responsive to said REPEAT signal for interrupting the current task of the controller and reading the indicium from the memory means, and responsive to said indicium for causing the controller to select the previous message to be voiced again by the message reproducing means.

36. A controller system for use with a manikin on which a student can practice a procedure normally applied to the human body, said system comprising:

sensor means adapted to be mounted in the manikin for generating signals indicative of the instantaneous amplitude of the procedure being practiced on the manikin by the student over a range of instantaneous amplitudes;

input means for receiving the signals from the sensor means;

memory means containing microprocessor instructions for a teaching routine for the procedure to be practiced;

processing means responsive to the teaching routine instructions and the input means to produce audio-frequency output signals; and speech synthesizer means responsive to the audio-frequency output signals to produce simulated voice feedback to the student which varies as a function of said amplitude.

37. The system of claim 36 wherein the processing means also produces visual display driver signals and further comprising display means responsive to the display driver signals to produce visual feedback to the student which varies as a function of said amplitude.

38. The system of claim 36 for use with a manikin that has an expandable air chamber which expands when air is blown into it by the student to practice artificial respiration, wherein the sensor means includes a position sensor mounted to detect the instantaneous expansion of the chamber for generating signals indicative of the instantaneous amount of air in the chamber.

39. The system of claim 38 wherein the processing means also produces visual display driver signals and the controller includes visual display means comprising a plurality of discrete indicator lamps and responsive to the display driver signals to indicate the instantaneous amount of air in the chamber by turning on a corresponding number of the indicator lamps.

40. The system of claim 38 wherein the processing means includes peak detector means for determining the magnitude of a local maximum in the amplitude-representing signal, and classifying means for classifying the magnitude of the local maximum as indicating either too little, an acceptable amount, or too much air in the manikin's air chamber.

41. The system of claim 40 wherein for a preselected number of artificial respirations practiced by the student the processing means includes tallying means responsive to the classifying means for determining the number of respirations that were too little, the number that were an acceptable amount, and the number that were too much.

42. The system of claim 38 wherein the processing means includes peak detector means for determining the magnitude of a local maximum in the amplitude-representing signal, and classifying means for classifying the magnitude of the local maximum as either indicating much too little, somewhat too little, an acceptable amount, somewhat too much, or much too much air in the manikin's air chamber.

43. The system of claim 42 wherein the speech synthesizer means are responsive to the classifying means to promptly produce a brief simulated voice comment corresponding to whether the amplitude of the local maximum of the detection signal indicates much too little, somewhat too little, an acceptable amount, somewhat too much, or much too much air in the manikin's air chamber.

44. The system of claim 36 for use with a manikin that has a resilient chest portion which is compressible when pressed down by the student to practice external cardiac compression, wherein the sensor means has a position sensor mounted for generating detection signals indicative of the instantaneous compression of the chest.

45. The system of claim 44 wherein the processing means also produces display driver signals and the controller includes visual display means comprising a plurality of indicator lamps responsive to the display driver signals to indicate the instantaneous amount of compression of the manikin's chest by turning on a corresponding number of the indicator lamps.

46. The system of claim 44 wherein the processing means includes peak detector means for determining the magnitude of a local maximum in the amplitude-representing signal, and classifying means for classifying the magnitude of the local maximum as indicating either too little, an acceptable amount, or too much compression of the manikin's chest.

47. The system of claim 46 wherein for a preselected number of chest compressions practiced by the student the processing means includes tallying means responsive to the classifying means for determining the number of compressions that were too little, the number that were an acceptable amount, and the number that were too much.

48. The system of claim 44 wherein the processing means includes peak detector means for determining the magnitude of a local maximum in the amplitude-representing signal, and classifying means for classifying the magnitude of the local maximum as either indicating much too little, somewhat too little, an acceptable amount, somewhat too much, or much too much compression of the manikin's chest.

49. The system of claim 48 wherein the speech synthesizer means is responsive to the classifying means to promptly produce a brief simulated voice comment as to whether the magnitude of the local maximum of the amplitude-representing signal indicates much too little, somewhat too little, an acceptable amount, somewhat too much, or much too much compression of the manikin's chest.

50. The system of claim 44 wherein for a preselected number of chest compressions sequentially practiced by the student the processing means includes peak detector means for determining the time of each local maximum in the amplitude-representing signal, and timer means responsive to the peak detector means for measuring the period between a pair of successive maxima.

51. The system of claim 50 wherein the timer means measures the period between each pair of successive maxima of the preselected number of chest compressions, and the processing means includes averaging means responsive to the timer means for determining the arithmetic average of the periods, and rhythm-checking means responsive to the averaging means for producing a brief simulated voice comment as to whether the average of the periods corresponds to a rhythm of the chest compressions that is too slow, acceptable, or too fast.

52. The system of claim 51 wherein the processing means includes estimating means responsive to the periods measured by the timer means and the arithmetic average determined by the averaging means for estimating the standard deviation of the periods and producing a brief simulated voice comment as to whether the estimated standard deviation corresponds to a rhythm that is regular or irregular.

53. The system of claim 36 for use with a manikin that has a resilient chest portion which is compressible when pressed down by the student's hands to practice external cardiac compression, wherein the sensor means includes a hand-position sensor adapted to be mounted in said chest portion for generating signals indicating whether the hands of the student are pressing on a preselected correct location on the manikin's chest or are displaced from said correct location, and the speech synthesizer means produces simulated voice feedback to the student as to the correctness of said hand position.

54. A chest compression training device comprising:
means for simulating a compressible chest of a patient and including a correct hand position area for chest compression;
means for detecting the existence and direction of an error in hand position committed by a student employing said training device;
and a read-out comprising a correct position indicium, a plurality of indicator lamps arranged in a ring surrounding said indicium, and means responsive to the detection of a hand position error by said detecting means to light whichever of said lamps represent the direction of said hand position error in relation to said indicium.

55. A lightweight, compact, portable, videoless training manikin system for communicating with a student by means of realistic, real-time audio messages whereby the student's attention is not diverted by the need to view a pictorial display, said system comprising:
a simulated human figure;
sensor means incorporated into said simulated human figure and adapted to detect certain of said student's actions performed on said manikin, and to produce a feedback signal representative of such actions;
electronic circuitry means to interpret said feed back signals to produce a response useful in training said student;
at least part of said electronic circuitry being incorporated into said simulated human figure;
that portion of said circuitry, if any, which is detached from said simulated human figure occupying a volume smaller than that of said simulated human figure, whereby said system is either the same size as, or a little larger than, said simulated human figure to facilitate portability of said system;
said circuitry including scoring means responsive to said sensor means for assigning a score to a feedback signal from said sensor means, and
exclusively electronic random-access voice message signal synthesizing means lacking any moving mechanical parts,
said synthesizing means being responsive to said voice to produce an immediate signal representing a simulated voice feedback message relating to the student's performance,
and audio transducer means responsive to said voice message signal to enunciate a voice message to the student.

56. A manikin for use by a student practicing a procedure normally applied to the human body comprising:
sensor means adapted to detect certain of the student's actions and to produce a feedback signal proportional to such actions;

interpreting means to periodically evaluate said feedback signal and measure the correctness of said actions of the student;

and means to indicate to the student when said interpreting means is actively evaluating said feedback signal produced from said sensor means.

* * * * *

UNITED STATES PATENT AND TRADEMARK OFFICE
CERTIFICATE OF CORRECTION

PATENT NO. : 4,828,501
DATED : MAY 9, 1989
INVENTOR(S) : INGENITO ET AL

It is certified that error appears in the above—identified patent and that said Letters Patent is hereby corrected as shown below:

IN THE DRAWINGS:

In sheet 3, Fig. 4, add the reference number --128-- to refer to the remote control transmitter block labelled "CP & SB TRANSMITTER".

In Sheet 3, Fig. 4, add the reference characters --97f-- to refer to the OR-gate adjacent flip-flop 97e.

In Sheet 3, Fig. 4, change the legend in the circular supply voltage terminal immediately above the reference number "71" from "V" to --+V--.

In Sheet 6, Fig. 7C, add reference number --190-- to refer to the ground-connected output terminal of potentiometer 118.

Figure 8D:
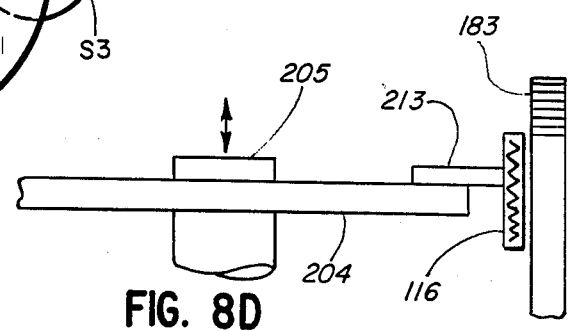
FIG. 8D is an enlarged view of the switchplate of FIG. 8A, showing its cooperation with a potentiometer for detecting its position.

In Sheet 7, Fig. 8D, add reference number --188-- to refer to the vertical support adjacent potentionmeter 116.

In Sheet 9, Fig. 10, add reference characters --129f-- to refer to the transistor.

UNITED STATES PATENT AND TRADEMARK OFFICE
CERTIFICATE OF CORRECTION

PATENT NO.   :   4,828,501
DATED        :   MAY 9, 1989
INVENTOR(S)  :   INGENITO ET AL

It is certified that error appears in the above—identified patent and that said Letters Patent is hereby corrected as shown below:

In Sheet 9, Fig. 10, add reference characters --dI-- to refer to all three light-emitting diodes.

In Sheet 10, Fig. 11, delete the reference number "232" and accompanying arrow referring to the legend "PROGRAM ROUTINES".

In Sheet 11, Fig. 12A, in rectangular blocks 271 and 282, change the word "FORMIN" to --FOURMIN--.

Figure 12B:
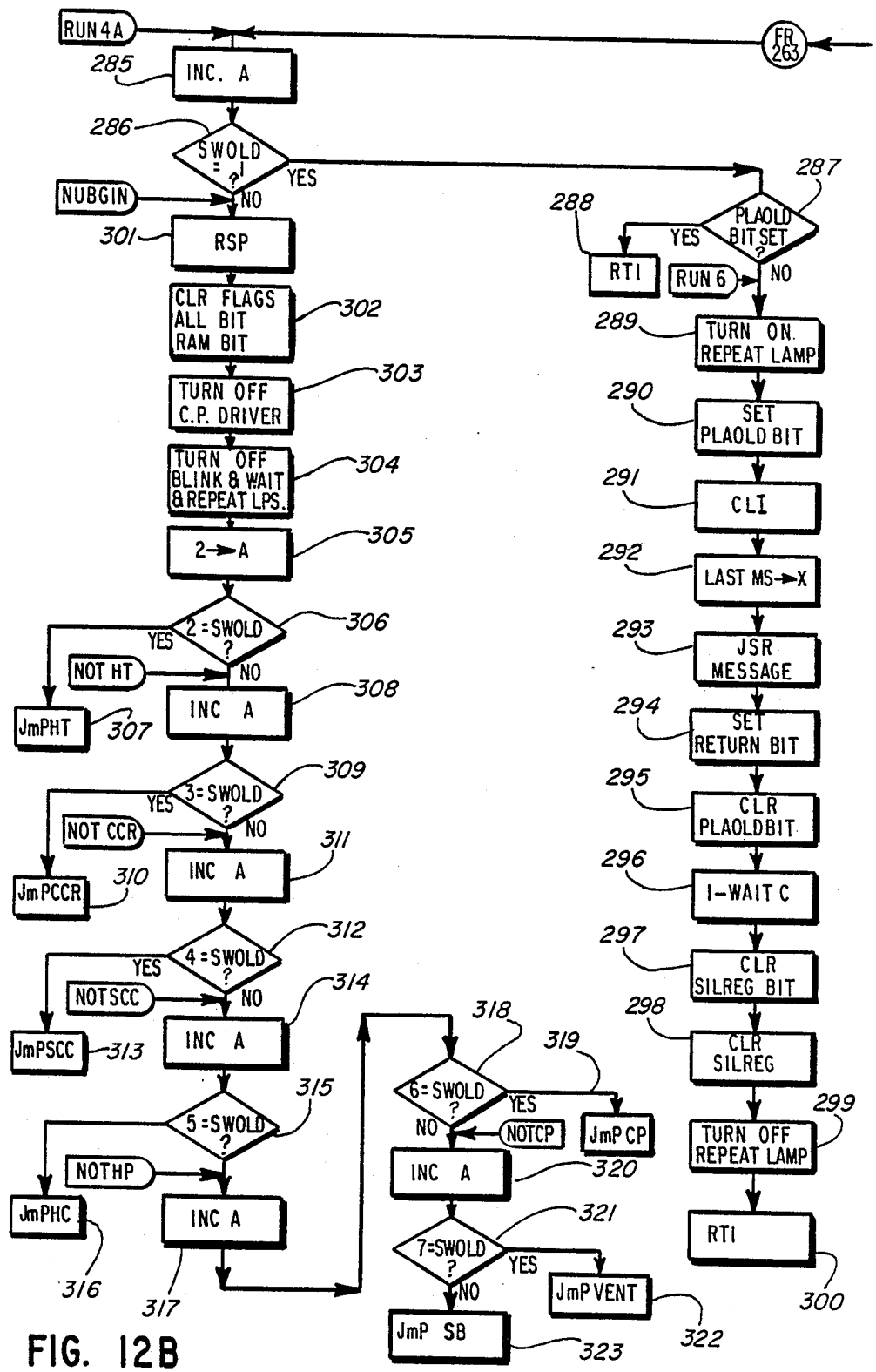

In Sheet 12, Fig. 12B, in rectangular block 296, add a right-pointing arrow between "1" and "WAITC".

In Sheet 13, Fig. 13A, change the downward-pointing arrow associated with the off-page connector circle labeled "FR. 364" to an upward-pointing arrow.

In Sheet 17, Fig. 16, correct the legend in decision diamond 444 by deleting the period preceeding "96".

In Sheet 18, Fig. 17, under the legend "CHEST COMPRESSION", change "THM" TO --RHYTHM--.

UNITED STATES PATENT AND TRADEMARK OFFICE
CERTIFICATE OF CORRECTION

PATENT NO. : 4,828,501
DATED : MAY 9, 1989
INVENTOR(S) : INGENITO ET AL

Figure 17B:
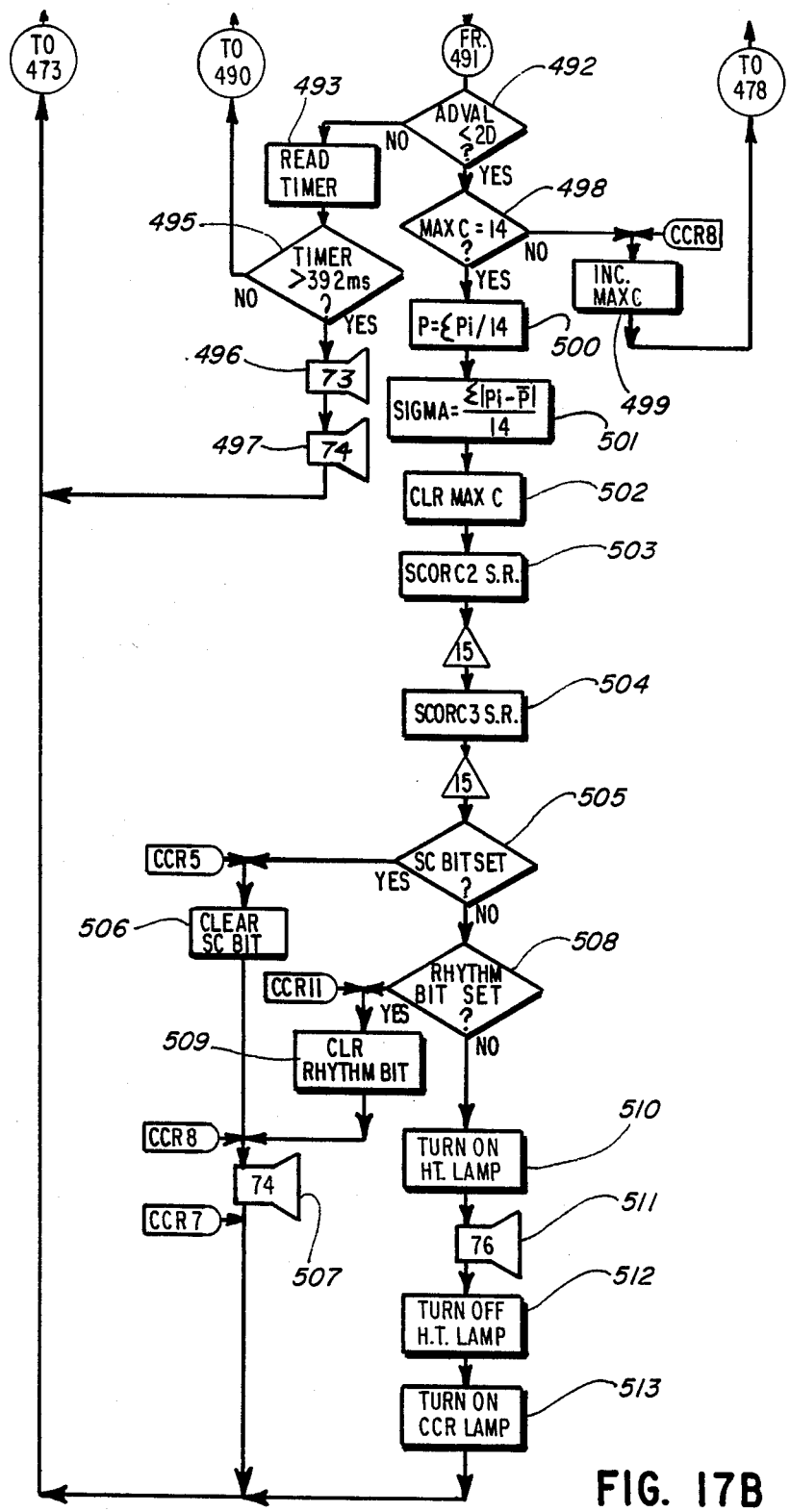
Figure 20:
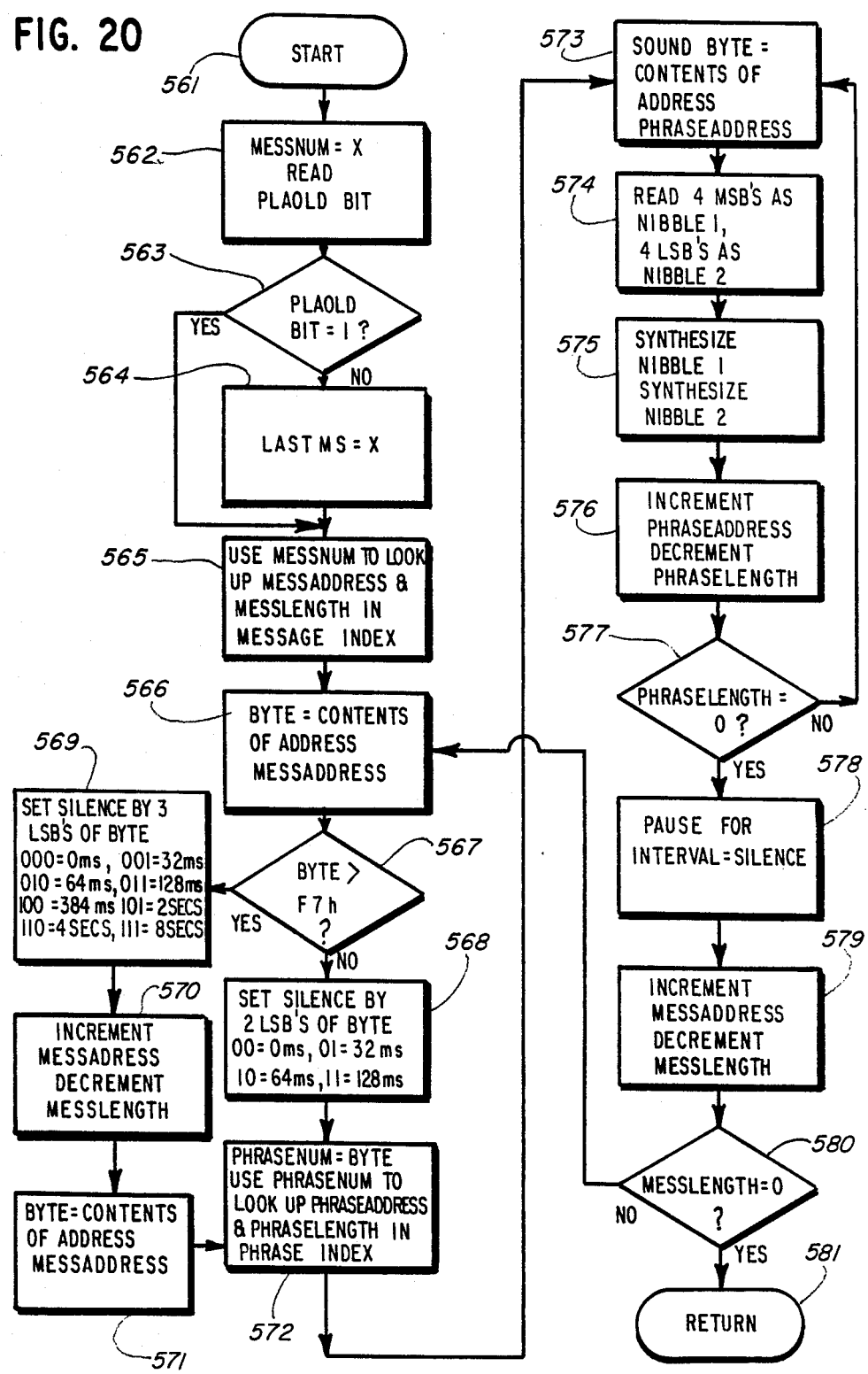
FIG. 20 is a flow chart for an embodiment of the Message Subroutine incorporated in the Control Program of FIG. 11.

It is certified that error appears in the above—identified patent and that said Letters Patent is hereby corrected as shown below:

In Sheet 19, Fig. 17B, correct the legend in block 500 by adding a superscript bar over the first "P".

In Sheet 20, Fig. 19, change the legend for table 527 from "SPEECH MEMORY (384 IKBYTES)" TO --SPEECH MEMORY (384 KBYTES)--.

In Sheet 22, Fig. 21A, add the legends --YES-- to the right-hand branch, and --NO-- to the downward branch, leading from decision diamond 600.

In Sheet 22, Fig. 21A, in the rectangular block 607, add a right-pointing arrow between "SMPOL1" and "MAXVAL".

In Sheet 23, Fig. 22A, in diamond 619, change "BIT 0 OF 3" to --BIT 0 OR 3--.

In Sheet 23, Fig. 22B, change the legend above bit 6 of HPSTORE from "HJ 6" to --HS 6--.

In Sheet 24, Fig. 23, change the legend in decision diamond 631 from "A $\geq$ C8 h ?" to --A $\leq$ C8 h ?--.

UNITED STATES PATENT AND TRADEMARK OFFICE
CERTIFICATE OF CORRECTION

PATENT NO. : 4,828,501
DATED : MAY 9, 1989
INVENTOR(S) : INGENITO ET AL

It is certified that error appears in the above—identified patent and that said Letters Patent is hereby corrected as shown below:

IN THE SPECIFICATION:

In col. 9, line 17, after "memory chip" insert --104--.

In col. 14, line 62, change "183" to --188--.

In col. 16, line 31, change "an X" to --a circle--.

In col. 19, lines 47, 48, and 51, change "129e" to --129f--.

In col. 20, line 20, delete "232".

In col. 24, line 67, change "8 and 9" to --9 and 10--.

In col. 30, line 13, change "441" to --44--.

In col. 30, line 29, change "liters)," to --inches),--.

In col. 31, line 63, change "is also is" to --is also--.

In col. 32, line 35, change "236," to --400,--.

UNITED STATES PATENT AND TRADEMARK OFFICE
CERTIFICATE OF CORRECTION

PATENT NO. : 4,828,501

DATED : MAY 9, 1989

INVENTOR(S) : INGENITO ET AL

It is certified that error appears in the above-identified patent and that said Letters Patent is hereby corrected as shown below:

In cols. 51 and 52, line 28, change "APPENDIX A" to --APPENDIX II--.

Signed and Sealed this

Fourth Day of September, 1990

Attest:

HARRY F. MANBECK, JR.

*Attesting Officer*    *Commissioner of Patents and Trademarks*